(12) United States Patent
Goto

(10) Patent No.: US 8,157,858 B2
(45) Date of Patent: Apr. 17, 2012

(54) STENT AND STENT DELIVERY DEVICE

(75) Inventor: Hiroki Goto, Kanagawa-ken (JP)

(73) Assignee: Terumo Kabushiki Kaishia, Shibuya-Ku, Tokyo (JP)

( * ) Notice: Subject to any disclaimer, the term of this patent is extended or adjusted under 35 U.S.C. 154(b) by 1028 days.

(21) Appl. No.: 11/905,347

(22) Filed: Sep. 28, 2007

(65) Prior Publication Data

US 2008/0077228 A1 Mar. 27, 2008

Related U.S. Application Data

(63) Continuation-in-part of application No. 11/392,491, filed on Mar. 30, 2006, now Pat. No. 7,879,084.

(30) Foreign Application Priority Data

Mar. 30, 2005 (JP) .................................. 2005-100193
Sep. 28, 2006 (JP) .................................. 2006-265505

(51) Int. Cl.
*A61F 2/06* (2006.01)
*A61F 2/24* (2006.01)
(52) U.S. Cl. ........................................ 623/1.16; 606/194
(58) Field of Classification Search .................. 623/1.15; 606/1.16, 191, 194, 195, 198
See application file for complete search history.

(56) References Cited

U.S. PATENT DOCUMENTS

| 5,931,867 | A | | 8/1999 | Haindl | |
|---|---|---|---|---|---|
| 6,136,023 | A | * | 10/2000 | Boyle | ........................... 623/1.22 |
| 6,565,598 | B1 | * | 5/2003 | Lootz | ............................ 623/1.15 |

FOREIGN PATENT DOCUMENTS

| EP | 0 873 727 A2 | 10/1998 |
|---|---|---|
| EP | 1 095 632 A2 | 5/2001 |
| JP | 2002-136601 A | 5/2002 |
| JP | 2002-172176 A | 6/2002 |
| JP | 2004-500961 A | 1/2004 |
| JP | 2004-121342 A | 4/2004 |
| JP | 2004-525729 A | 8/2004 |

(Continued)

OTHER PUBLICATIONS

European Search Report dated Jun. 30, 2006.

(Continued)

*Primary Examiner* — Vy Q Bui
(74) *Attorney, Agent, or Firm* — Buchanan Ingersoll & Rooney PC

(57) ABSTRACT

A stent has a plurality of wavy annular members arranged adjacently to each other in an axial direction of the stent with the adjacent wavy annular members connected with each other. Each of the wavy annular members has a plurality of one-end side bent portions each having an apex at one-end side of the stent in an axial direction thereof and a plurality of other-end side bent portions each having an apex at the other-end side of the stent in the axial direction thereof. An apex of each of the one-end side bent portions of each wavy annular member penetrates into a space formed between the adjacent other-end side bent portions of one of the adjacent wavy annular members. An apex of each of the other-end side bent portions of each wavy annular member penetrates into a space formed between the adjacent one-end side bent portions of the other of the adjacent wavy annular members. The apex of the one-end side bent portion of each wavy annular member and the apex of the other-end side bent portion of the adjacent wavy annular member curve in an approach direction, thus engaging each other.

39 Claims, 46 Drawing Sheets

FOREIGN PATENT DOCUMENTS

WO       WO 02/00138 A2    1/2002
WO       WO 02/091958 A1   11/2002

OTHER PUBLICATIONS

Official Action dated Aug. 2, 2011, issued by the Japanese Patent Office in corresponding Japanese Patent Application No. 2006-265505, and partial English language translation of the Official Action.

Official Action dated Jun. 28, 2011, issued by the Japanese Patent Office in corresponding Japanese Patent Application No. 2006-095759, and partial English language translation of the Official Action.

* cited by examiner

STENT AND STENT DELIVERY DEVICE

BACKGROUND OF THE INVENTION

The present invention relates to a stent that is implanted in lumens of an organism such as the blood vessel, the bile duct, the trachea, the esophagus, the ureter, and the like to improve a stenosed portion or a closed portion generated in the lumens. The present invention also relates to a stent delivery device.

To cure various diseases that are caused when the blood vessel or lumens are stenosed or closed, the stent which is a tubular medical appliance is implanted at the stenosed portion or the dosed portion to expand them and secure the lumen thereof.

Because the stent is inserted into the body from the outside, its diameter is small. The stent is expanded to make its diameter large at the stenosed portion or the closed portion to keep the expanded state of the lumen thereof.

The stent is cylindrical and made of a metal wire or a processed metal pipe. After the stent is mounted on a catheter or the like by decreasing its diameter, it is inserted into the body. Thereafter the stent is expanded at a desired portion by using an expanding method and fixed to an inner wall of the lumen of the desired portion, with the stent in close contact therewith to maintain the configuration of the lumen. The stent is classified into a self-expandable stent and a balloon expandable stent in dependence on the function thereof and an implantation method. The balloon expandable stent which itself has no expanding function is secured at a desired portion. Then, a balloon provided in the stent is inflated to expand (plastically deform) the stent by an expansive force of the balloon so that the stent is brought into dose contact with the inner surface of the desired lumen. It is necessary to perform an operation of expanding the stent of this type in implanting it to the desired portion of the organism.

The balloon expandable stent is mostly used as the stent to be used to cure blood vessels and particularly the coronary arteries. The stent is demanded to have an axially flexible construction to cope with a lot of cases.

The balloon expandable stent is classified into a closed cell type and an opened cell type in dependence on the configuration of a stratum thereof. The balloon expandable stent of the opened cell type has an advantage that it is flexible. Thus the balloon expandable stent of the opened cell type is favorably implanted in a desired portion because it is capable of flexibly following a travel direction of a blood vessel and its configuration. Thereby it is possible to prevent the blood vessel from being stimulated. But the balloon expandable stent of the opened cell type has a disadvantage that the stratum thereof flares outward. On the other hand, the balloon expandable stent of the dosed cell type has an advantage that the stratum thereof does not flare outward, but is incapable of flexibly following the travel direction of the blood vessel and its configuration. The balloon expandable stent of the opened cell type and the dosed cell type have both the advantage and the disadvantage. Thus it is necessary to use the balloon expandable stent of the opened cell type or the closed cell type in dependence on the travel direction and configuration of the blood vessel.

The balloon expandable stent of the opened cell type is proposed by the present applicant and disposed in JPA No. 2002-136601.

The balloon expandable stent of the opened cell type disclosed in JPA No. 2002-136601 has a sufficient expanded state retention force owing to the opened cell portion thereof. But it is desirable that the stent has a higher expanded state retention force. It is also desirable that it has a higher follow-up performance for the configurations of organs of the organism.

It is an object of the present invention to provide a stent to be implanted in an organism, which has a high follow-up performance for the configurations of organs of the organism and provide a high expanded state retention force. It is another object of the present invention to provide a stent delivery device.

SUMMARY OF THE INVENTION

The object described above is attained by the following a stent.

A stent comprises a plurality of wavy annular members arranged adjacently to each other in an axial direction thereof with said adjacent wavy annular members connected with each other, wherein each of said wavy annular members has a plurality of one-end side bent portions each having an apex at one side of said stent in an axial direction thereof and a plurality of other-end side bent portions each having an apex at said other side of said stent in said axial direction thereof; said apex of each of said one-end side bent portions of each wavy annular member penetrates into a space formed between said adjacent other-end side bent portions of one of said adjacent wavy annular members, and said apex of each of said other-end side bent portions of said each wavy annular member penetrates into a space formed between said adjacent one-end side bent portions of said other of said adjacent wavy annular members; and said apex of said one-end side bent portion of each of said wavy annular members and said apex of said other-end side bent portion of said adjacent wavy annular member curve in an approach direction, thus engaging each other.

Also, the object described above is attained by the following a stent.

A stent comprises a plurality of wavy annular members arranged adjacently to each other in an axial direction thereof, with said adjacent wavy annular members connected with each other, wherein each of said wavy annular members has a plurality of one-end side bent portions each having an apex at one side of said stent in an axial direction thereof and a plurality of other-end side bent portions each having an apex at said other side of said stent in said axial direction thereof an apex of each of said one-end side bent portions of each wavy annular member penetrates into a space formed between said adjacent other-end side bent portions of one of said adjacent wavy annular members, and an apex of each of said other-end side bent portions of said each wavy annular member penetrates into a space formed between said adjacent one-end side bent portions of said other of said adjacent wavy annular members; and said apex of said one-end side bent portion of each of said wavy annular members and said apex of said other-end side bent portion of said adjacent wavy annular member are depressed and engage each other.

DETAILED DESCRIPTION OF THE PREFERRED EMBODIMENTS

One preferred embodiment of the stent of the present invention will be described below with reference to FIGS. 1 through 5.

Figure 1:
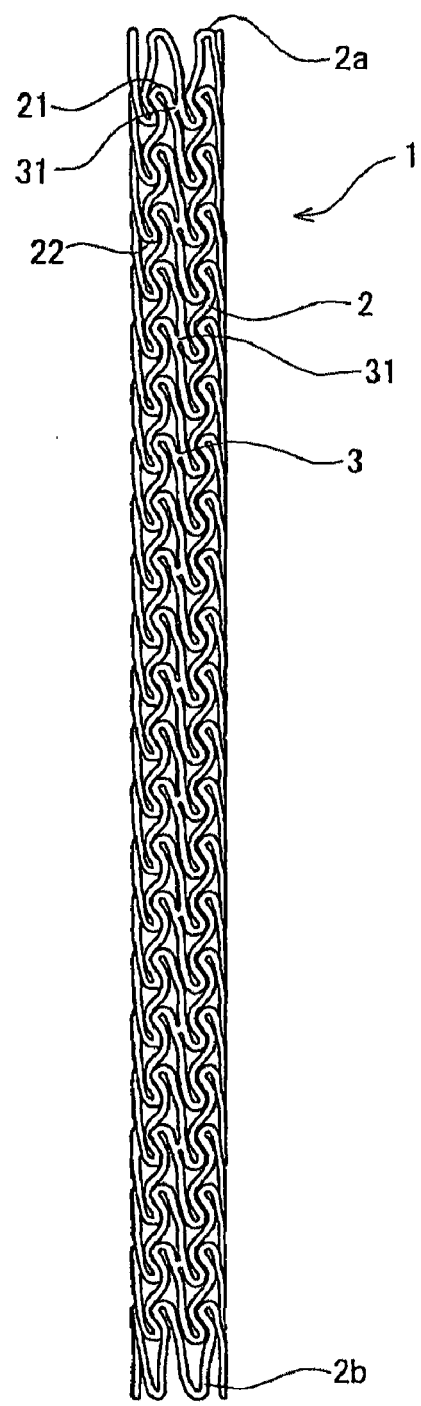
FIG. 1 is a front view showing a stent of one embodiment of the present invention.
Figure 2:
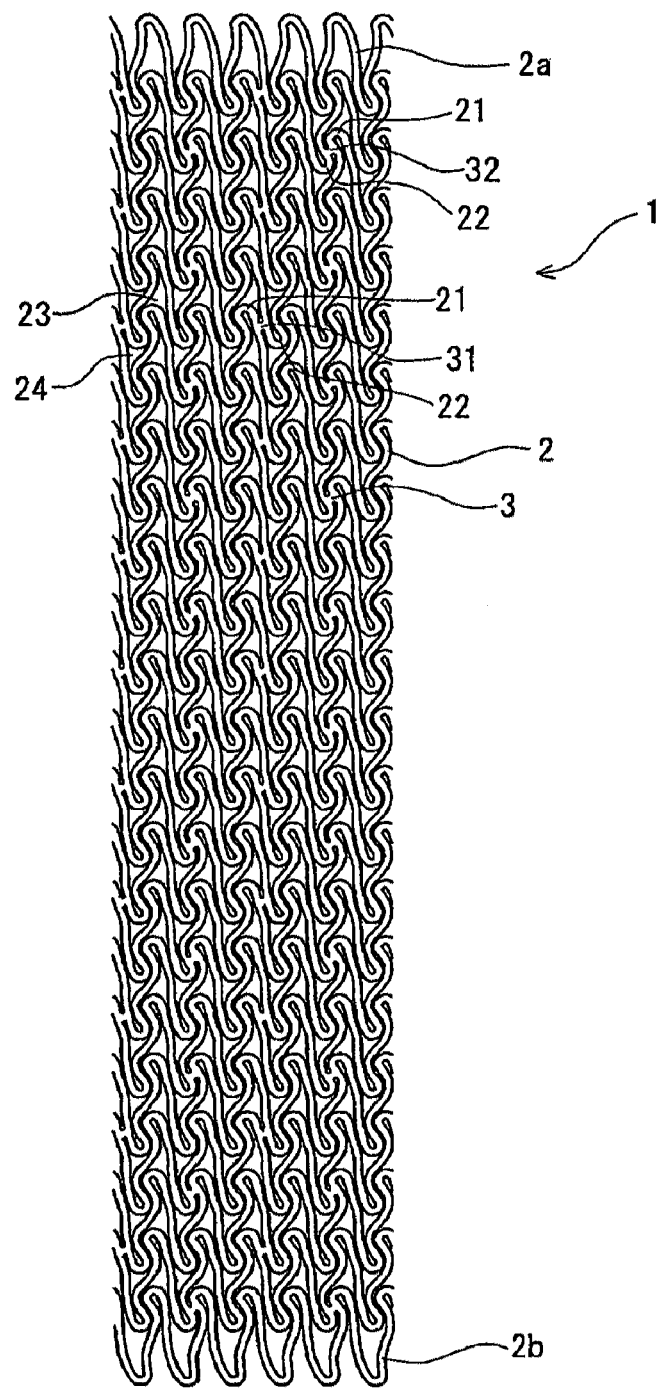
FIG. 2 is a development view showing the stent shown in FIG. 1.
Figure 3:
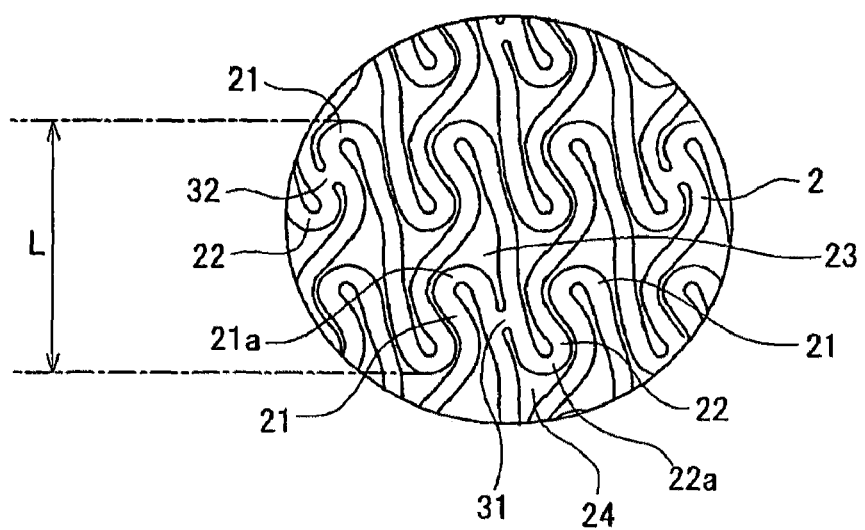
FIG. 3 is a partly enlarged view showing the stent of FIG. 2.
Figure 4:
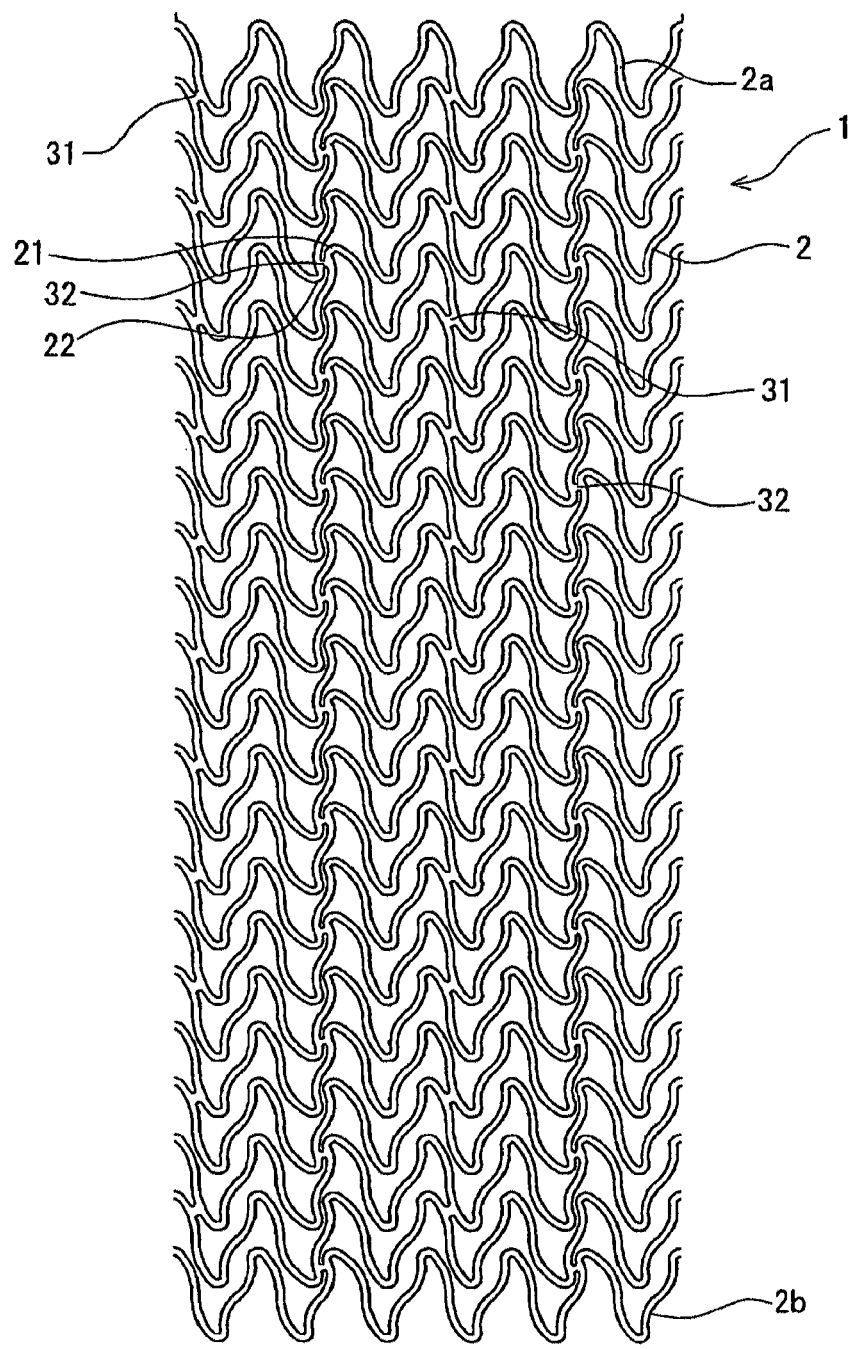
FIG. 4 is a development view showing the stent shown in FIG. 1 immediately after the stent is manufactured.
Figure 5:
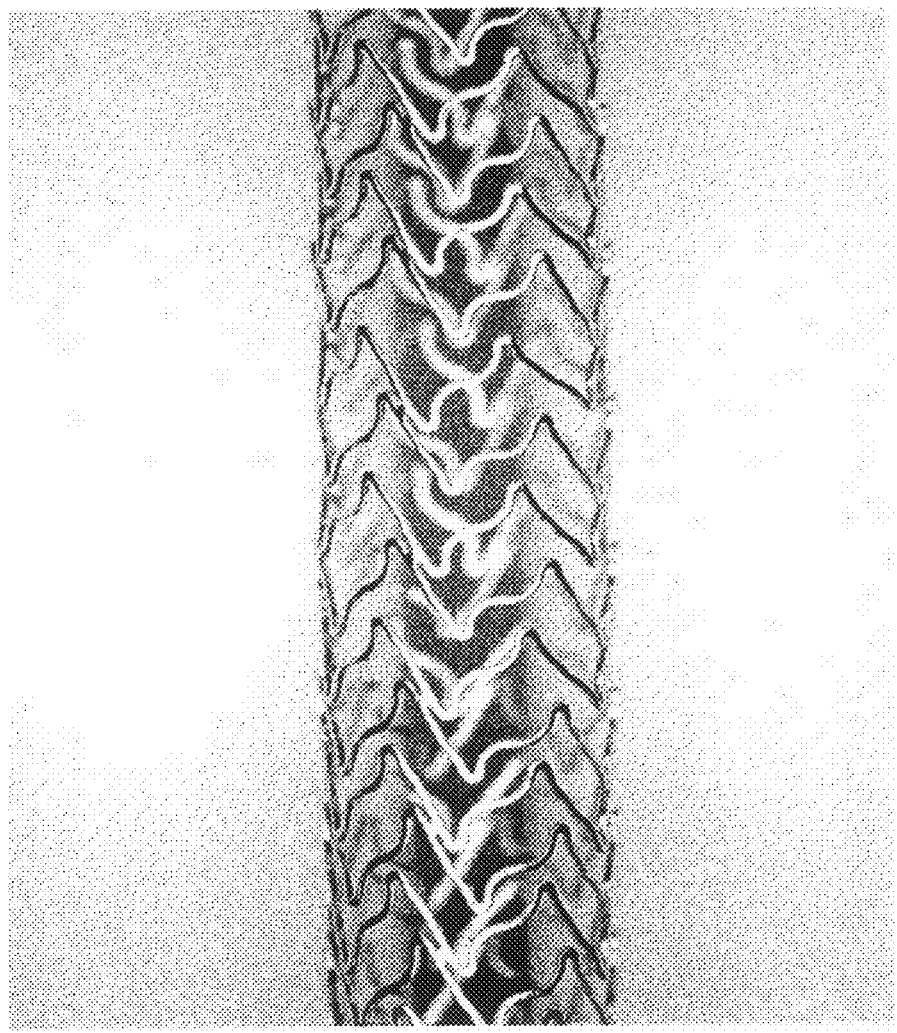
FIG. 5 is an explanatory view for explaining a form of the stent of the embodiment of the present invention when the stent is expanded.

FIG. 1 is a front view showing a stent of one embodiment of the present invention FIG. 2 is a development view showing the stent shown in FIG. 1. FIG. 3 is a partly enlarged view showing the stent of FIG. 2. FIG. 4 is a development view showing the stent shown in FIG. 1 immediately after the stent is manufactured. FIG. 5 is an explanatory view for explaining a form of the stent of the embodiment of the present invention when the stent is expanded.

A stent 1 of the present invention has a plurality of wavy annular members 2 arranged adjacently to each other in an axial direction thereof, with the adjacent wavy annular members 2 connected with each other. Each of the wavy annular members 2 has a plurality of one-end side bent portions 21 each having an apex at one-end side of the stent 1 in an axial direction thereof and a plurality of other-end side bent portions 22 each having an apex at the other-end side of the stent 1 in the axial direction thereof. An apex 21a of each of the one-end side bent portions 21 of each wavy annular member 2 penetrates into a space 23 formed between the adjacent other-end side bent portions 22 of one of the adjacent wavy annular members 2. An apex 22a of each of the other-end side bent portions 22 of each wavy annular member 2 penetrates into a space 24 formed between the adjacent one-end side bent portions 21 of the other of the adjacent wavy annular members 2. The apex 21a of the one-end side bent portion 21 of each of the wavy annular members 2 and the apex 22a of the other-end side bent portion 22 of the adjacent wavy annular member 2 curve in an approach direction thus engaging each other.

The stent 1 is formed substantially as a tube and has a diameter whose dimension is so set that it can be inserted into a lumen of a predetermined portion inside an organism. The stent 1 can be expanded when a force spreading radially outward from the inside of the tube is applied thereto. The stent 1 is a so-called balloon expandable stent.

As shown in FIGS. 1 and 2, the stent 1 of the present invention has a plurality of the wavy annular members 2 arranged adjacently to each other in the axial direction thereof, with the adjacent wavy annular members connected with each other.

The number of the wavy annular members 2 forming the stent 1 shown in FIG. 1 is set to 23. The number of the wavy annular members 2 is favorably in the range of 4 to 50 and more favorably in the range of 10 to 35, although the number thereof is different in dependence on the length of the stent.

Each of the wavy annular members 2 has a plurality of one-end side bent portions 21 each having an apex at one-end side of the stent 1 in an axial direction thereof and a plurality of other-end side bent portions 22 each having an apex at the other-end side of the stent 1 in the axial direction thereof. Each of the wavy annular members 2 is composed of a large number of endless wavy line elements. The one-end side bent portions 21 and the other-end side bent portions 22 are formed alternately. The number of the one-end side bent portions 21 and that of the other-end side bent portions 22 are equal to each other. The number of the one-end side bent portions 21 (the other-end side bent portions 22) of each of the wavy annular members 2 shown in FIG. 1 is set to six. The number of the one-end side bent portions 21 (the other-end side bent portions 22) is favorably in the range of 4 to 12 and more favorably in the range of six to eight. The wavy line element composing the wavy annular member 2 of the stent 1 of this embodiment curves and does not have a straight-line portion substantially. Therefore the wavy line element forming the annular member 2 has a sufficiently large length and displays a high expansive force when it expands. Particularly in the annular member 2 forming the stent 1 of this embodiment a stratum portion of the stent 1 connecting the apexes 21a and 22a to each other is composed of a short S-shaped portion and a long S-shaped portion inclining toward the short S-shaped portion. The apexes 21a and 22a connect the two S-shaped portions to each other.

The length of the wavy annular member 2 in its axial direction is favorably in the range of 0.5 to 2.0 mm and more favorably in the range of 0.9 to 1.5 mm.

A bent portion 2a disposed at one end of the wavy annular member 2 disposed at one end of the stent 1 and a bent portion 2b disposed at the other end of the wavy annular member 2 disposed at the other end of the stent 1 curve more widely than the other bent portions (one-end side bent portion 21 and other-end side bent portion 22). Thereby the stent 1 is allowed to increase the expansive force at both ends thereof, when the stent 1 expands.

As shown in FIGS. 2 and 3, the apex 21a of each of the one-end side bent portions 21 of each wavy annular member 2 penetrates into the space 23 formed between the adjacent other-end side bent portions 22 of one of the adjacent wavy annular members 2. Similarly the apex 22a of each of the other-end side bent portions 22 of each wavy annular member 2 penetrates into the space 24 formed between the adjacent one-end side bent portions 21 of the other of the adjacent wavy annular members 2. That is, the adjacent wavy annular members 2 overlap each other in the axial direction of the stent 1. The axial length of the overlapped portion (in other words, engaging portion which will be described later) of the wavy annular member 2 is favorably not less than 0.2 mm, more favorably not less than 0.2 mm nor more than 0.8 mm, and most favorably not less than 0.3 mm nor more than 0.6 mm. The axial distance (when the stent is mounted on a balloon, which will be described later) between proximate apexes of the adjacent wavy annular members is favorably not less than 0.2 mm, more favorably not less than 0.2 mm nor more than 0.8 mm, and most favorably not less than 0.3 mm nor more than 0.6 mm.

The apex 21a of the one-end side bent portion 21 of each of the wavy annular members 2 and the apex 22a of the other-end side bent portion of the adjacent wavy annular member 2 curve in an approach direction, thus engaging each other. More specifically, the one-end side bent portion 21 of the wavy annular member 2 which penetrates into the space formed between the adjacent wavy annular members 2 curves in the circumferential direction of the stent 1, whereas the other-end side bent portion 22 engaging the one-end side bent portion 21 curves in a direction opposite to the direction in which the one-end side bent portion 21 curves. Thus the one-end side bent portion 21 and the other-end side bent portion 22 curve in the approach direction. Because the apex 21a of the one-end side bent portion 21 and the apex 22a of the other-end side bent portion 22 engage each other, the stent 1 displays a high expansion retention force when it expands. When the stent 1 is bent at a bent portion of a blood vessel, it is possible to prevent the apexes from colliding with each other. Thereby the stent 1 displays a high flexibility.

The adjacent wavy annular members 2 are connected to each other by a short connection portion 3. The stent 1 of this embodiment has the connection portion 3 disposed toward one or other-end side of the stent 1 to some extent in the axial direction thereof with respect to the apex 21a of the one-end side bent portion 21 of the wavy annular member 2 and with respect to the apex 22a of the other-end side bent portion 22 of the adjacent wavy annular member 2. In other words, the connection portion 3 is shifted to some extent from the apexes 21a and 22a of the one-end side bent portion 21 and the other-end side bent portion 22. In other words, the connection portion 3 is shifted toward the one or other end of the stent with respect to the apexes 21a and 22a of the one-end side bent portion 21 and the other-end side bent portion 22.

Therefore it is possible to decrease the degree of contraction (shortening) of the whole length of the stent when the stent expands. The apexes of the adjacent bent portions do not face each other but nest each other. Therefore when the stent bends at the bent portion of the blood vessel the stent passes through the bent portion of the blood vessel with a high flexibility without the apexes colliding with each other. Because the connection portion is formed at the position shifted from the apexes, the stent is allowed to expand uniformly and keep its strength in a favorable balance. When the apexes are connected with each other by the connection portion, there is a difference in strength between the bent portion where the connection portion is present and the bent portion where the connection portion is not present. Consequently there is a possibility that the expanded states of the bent portions become nonuniform and that there occurs a nonuniform distribution of strength in the entire stent.

In the stent 1 of this embodiment the connection portion 3 is formed as an oppositional portion connection type connection portion (in other words, connection portion connecting outer sides of proximate bent portions) 31 formed at a rear portion (in other words, a portion where the bent portions 21a and 22a curve in opposite directions, and in other words, outer portions of proximate bent portions) of the portion where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other. By forming the connection portion at the position, in the vicinity of the one-end side bent portion 21 and the other-end side bent portion 22, at which the bent portions 21a and 22a curve in opposite directions, the apexes 21a and 22a are not prevented from opening when the stent expands.

In addition to the oppositional portion connection type connection portion 31, the stent 1 of this embodiment has a engaging position connection type connection portion 32 formed at the position where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other. The engaging position connection type connection portion 32 connects the inner sides of the proximate bent portions with each other. Thus the engaging position connection type connection portion can be said as a connection portion of connecting the inner sides of the proximate bent portions with each other. By forming the connection portion at the position where the apexes 21a and 22a engage each other, the apexes 21a and 22a engage each other firmly. Thereby it is possible to hold the stent on the balloon at a high holding force and prevent the stent from being removed from the balloon when it is delivered.

As apparent from the above description, the stent 1 of this embodiment has both types of connection portions, namely, a first connection portion (oppositional portion connection type connection portion) 31 and a second connection portion (engaging position connection type connection portion) 32. The first connection portion (oppositional portion connection type connection portion) 31 is formed at the position on the rear of the portion where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other. The second connection portion (engaging position connection type connection portion) 32 is formed at the position where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other.

In the stent 1 of this embodiment an annular unit composed of two wavy annular members 2 connected with each other by the first connection portion (oppositional portion connection type connection portion) 31 is connected with an adjacent annular unit by the second connection portion (engaging position connection type connection portion) 32. That is, the first connection portion 31 and the second connection portion 32 are alternately formed in the axial direction of the stent 1. In the stent 1 of this embodiment two first connection portions (oppositional portion connection type connection portion) 31 are formed for one wavy annular member, with the first connection portions 31 substantially opposed to each other with respect to the axis of the stent 1. The first connection portions (oppositional portion connection type connection portions) 31 are disposed linearly in the axial direction of the stent 1. Similarly in the stent 1 of this embodiment two second connection portions (engaging position connection type connection portion) 32 are formed for one wavy annular member, with the second connection portions 32 substantially opposed to each other with respect to the axis of the stent 1. The second connection portions (engaging position connection type connection portions) 32 are uncontinuously and linearly formed in the axial direction of the stent 1. The two first connection portions 31 of the wavy annular member 2 and the two second connection portions 32 of the adjacent wavy annular member 2 are substantially equiangularly disposed with respect to the axis of the stent 1. That is, in the stent 1, the adjacent wavy annular members 2 are connected to each other by the first connection portion 31 or the second connection portion 32, with the first connection portion 31 and the second connection portion 32 arranged alternately in the axial direction of the stent 1. In the stent 1, the adjacent wavy annular members 2 are connected to each other by a plurality of the first connection portions 31 or a plurality of the second connection portions 32, with the first connection portions 31 and the second connection portions 32 arranged alternately in the axial direction of the stent 1.

The connection portion 3 is short and inclines at a predetermined angle with respect to the axial direction of the stent 1. Therefore the stent has few connection portions which little contribute to the expanded state retention force when the stent expands, thus displaying a high expanded state retention force.

The angle formed between the first connection portion 31 and the axis of the stent 1 is different from the angle formed between the second connection portion 32 and the axis thereof. If the inclination angle of the first connection portion 31 and that of the second connection portion 32 are equal to each other, there is a possibility that a disadvantageous bending mode (disadvantageous directionality of bending) is generated when the stent bends. That is, there is a possibility that the stent bends easily in one bending direction and does not bend easily in other bending direction. The inclination angle of the first connection portion 31 and that of the second connection portion 32 are differentiated from each other to allow the stent to bend uniformly in all directions.

The stent 1 is formed in a state as shown in FIG. 4 which is a developed view. The stent 1 has a larger outer diameter in the state shown in FIG. 4 than in the state shown in FIGS. 1 and 2. Thereafter the stent 1 is mounted on an expandable balloon of an organism expansion appliance by reducing the outer diameter of the stent 1. By expanding the balloon, the outer diameter of the stent 1 is extended larger than that at the time when the stent 1 has the state as shown in FIG. 4. FIG. 5 shows a state in which the outer diameter of the stent 1 is increased. Even in the state in which the outer diameter of the stent 1 is increased, each wavy annular member maintains its fundamental skeleton and the bent portions keep inside the space formed between the adjacent bent portions of the adjacent wavy annular member. The wavy line element constituting the annular member deforms but keeps wavy. In the stent of this embodiment the apexes of the adjacent annular members are disposed nonlinearly to the axis of the stent 1. The apertures of the bent portions are substantially identical to each other in the configurations thereof and are substantially equal to each other in the areas thereof. Because the stent 1 of this embodiment has the above-described form when it expands, the stent 1 displays a high expanded state retention force. Further after the stent expands, the bent portions remain bent to some extent in the circumferential direction of the stent 1. Thus the apexes hardly flare outward.

Figure 6:
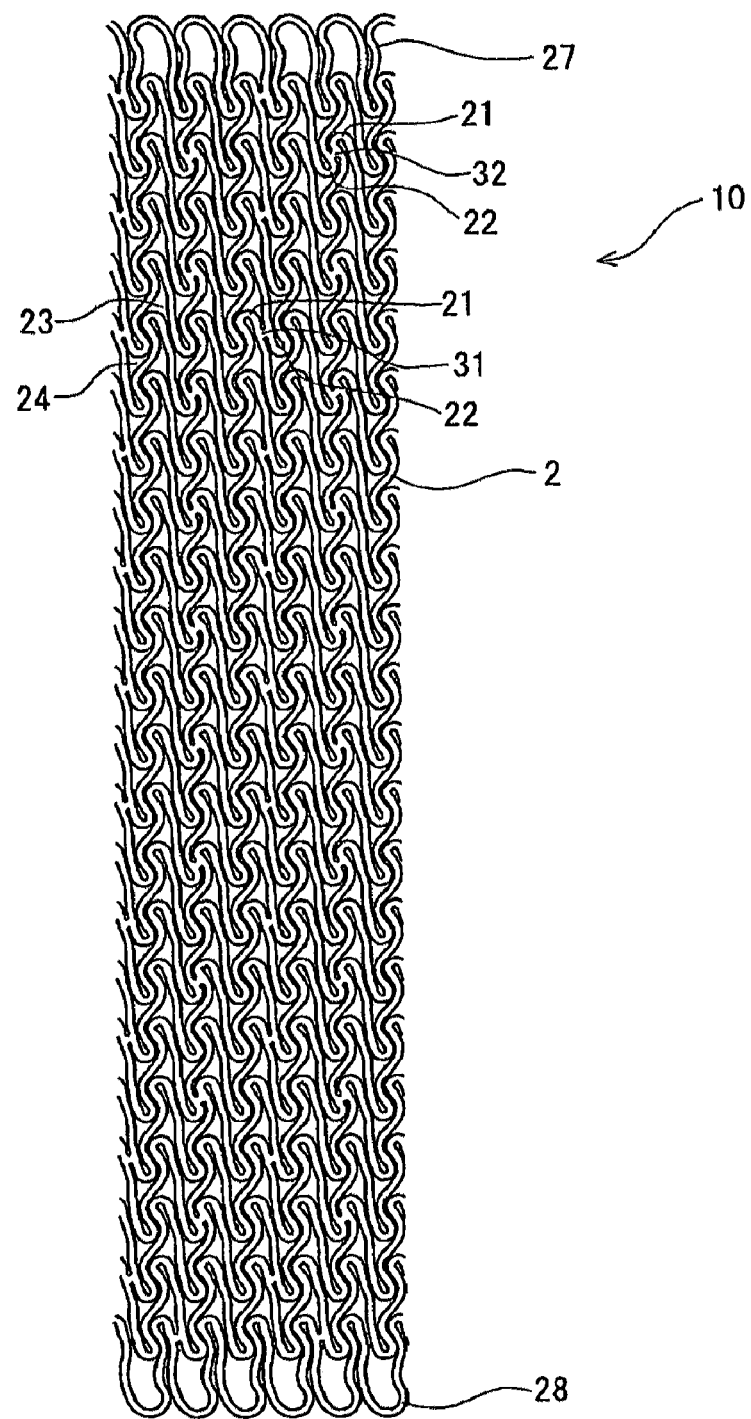
FIG. 6 is a development view showing a stent of another embodiment of the present invention.
Figure 7:
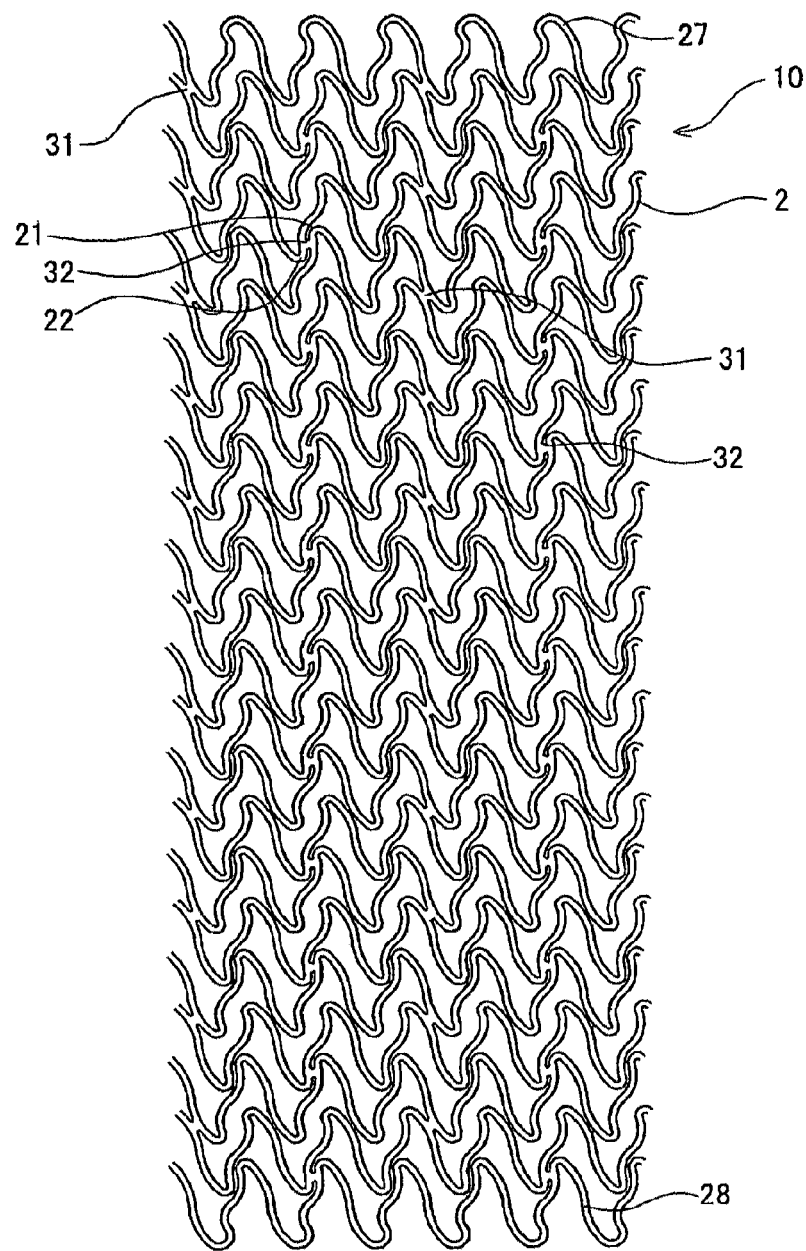
FIG. 7 is a development view showing the stent shown in FIG. 6 immediately after the stent is manufactured.

The bent portion 2a disposed at one end of the wavy annular member 2 disposed at one end of the stent 1 and the bent portion 2b disposed at the other end of the wavy annular member 2 disposed at the other end of the stent 1 may be formed as shown in FIGS. 6 and 7. FIG. 6 is a development view showing a stent of another embodiment of the present invention. FIG. 7 is a development view showing the stent shown in FIG. 6 immediately after the stent is manufactured. In a stent 10 of this embodiment a bent portion 27 disposed at the one end of the wavy annular member 2 disposed at the one end of the stent 10 and a bent portion 28 disposed at the other end of the wavy annular member 2 disposed at the other end of the stent 10 are open wider than the bent portion 5, 27, 28 of the stent 1. Thereby it is possible to enhance the expansive force of the bent portions 27, 28 when the stent 1 expands.

Figure 8:
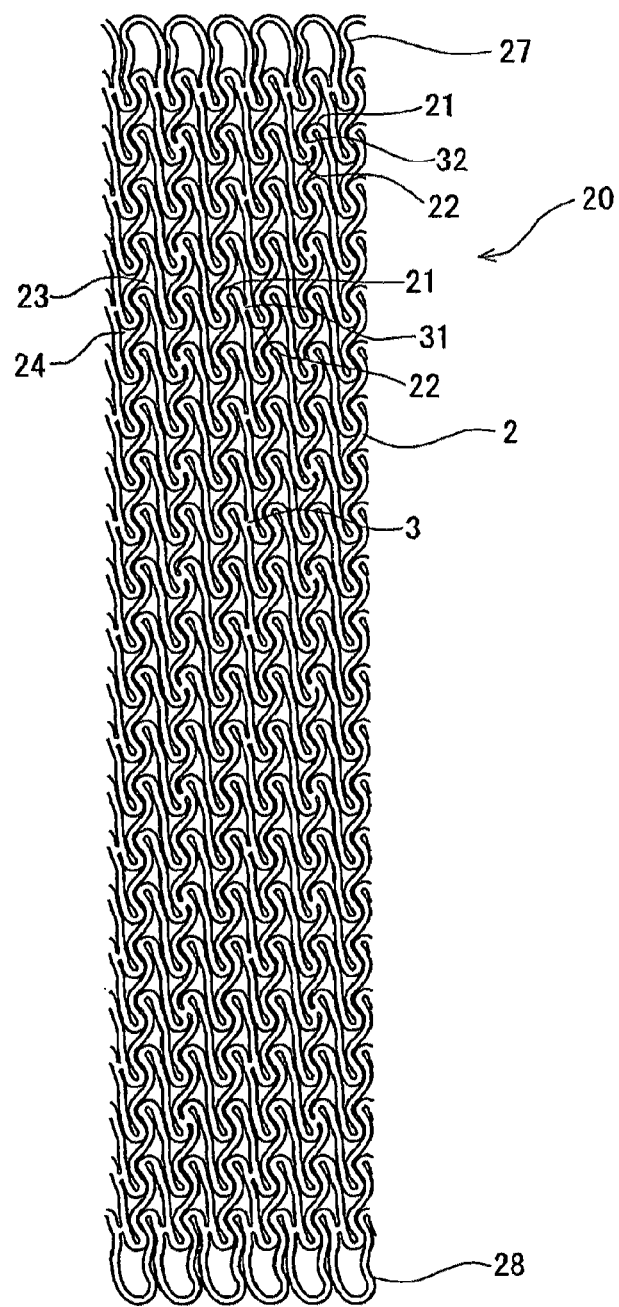
FIG. 8 is a development view showing a stent of another embodiment of the present invention.
Figure 9:
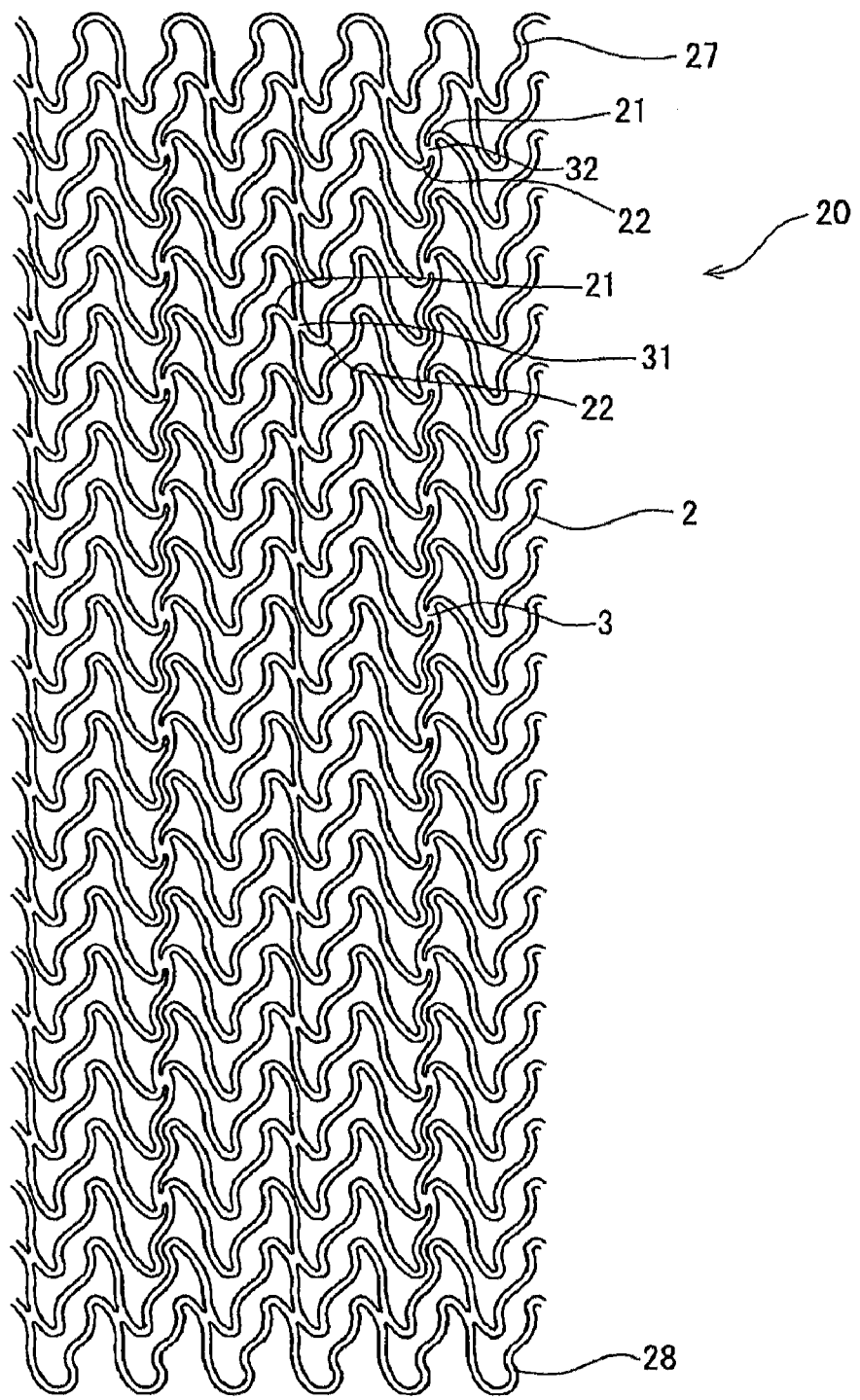
FIG. 9 is a development view showing the stent shown in FIG. 8 immediately after the stent is manufactured.

It is possible to connect the wavy annular member 2 disposed at the one end of the stent 1 and the adjacent wavy annular member to each other by a large number of connection portions. Similarly it is possible to connect the wavy annular member 2 disposed at the other end of the stent 1 and the adjacent wavy annular member to each other by a large number of connection portions. FIG. 8 is a development view showing a stent of another embodiment of the present invention. FIG. 9 is a development view showing the stent shown in FIG. 8 immediately after the stent is manufactured. In a stent 20 of this embodiment the wavy annular member 2 disposed at the one end of the stent 1 and the adjacent wavy annular member 2 are connected with each other at all oppositional portions (outer portions of proximate bent portions) by the first connection portion (oppositional portion connection type connection portion or connection portion connecting outer sides of proximate bent portions) 31. Thus six connection portions 31 are provided for these two adjacent wavy annular members 2. The connection portion (oppositional portion connection type connection portion or connection portion connecting outer sides of proximate bent portions) may be replaced with the engaging position connection type connection portion. Similarly the wavy annular member 2 disposed at the other end of the stent 1 and the adjacent wavy annular member 2 are connected with each other at all oppositional portions (outer portions of proximate bent portions) by the first connection portion (oppositional portion connection type connection portion or connection portion connecting outer sides of proximate bent portions) 31. Thus six connection portions 31 are provided for these adjacent wavy annular members 2. The connection portion (oppositional portion connection type connection portion or connection portion connecting outer sides of proximate bent portions) may be replaced with the engaging position connection type connection portion.

By connecting the wavy annular member 2 disposed at the one end of the stent 1 and the adjacent wavy annular member 2 with each other at all oppositional portions by the first connection portion and by connecting the wavy annular member 2 disposed at the other end of the stent 1 and the adjacent wavy annular member 2 with each other at all oppositional portions by the first connection portion, it is possible to form a small unit (six connection portions in the circumferential direction of the stent) and enhance the strength of the axial ends of the stent. Thereby it is possible to prevent the stent from slipping off the balloon and a dog bone (phenomenon that both ends of the stent begin to expand earlier than other portions thereof in expanding the balloon) from occurring. By uniformly expanding the steno it is possible to minimize damage to be given to a blood vessel.

Figure 10:
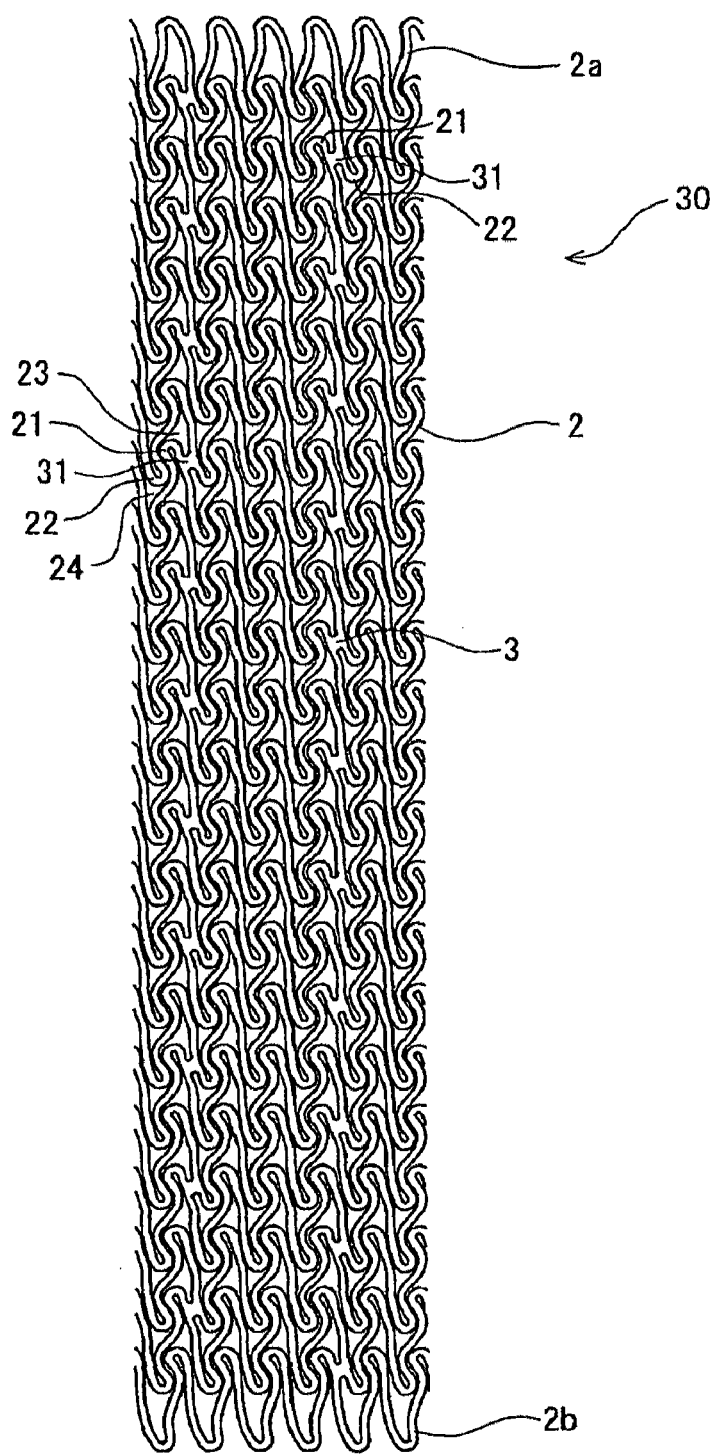
FIG. 10 is a development view showing a stent of another embodiment of the present invention.
Figure 11:
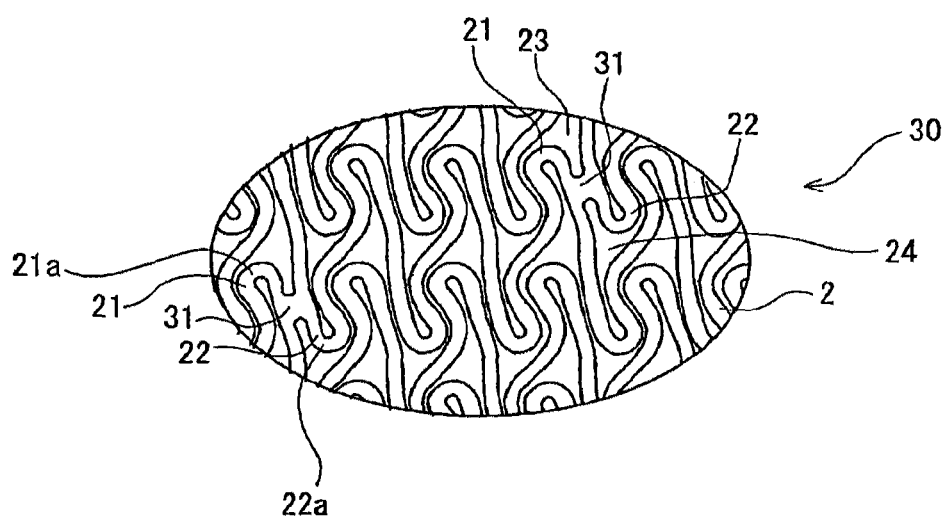
FIG. 11 is a partly enlarged view of the stent of FIG. 10.
Figure 12:
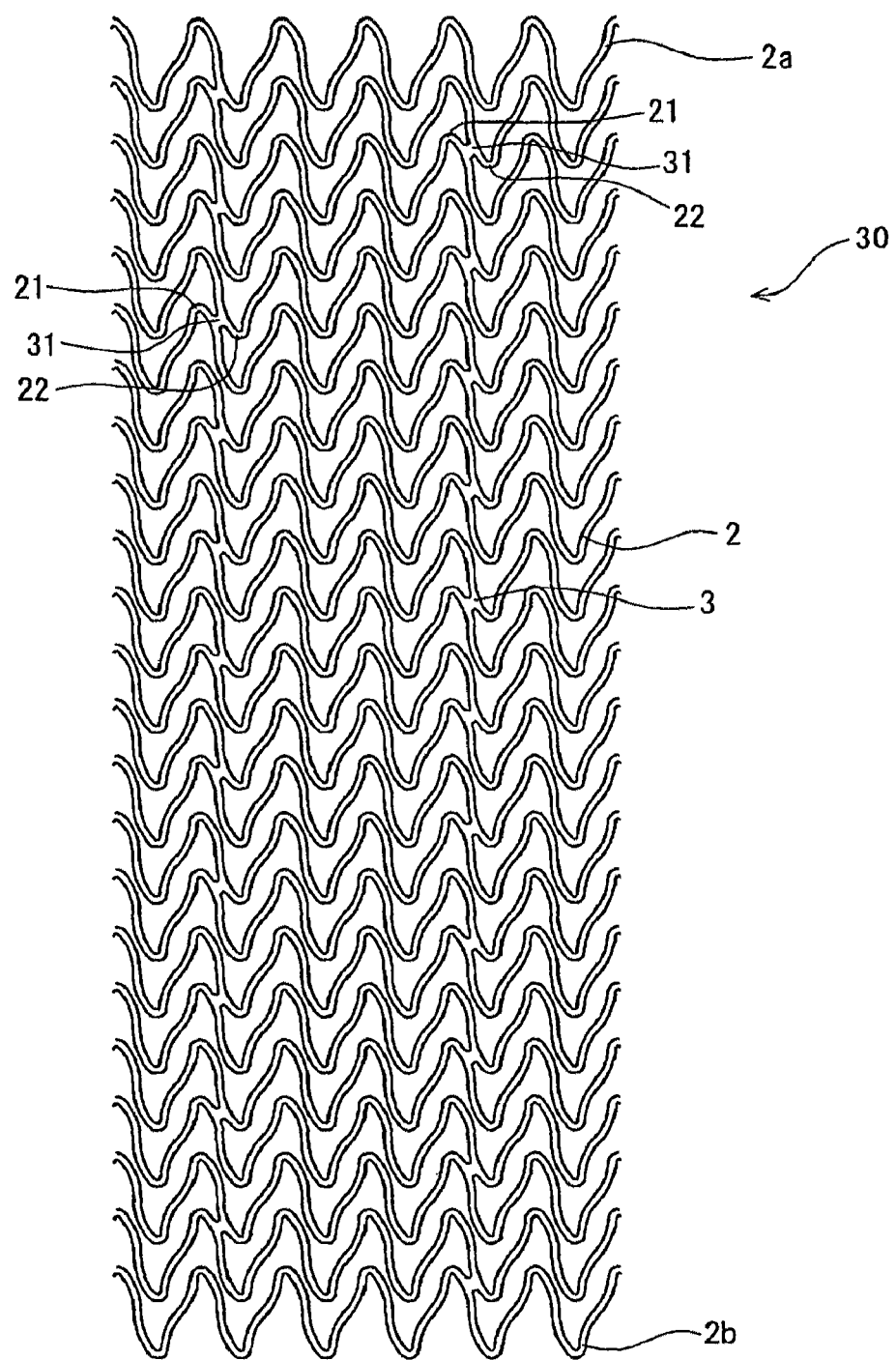
FIG. 12 is a development view showing the stent shown in FIG. 10 immediately after the stent is manufactured.

The stent of the present invention may be formed as a stent 30 having a construction as shown in FIGS. 10 through 12. FIG. 10 is a development view showing a stent of another embodiment of the present invention. FIG. 11 is a partly enlarged view of the stent of FIG. 10. FIG. 12 is a development view showing the stent shown in FIG. 10 immediately after the stent is manufactured.

The stent 30 has the same construction as that of the stent 1 except that the arrangement mode of the connection portion 3 of the stent 30 is different from that of the connection portion of the stent 1. As shown in FIGS. 10 through 12, the adjacent wavy annular members 2 are connected with each other with the oppositional portion connection type connection portion (connection portion connecting outer sides of proximate bent portions) 31. More specifically, the adjacent wavy annular members 2 are connected with each other by one oppositional portion connection type connection portion 31. The connection portions 31 are arranged linearly in two rows in the axial direction of the stent 30 without disposing them continuously. The two rows formed by the connection portions 31 are substantially opposed to each other with respect to the axis of the stent 30. More specifically, the connection portions 31 alternately connect the wavy annular members adjacent to each other in the axial direction of the stent 1. The connection portions 31 are arranged linearly in the axial direction of the stent 1 to form a first row. The stent 30 has the connection portions 31 connecting the adjacent wavy annular members 2 not connected by the connection portions forming the first row. These connection portions 31 also alternately connect the wavy annular members adjacent to each other in the axial direction of the stent 1. The connection portions 31 are arranged linearly in the axial direction of the stent 1 to form a second row. The two rows formed by these two groups of the connection portions 31 are substantially opposed to each other with respect to the axis of the stent 30. The connection portions 31 of the first row and those of the second row are arranged alternately in the axial direction of the stent 30.

The connection portions arranged in the above-described manner eliminates a possibility that the stent bends nonuniformly, namely, a possibility that the stent bends easily in one bending direction and does not bend easily in other bending directions. That is, these connection portions arranged in the above-described manner allow the stent to bend uniformly in all directions.

Figure 13:
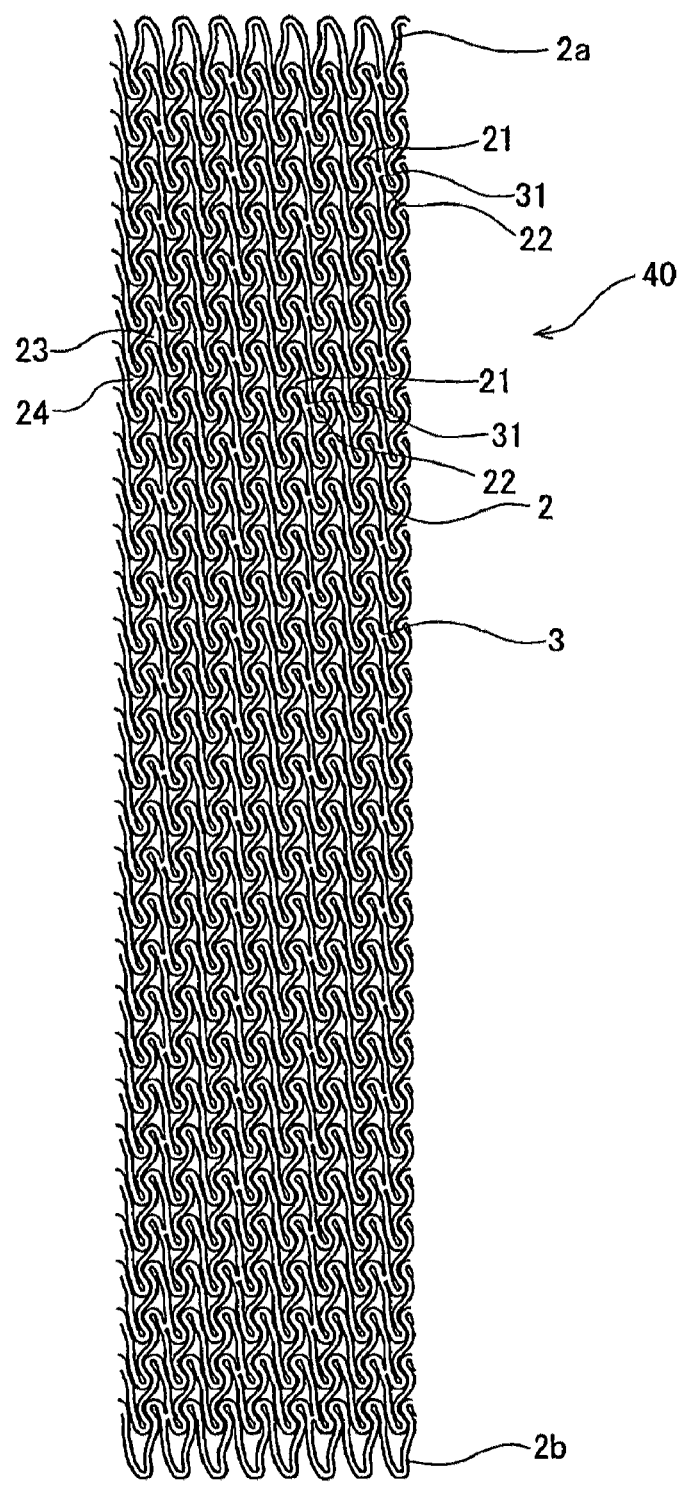
FIG. 13 is a development view showing a stent of another embodiment of the present invention.
Figure 14:
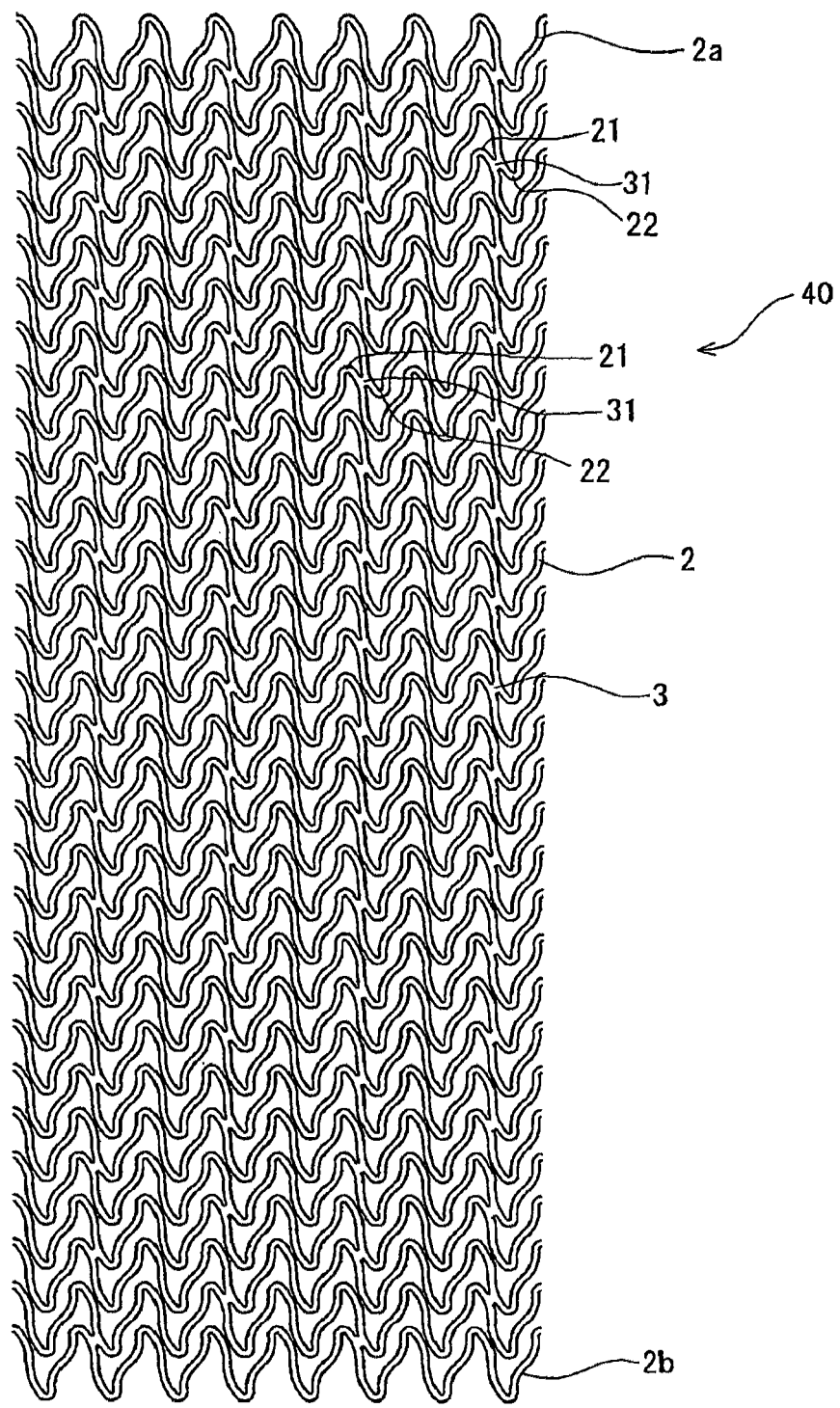
FIG. 14 is a development view showing the stent shown in FIG. 13 immediately after the stent is manufactured.

The stent of the present invention may be formed as a stent 40 having a construction as shown in FIGS. 13 and 14. FIG. 13 is a development view showing a stent of another embodiment of the present invention. FIG. 14 is a development view showing the stent shown in FIG. 13 immediately after the stent is manufactured.

The stent 40 has the same construction as that of the stent 1 except the number of the wavy annular members 2, the number of the one-end side bent portions of one wavy annular member 2 and that of the other-end side bent portions thereof, and the arrangement mode of the connection portion 3. The number of the wavy annular members 2 of the stent 40 is larger than that of the wavy annular members 2 of the stent 1. More specifically, the number of the wavy annular members 2 of the stent 40 is 30. The number (eight) of the one-end side bent portions of one wavy annular member 2 of the stent 40 is larger than that (six) of the one-end side bent portions of one wavy annular member 2 of the stent 1. The number (eight) of the other-end side bent portions of one wavy annular member 2 of the stent 40 is larger than that (six) of the other-end side bent portions of one wavy annular member 2 of the stent 1.

As shown in FIGS. 13 and 14, the adjacent wavy annular members 2 are connected with each other by the oppositional portion connection type connection portions (outer portions of proximate bent portions) 31. The adjacent wavy annular members 2 may be connected with each other by the engaging position connection type connection portion or by a mixture of the oppositional portion connection type connection portion and the engaging position connection type connection portion. The adjacent wavy annular members 2 are connected with each by a plurality of oppositional portion connection type connection portion 31. More specifically, the adjacent wavy annular members 2 are connected with each other by two oppositional portion connection type connection portions 31. The two connection portions 31 connecting the adjacent wavy annular members 2 to each other are substantially opposed to each other with respect to the axis of the stent 40. The connection portions 31 are arranged linearly without disposing them continuously. More specifically, the connection portions 31 alternately connect the wavy annular members 2 adjacent to each other in the axial direction of the stent 40. The connection portions 31 are arranged linearly in the axial direction of the stent 40 to form a first row. The stent 40 has other connection portions arranged linearly in the axial direction thereof to form a second row. The connection portions of the second row are opposed to a fourth row (described below) in the axial direction of the stent 40. The stent 40 has other connection portions connecting the adjacent wavy annular members 2 not connected by the connection portions forming the first row or the second row. These connection portions arranged linearly in the axial direction of the stent 40 alternately connect the wavy annular members adjacent to each other in the axial direction of the stent 40 to form a third row. The stent 40 has other connection portions arranged linearly in the axial direction thereof to form a fourth row. The connection portions forming the fourth row are opposed to the connection portions forming the second row with respect to the axis of the stent 40. The four rows formed by these connection portions 31 are substantially equiangularly disposed with respect to the axis of the stent 40. The connection portions 31 forming the first row and those forming the second row are arranged alternately in the axial direction of the stent 40. Similarly the connection portions 31 forming the third row and those forming the fourth row are arranged alternately in the axial direction of the stent 40.

The connection portions arranged in the above-described manner allow the stent to bend uniformly. By providing the stent with a large number of bent portions, it is possible to increase the distance of the wavy element between the connection portions connecting the adjacent wavy annular members with each other. Thereby the stent displays a high flexibility.

Figure 15:
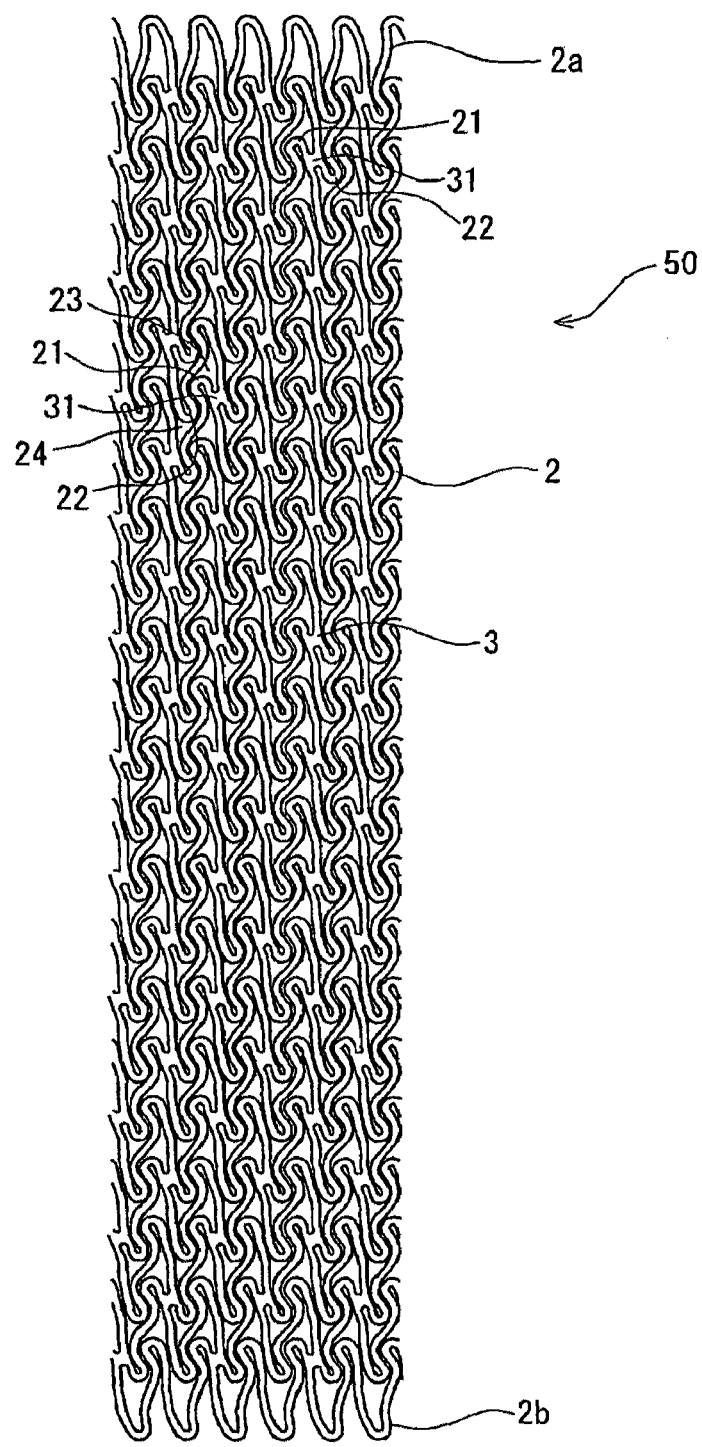
FIG. 15 is a development view showing a stent of another embodiment of the present invention.
Figure 16:
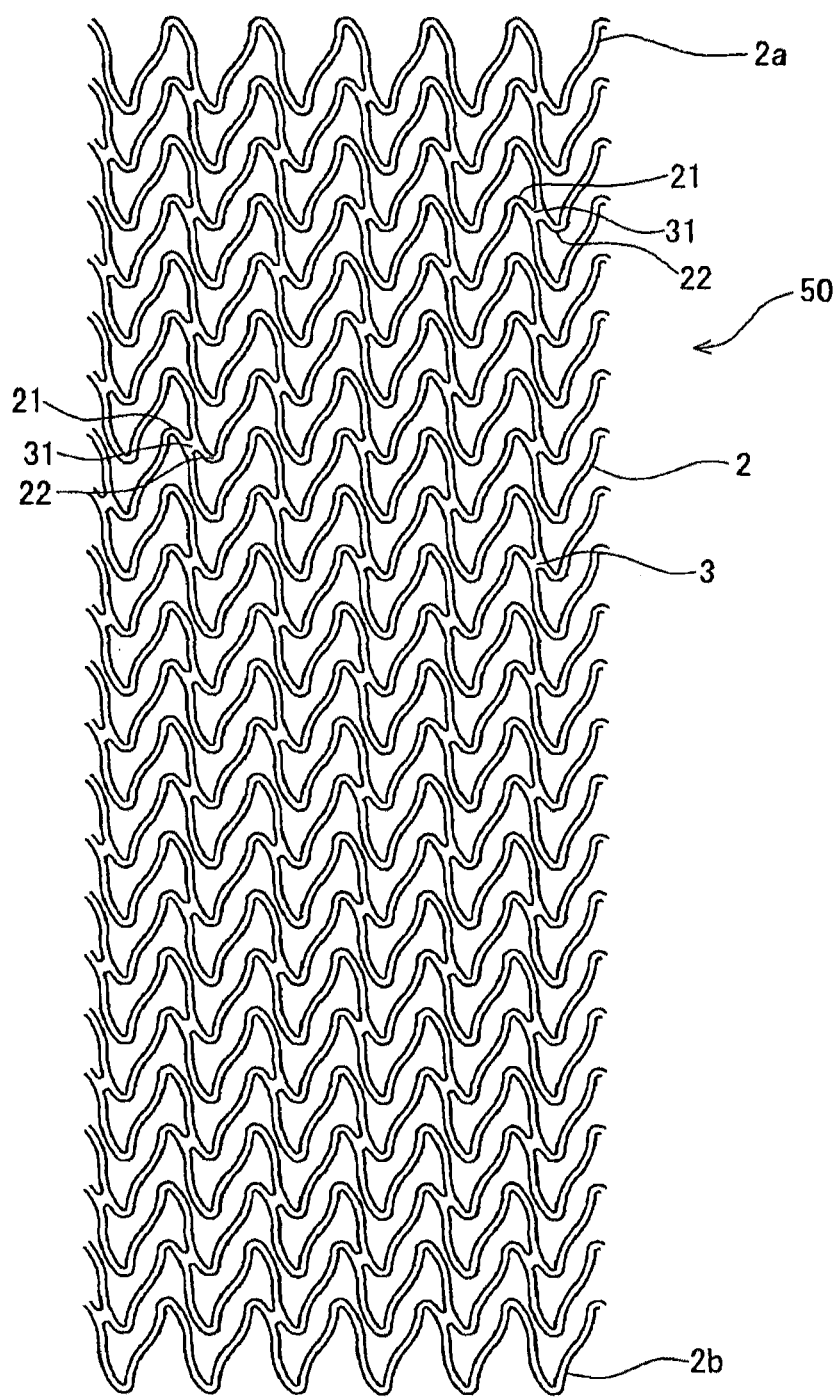
FIG. 16 is a development view showing the stent shown in FIG. 15 immediately after the stent is manufactured.

The stent of the present invention may be formed as a stent 50 having a construction, as shown in FIGS. 15 and 16. FIG. 15 is a development view showing a stent of another embodiment of the present invention. FIG. 16 is a development view showing the stent shown in FIG. 15 immediately after the stent is manufactured.

The stent 50 has the same construction as that of the stent 1 except that the arrangement mode of the connection portion 3 of the stent 50 is different from that of the connection portion 3 of the stent 1. As shown in FIGS. 15 and 16, the adjacent wavy annular members 2 are connected with each other by the oppositional portion connection type connection portion (outer portions of proximate bent portions) 31. The adjacent wavy annular members 2 may be connected with each other by the engaging position connection type connection portion or by a mixture of the oppositional portion connection type connection portion and the engaging position connection type connection portion. More specifically, the adjacent wavy annular members 2 are connected with each other by three oppositional portion connection type connection portions 31. The connection portions 31 are arranged linearly (in other words, like broken line) in six rows without disposing them continuously in the axial direction of the stent 50. The six rows formed by these connection portions are disposed substantially equiangularly with respect to the axis of the stent 50.

More specifically, the connection portions 31 alternately connect the wavy annular members 2 adjacent to each other in the axial direction of the stent 50. The connection portions 31 are arranged linearly in the axial direction of the stent 50 to form a first row. The stent 50 has other connection portions forming second and third rows arranged linearly respectively in the axial direction thereof. The second row and the third row are disposed substantially equiangularly with respect to the axis of the stent 50. The stent 50 has other connection portions, forming a fourth row, which connect the adjacent wavy annular members 2 not connected by the connection portions forming the first row, the second row, and the third row. The connection portions forming the fourth row are also arranged linearly in the axial direction of the stent 50, thus alternately connecting the wavy annular members adjacent to each other in the axial direction of the stent 50. The stent 50 has other connection portions forming fifth and sixth rows arranged linearly in the axial direction thereof respectively. The fifth and sixth rows are disposed substantially equiangularly with respect to the axis of the stent 50. The six rows formed by the connection portions are substantially equiangularly disposed with respect to the axis of the stent 50. The connection portions 31 forming the first second, and third rows and the connection portions 31 forming the fourth, fifth, and sixth rows are arranged alternately in the axial direction of the stent 50.

The connection portions arranged in the above-described manner allow the stent to bent uniformly when the stent expands. Because there is a small free portion between circumferentially adjacent wavy elements, the stent is prevented from expanding freely when the stent expands. Consequently the stent is capable of expanding uniformly. Thereby the stent provides a uniform expansive force and a uniform distribution of a medicine to a blood vessel in coating the blood vessel with the medicine.

A stent of another embodiment of the present invention is described below.

Figure 20:
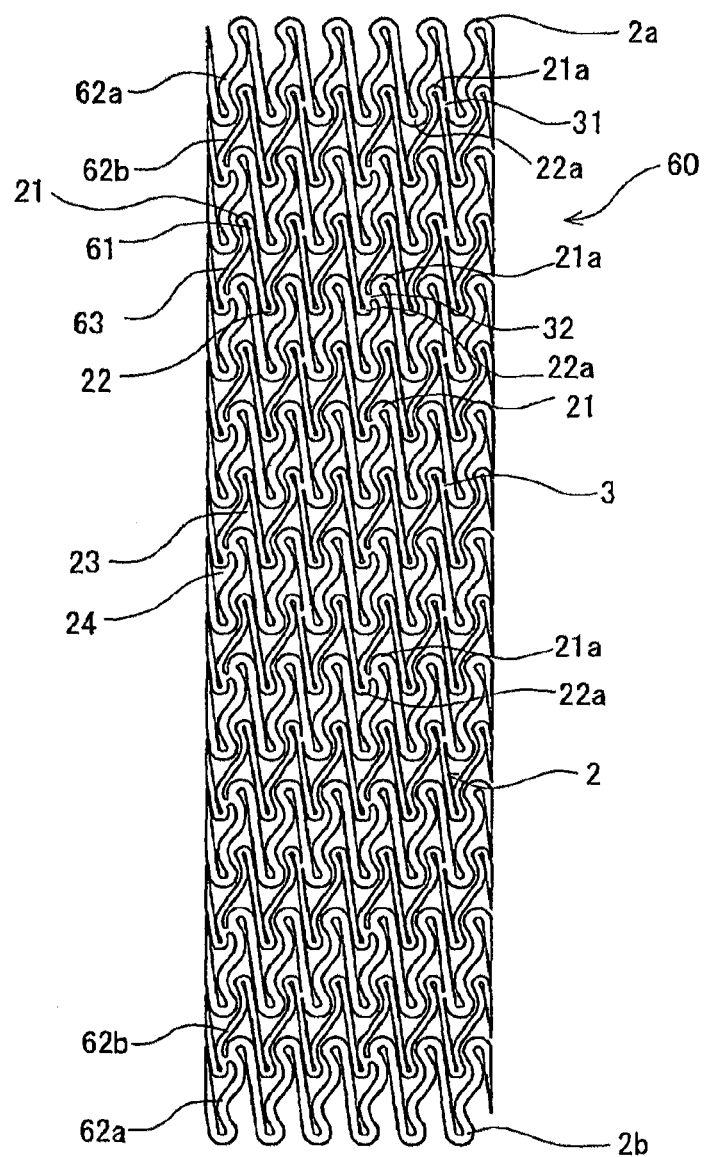
FIG. 20 is a development view showing a stent of another embodiment of the present invention.
Figure 21:
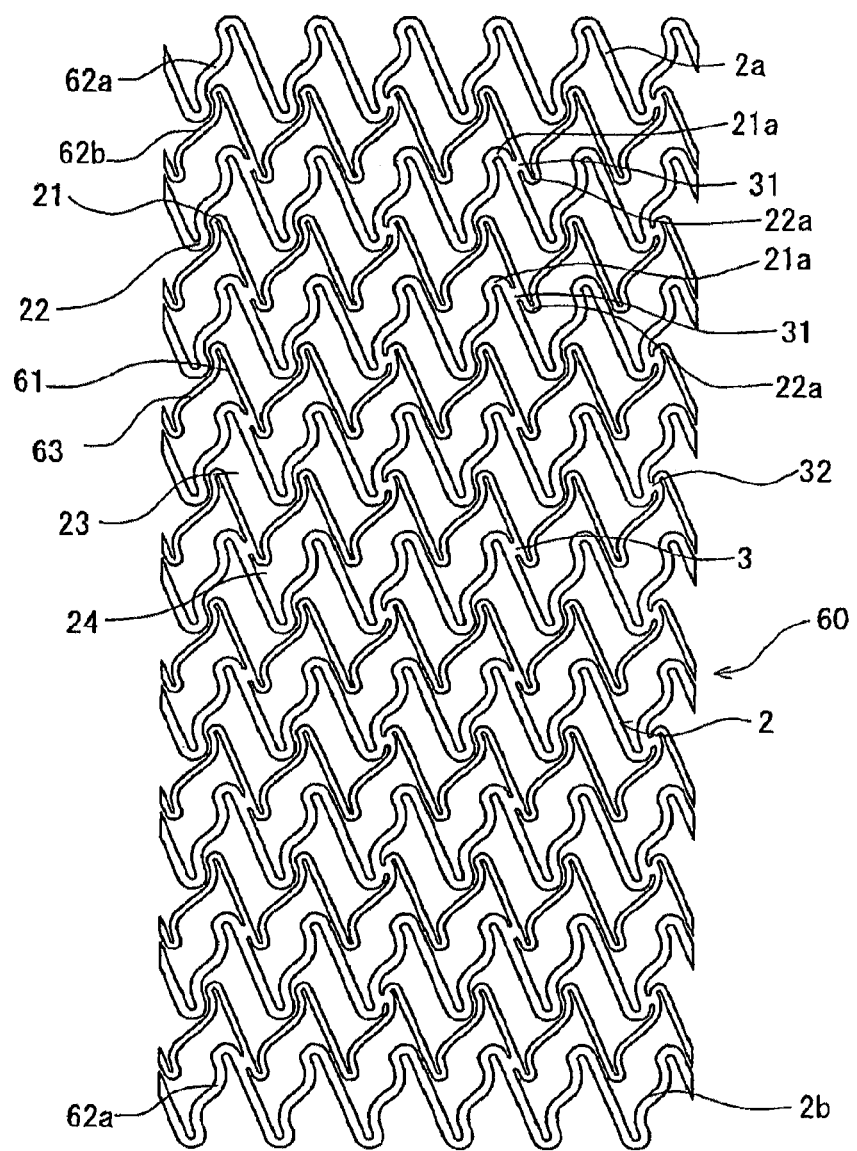
FIG. 21 is a development view showing the stent shown in FIG. 20 immediately after the stent is manufactured.

FIG. 20 is a development view showing a stent of another embodiment of the present invention. FIG. 21 is a development view showing the stent shown in FIG. 20 immediately after the stent is manufactured.

A stent 60 of this embodiment has a plurality of wavy annular members 2 arranged adjacently to each other in an axial direction thereof, with the adjacent wavy annular members 2 connected with each other. Each of the wavy annular members 2 has a plurality of one-end side bent portions 21 each having an apex at one-end side of the stent 1 in an axial direction thereof and a plurality of other-end side bent portions 22 each having an apex at the other-end side of the stent 1 in the axial direction thereof. An apex 21a of each of the one-end side bent portions 21 of each wavy annular member 2 penetrates into a space 23 formed between the adjacent other-end side bent portions 22 of one of the adjacent wavy annular members 2. An apex 22a of each of the other-end side bent portions 22 of each wavy annular member 2 penetrates into a space 24 formed between the adjacent one-end side bent portions 21 of the other of the adjacent wavy annular members 2. The apex 21a of the one-end side bent portion 21 of each of the wavy annular members 2 and the apex 22a of the other-end side bent portion 22 of the adjacent wavy annular member 2 are depressed and engage each other.

The basic construction of the stent 60 has the same construction as that of the above-described stent 1. Only constructions of the stent 60 different from that of the stent 1 are described below.

As shown in FIGS. 20 and 21, the stent 60 has a plurality of the wavy annular members 2 arranged adjacently to each other in the axial direction thereof, with the adjacent wavy annular members connected with each other. In the stent 60, 17 wavy annular members 2 are linearly arranged.

In the stent 60, the wavy annular member 2 is composed of a plurality of straight-line portions 61 extended obliquely at a predetermined angle with respect to the axis of the stent and a plurality of S-shaped curved portions 63 which connects an upper end of one adjacent straight-line portion 61 and a lower end of other adjacent straight-line portion 61 to each other and which is curved in a shape of S. In the stent 60 of this embodiment in a stratum portion connecting the apexes 21a and 22a to each other, each of the apexes 21a and 22a is composed of the straight-line portion 61 and the S-shaped curved portion 63 and connects the straight-line portion 61 and the S-shaped curved portion 63 to each other. Bent portions 2a, 2b disposed at the ends (upper and lower ends) of the wavy annular members 2 disposed at both ends (upper and lower ends) of the stent 60 have the configuration almost the same as that of other bent portions. Similarly to the stent 1, the bent portions 2a, 2b disposed at the ends of the wavy annular members 2 disposed at both ends of the stent 60 may be wide.

Similarly to the stent 1, in the stent 60, the apex 21a of each of the one-end side bent portions 21 of each wavy annular member 2 penetrates into the space 23 formed between the adjacent other-end side bent portions 22 of one of the adjacent wavy annular members 2. Similarly the apex 22a of each of the other-end side bent portions 22 of each wavy annular member 2 penetrates into the space 24 formed between the adjacent one-end side bent portions 21 of the other of the adjacent wavy annular members 2. That is, the adjacent wavy annular members 2 overlap each other in the axial direction of the stent 60.

The apex 21a of the one-end side bent portion 21 of each of the wavy annular members 2 and the apex 22a of the other-end side bent portion 22 of the adjacent wavy annular member 2 are depressed, and engage each other.

The adjacent wavy annular members 2 are connected to each other by a short connection portion 3. The stent 60 of this embodiment has the connection portion 3 disposed between the apex 21a of the one-end side bent portion 21 of the wavy annular member 2 and apex 22a of the other-end side bent portion 22 of the adjacent wavy annular member 2. More specifically, the connection portion 3 is provided in the neighborhood of the middle position between the apex 21a of the one-end side bent portion 21 of the wavy annular member 2 and apex 22a of the other-end side bent portion 22 of the adjacent wavy annular member 2. In other words, the connection portion 3 is formed not at the apexes 21a, 22a of the bent portions 21, 22, but is shifted to some extent from the apexes 21a and 22a of the bent portions 21, 22. In other words, the connection portion 3 is shifted toward the one or other end of the stent with respect to the apexes 21a and 22a of the bent portions 21, 22.

In the stent 60 of this embodiment, the connection portion 3 has a straight-line portion connection type connection portion 31 formed at a rear portion (in other words, straight-line portion 61) of the portion where the apex 21a of the one-end side bent portion 21 of one wavy annular member 2 and the apex 22a of the other-end side bent portion 22 of the adjacent wavy annular member 2 are proximate to each other and engage each other.

The stent 60 of this embodiment has an engaging position connection type connection portion 32 formed at the position where the apex 21a of the one-end side bent portion 21 of one wavy annular member 2 and the apex 22a of the other-end side bent portion 22 of the adjacent wavy annular member 2 engage each other. The expression of the engaging position connection type connection portion can be changed to a portion of connecting the inner side of the engaging portion. The expression of the above-described straight-line portion connection type connection portion 31 can be changed to a portion of connecting the outer side of the engaging portion.

The stent 60 of this embodiment has the connection portions of the two types, namely, the straight-line portion connection type connection portion (portion of connecting the outer side of the engaging portion) 31 and the engaging position connection type connection portion (portion of connecting the inner side of the engaging portion) 32. These connection portions are arranged alternately in the axial direction of the stent 60. Because the connection portions having the different configurations are arranged alternately, the stent has a high expanded state retention force.

Similarly to the stent 1, an annular unit composed of two wavy annular members 2 connected with each other by the first connection portion (straight-line portion connection type connection portion) 31 is connected with an adjacent annular unit by the second connection portion (engaging position connection type connection portion) 32. That is, the first connection portion 31 and the second connection portion 32 are alternately formed in the axial direction of the stent 60. In the stent 60 of this embodiment two first connection portions (oppositional portion connection type connection portion) 31 are formed for one wavy annular member, with the first connection portions 31 substantially opposed to each other with respect to the axis of the stent 60. The first connection portions 31 are disposed linearly in the axial direction of the stent 60. Similarly in the stent 1 of this embodiment two second connection portions 32 are formed for one wavy annular member, with the second connection portions 32 substantially opposed to each other with respect to the axis of the stent 60. The second connection portions 32 are uncontinuously and linearly formed in the axial direction of the stent 60. The two first connection portions 31 of the wavy annular member 2 and the two second connection portions 32 of the adjacent wavy annular member 2 are substantially equiangularly disposed with respect to the axis of the stent 60. The stent 60 has strong and weak portions alternately by connecting the connection portions 31 and 32 alternately.

The connection portion 3 is short and inclines at a predetermined angle with respect to the axial direction of the stent 1. Therefore the stent has few connection portions which little contribute to the expanded state retention force when the stent expands, thus displaying a high expanded state retention force.

As shown in FIGS. 20 and 21, the wavy annular member of the stent 60 has wavy annular members 62a each composed of a wide portion and wavy annular members 62b each composed of a narrow portion. The wavy annular members 62a each composed of the wide portion and the wavy annular members 62b each composed of the narrow portion are arranged alternately. It is preferable that the width of the portion forming the wavy annular member 62b is in the range of ⅓ to ⅔ of the width of the wavy annular member 62a. By reducing the width of the portion forming the wavy annular member 62b arranged alternately with the portion forming the wavy annular member 62a, it is easy to mount the stent on an expandable balloon of an appliance by reducing the diameter of the stent and reduce the outer diameter of the stent when it is mounted on the balloon.

It is preferable that the stent 60 is composed of odd-numbered wavy annular members, that the portions forming the odd-numbered wavy annular members 62a are wide, and that the portions forming the even-numbered wavy annular members 62b are narrow. In this construction, the wavy annular members 62a disposed at both ends (upper and lower ends) of the stent 60 are wide. Thereby both ends of the stent 60 has a sufficient expanded state retention force.

Similarly to the stent 1, the stent 60 having a larger outer diameter than the outer diameter of the stent shown in FIG. 20 is formed as shown in FIG. 21. Thereafter the stent 60 is mounted on the expandable balloon of the appliance by reducing the diameter of the stent. By expanding the balloon, the outer diameter of the stent 60 is made larger than the outer diameter shown in FIG. 21.

Figure 22:
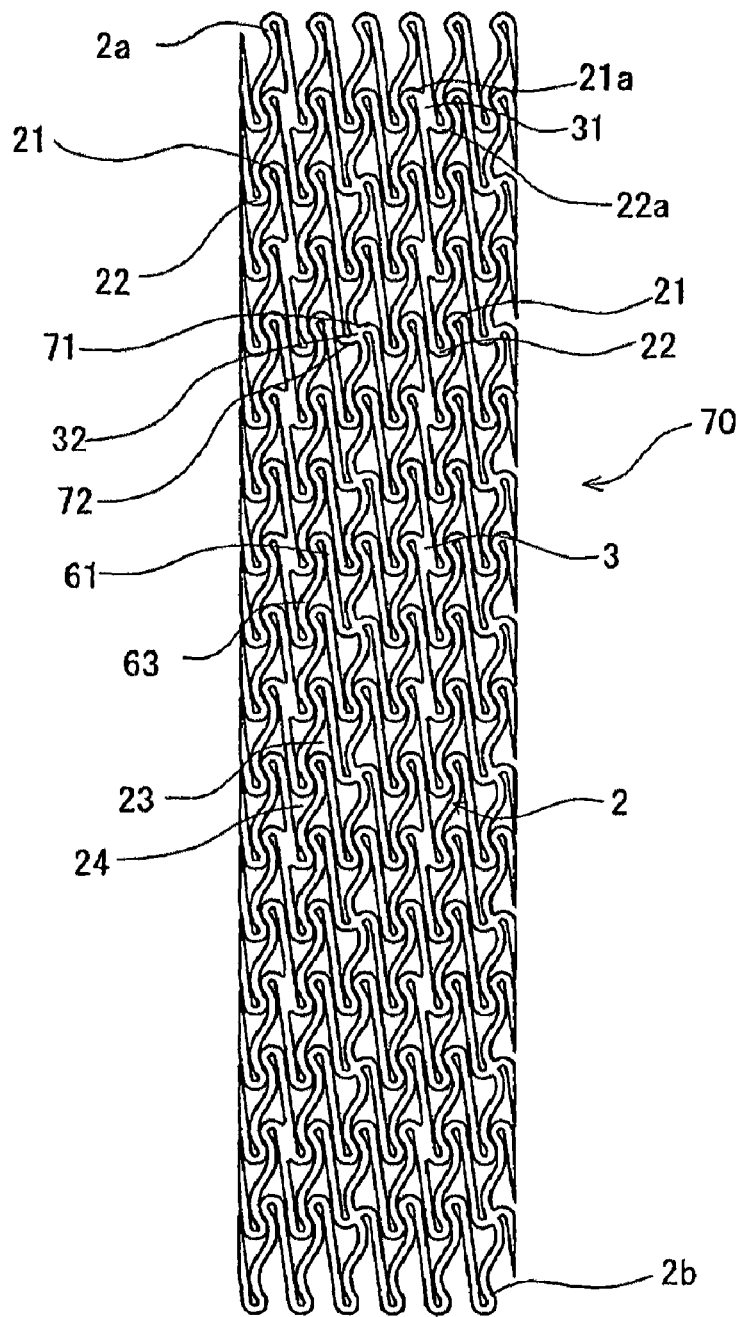
FIG. 22 is a development view showing a stent of another embodiment of the present invention.
Figure 23:
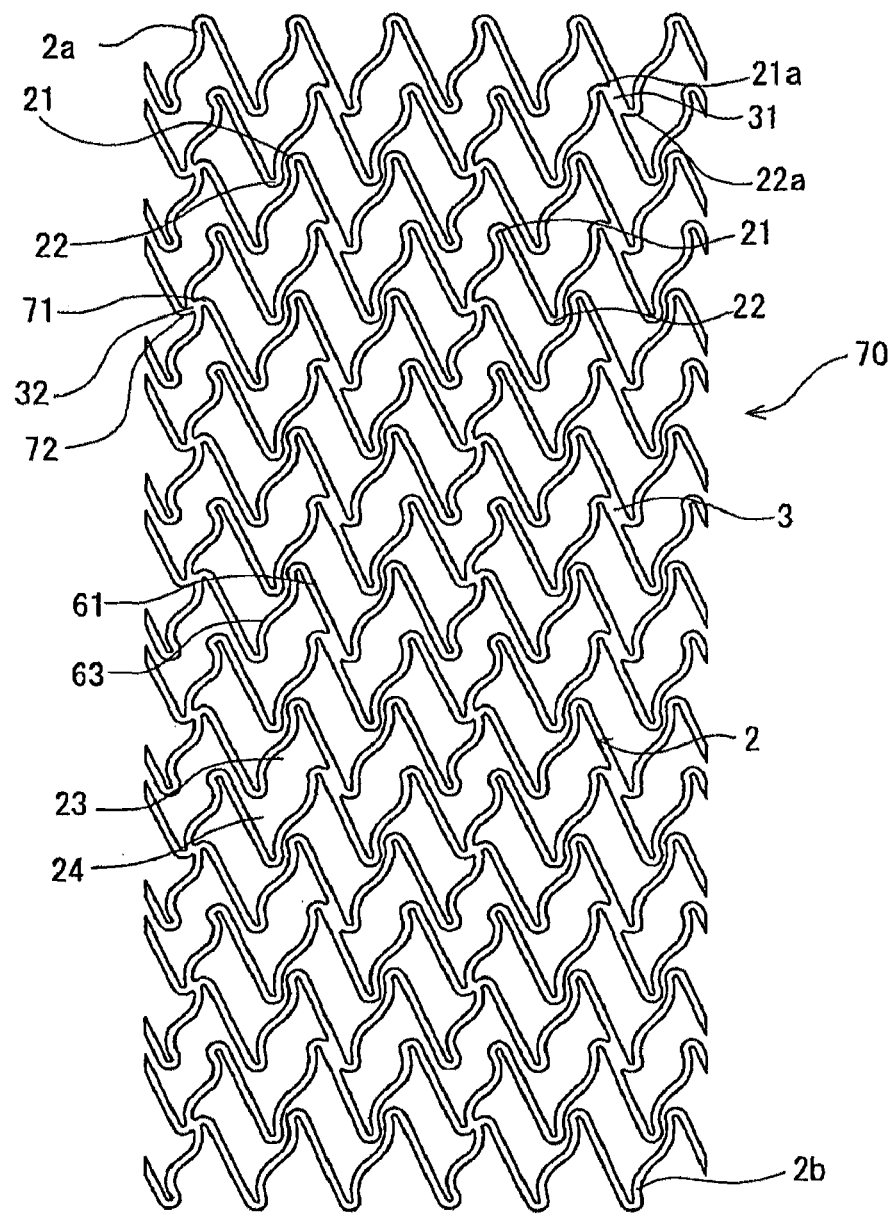
FIG. 23 is a development view showing the stent shown in FIG. 22 immediately after the stent is manufactured.

The form of the stent may have a construction shown in FIGS. 22 and 23.

FIG. 22 is a development view showing a stent of another embodiment of the present invention. FIG. 23 is a development view showing the stent shown in FIG. 22 immediately after the stent is manufactured.

The basic construction of a stent 70 has the same construction as that of the above-described stents 1 and 60. The stent 70 has the same construction as that of the stent 60 except that the widths of the material forming all the wavy annular members 2 are almost equal to each other and that the configuration of the second connection portion 32 is different from that of the connection portion of the stent 60.

As shown in FIGS. 22 and 23, the stent 70 has a plurality of the wavy annular members 2 arranged adjacently to each other in the axial direction thereof, with the adjacent wavy annular members connected with each other. In the stent 70, similarly to the stent 1, the apex 21a of each of the one-end side bent portions 21 of each wavy annular member 2 penetrates into the space 23 formed between the adjacent other-end side bent portions 22 of one of the adjacent wavy annular members 2. Similarly, the apex 22a of each of the other-end side bent portions 22 of each wavy annular member 2 penetrates into the space 24 formed between the adjacent one-end side bent portions 21 of the other of the adjacent wavy annular members 2. That is, the adjacent wavy annular members 2 overlap each other in the axial direction of the stent 70.

In the stent 70, similarly to the stent 60, one wave of the wavy annular member 2 is composed of a plurality of straight-line portions 61 extended obliquely at a predetermined angle with respect to the axis of the stent and a plurality of S-shaped curved portions 63 connected with an upper end of the straight-line portion 61 and curved in a shape of S. The apex 21a of the one-end side bent portion 21 of each of the wavy annular members 2 and the apex 22a of the other-end side bent portion 22 of the adjacent wavy annular member 2 are depressed and engage each other.

In the stent 70 of this embodiment similarly to the stent 60, the connection portion 3 has a straight-line portion connection type connection portion 31 formed at a rear portion (in other words, straight-line portion 61) of the portion where the apex 21a of the one-end side bent portion 21 of one wavy annular member 2 and the apex 22a of the other-end side bent portion 22 of the adjacent wavy annular member 2 are proximate to each other and engage each other. The straight-line portion connection type connection portion 31 of the stent 70 is wider than that of the above-described stent 60. Thus the straight-line portion connection type connection portion 31 can be expressed as a straight-line portion integration portion.

In the stent 70, the apex 72 of the other-end side bent portion 22 of an even-numbered wavy annular member 2 is axially shorter than the apexes of the other other-end side bent portions of the even-numbered wavy annular members 2. The apex 71, proximate to the above-described apex 72, of the one-end side bent portion 21 of an odd-numbered wavy annular member 2 is axially shorter than the apexes of the other one-end side bent portions of the odd-numbered wavy annular members 2. Therefore in the portion proximate to the apexes 71 and 72, the bent portions of the wavy annular member overlap each other in a small amount in the axial direction of the stent 70, thus forming a low engaging portion.

The stent 70 of this embodiment has a low engaging portion connection type connection portion 32 formed at the low engaging portion where the apex 71 of the one-end side bent portion 21 of one wavy annular member 2 and the apex 72 of the other-end side bent portion 22 of the adjacent wavy annular member 2 engage each other. The expression of the low engaging portion connection type connection portion 32 can be changed to a connection portion connecting the inner side of the low engaging portion. The expression of the above-described straight-line portion connection type connection portion 31 can be changed to a connection portion connecting the outer side of the low engaging portion. In the stent 70 of this embodiment, the low engaging portion connection type connection portion 32 may be expressed as a low engaging portion integration portion.

The stent 70 of this embodiment has the connection portions of the two types, namely, the straight-line portion connection type connection portion (portion of connecting the outer side of engaging portion) 31 and the low engaging portion connection type connection portion (portion of connecting inner side of the low engaging portion) 32. These connection portions are arranged alternately in the axial direction of the stent 70. Because the connection portions having the different configurations are arranged alternately, the stent has a high expanded state retention force.

Similarly to the stents 1 and 60, the connection portion 3 is provided in the neighborhood of a middle position between the apex of the one-end side bent portion 21 of the wavy annular member 2 and apex of the other-end side bent portion 22 of the adjacent wavy annular member 2. In other words, the connection portion 3 is formed not at the apexes of the bent portions 21, 22, but is shifted to some extent from the apexes of the bent portions 21, 22. In other words, the connection portion 3 is shifted toward the one or other end of the stent with respect to the apexes of the bent portions.

In the stent 70, similarly to the stent 1, an annular unit composed of two wavy annular members 2 connected with each other by the first connection portion (straight-line portion connection type connection portion) 31 is connected with an adjacent annular unit by the second connection portion (low engaging portion connection type connection portion) 32.

In the stent 70 of this embodiment two first connection portions (oppositional portion connection type connection portion) 31 are formed for one wavy annular member, with the first connection portions 31 substantially opposed to each other with respect to the axis of the stent 1. The first connection portions 31 are disposed linearly in the axial direction of the stent 70. Similarly in the stent 70 of this embodiment two second connection portions (low engaging portion connection type connection portion) 32 are formed for one wavy annular member, with the second connection portions 32 substantially opposed to each other with respect to the axis of the stent 70. The second connection portions 32 are uncontinuously and linearly formed in the axial direction of the stent 1. The two first connection portions 31 and the two second connection portions 32 are substantially equiangularly disposed with respect to the axis of the stent 1.

Figure 24:
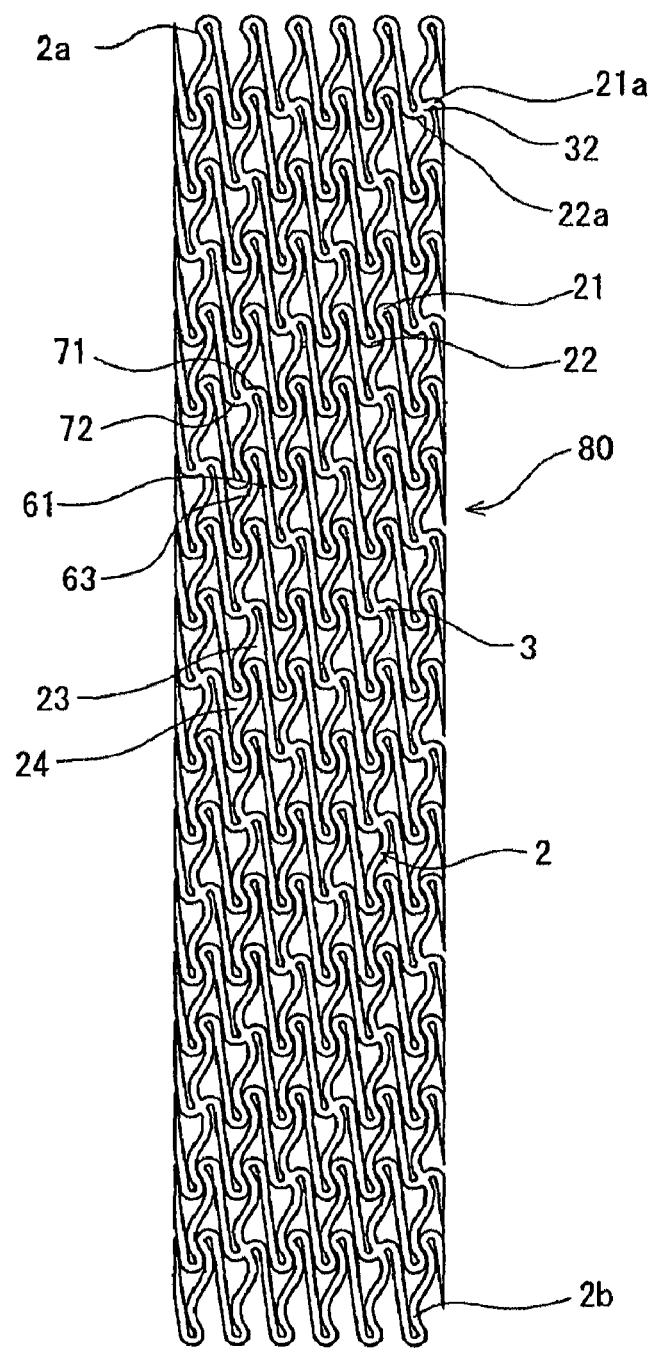
FIG. 24 is a development view showing a stent of another embodiment of the present invention.
Figure 25:
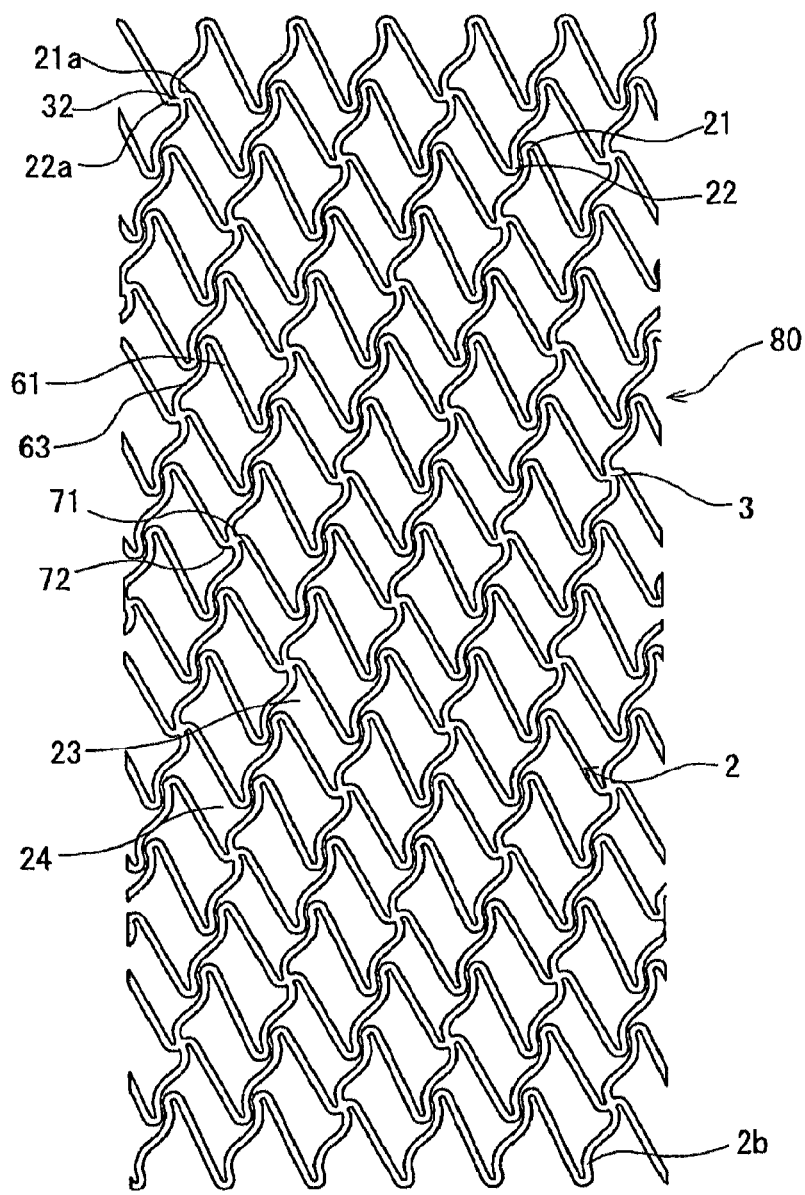
FIG. 25 is a development view showing the stent shown in FIG. 20 immediately after the stent is manufactured.

The form of the stent may have a construction shown in FIGS. 24 and 25.

FIG. 24 is a development view showing a stent of another embodiment of the present invention. FIG. 25 is a development view showing the stent shown in FIG. 24 immediately after the stent is manufactured.

The basic construction of a stent 80 has the same construction as that of the above-described stents 1 and 70. The stent 80 has the same construction as that of the stent 70 except that the configuration of the connection portion is different from that of the connection portion of the stent 70.

As shown in FIGS. 24 and 25, the stent 80 has a plurality of the wavy annular members 2 arranged adjacently to each other in the axial direction thereof, with the adjacent wavy annular members connected with each other.

Similarly to the stent 60, one wave of the wavy annular member 2 is composed of a plurality of straight-line portions 61 extended obliquely at a predetermined angle with respect to the axis of the stent 80 and a plurality of S-shaped curved portions 63 connected with an upper end of the straight-line portion 61 and curved in a shape of S. Similarly to the stent 60, in the stent 80, the apex 21a of each of the one-end side bent portions 21 of each wavy annular member 2 penetrates into the space 23 formed between the adjacent other-end side bent portions 22 of one of the adjacent wavy annular members 2. Similarly the apex 22a of each of the other-end side bent portions 22 of each wavy annular member 2 penetrates into the space 24 formed between the adjacent one-end side bent portions 21 of the other of the adjacent wavy annular members 2. That is, the adjacent wavy annular members 2 overlap each other in the axial direction of the stent 80.

The apex 21.a of the one-end side bent portion 21 of each of the wavy annular members 2 and the apex 22a of the other-end side bent portion 22 of the adjacent wavy annular member 2 are depressed and engage each other.

In the stent 80, the apex 72 of one other-end side bent portion 22 of the wavy annular member 2 is axially shorter than the apexes of other other-end side bent portions of the wavy annular member 2. The apex 71, proximate to the axially shorter apex 72, of one one-end side bent portion 21 of the wavy annular member 2 is axially shorter than the apexes of other one-end side bent portions of the wavy annular member 2. Therefore in the portion proximate to the apexes 71 and 72, the bent portions of the wavy annular member overlap each other in a small amount in the axial direction of the stent 70, thus forming a low engaging portion.

The stent 80 of this embodiment is formed as the low engaging portion connection type connection portion 32 formed at the low engaging portion where the apex 71 of the one-end side bent portion 21 of one wavy annular member 2 and the apex 72 of the other-end side bent portion 22 of the adjacent wavy annular member 2 engage each other. In the stent 80, the connection portion 3 consists of the low engaging portion connection type connection portion.

In the stent 80 of this embodiment two connection portions 32 are formed for one wavy annular member, with the connection portions substantially opposed to each other with respect to the axis of the stent 80. The connection portions 32 are disposed spirally in the axial direction of the stent 80. In the stent 80 of this embodiment the low engaging portion connection type connection portion 32 may be expressed as the low engaging portion integration portion.

Figure 26:
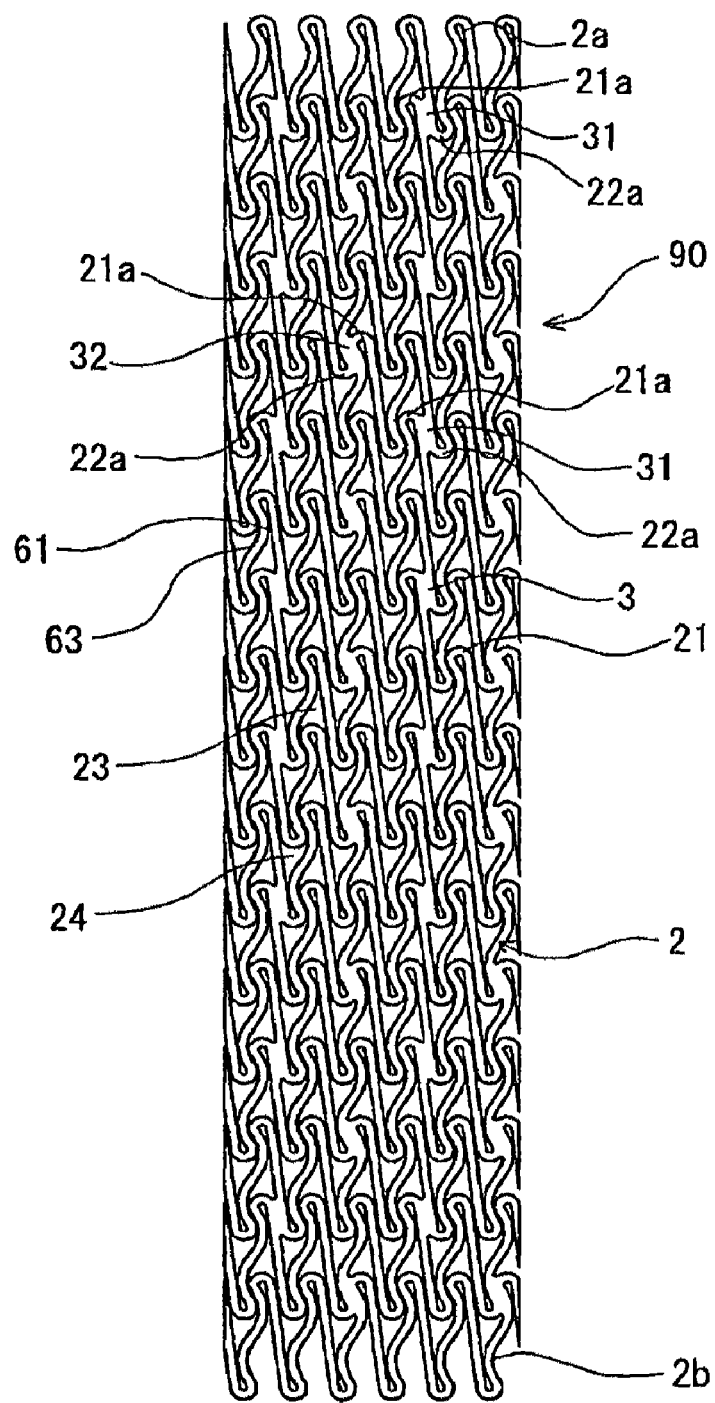
FIG. 26 is a development view showing a stent of another embodiment of the present invention.
Figure 27:
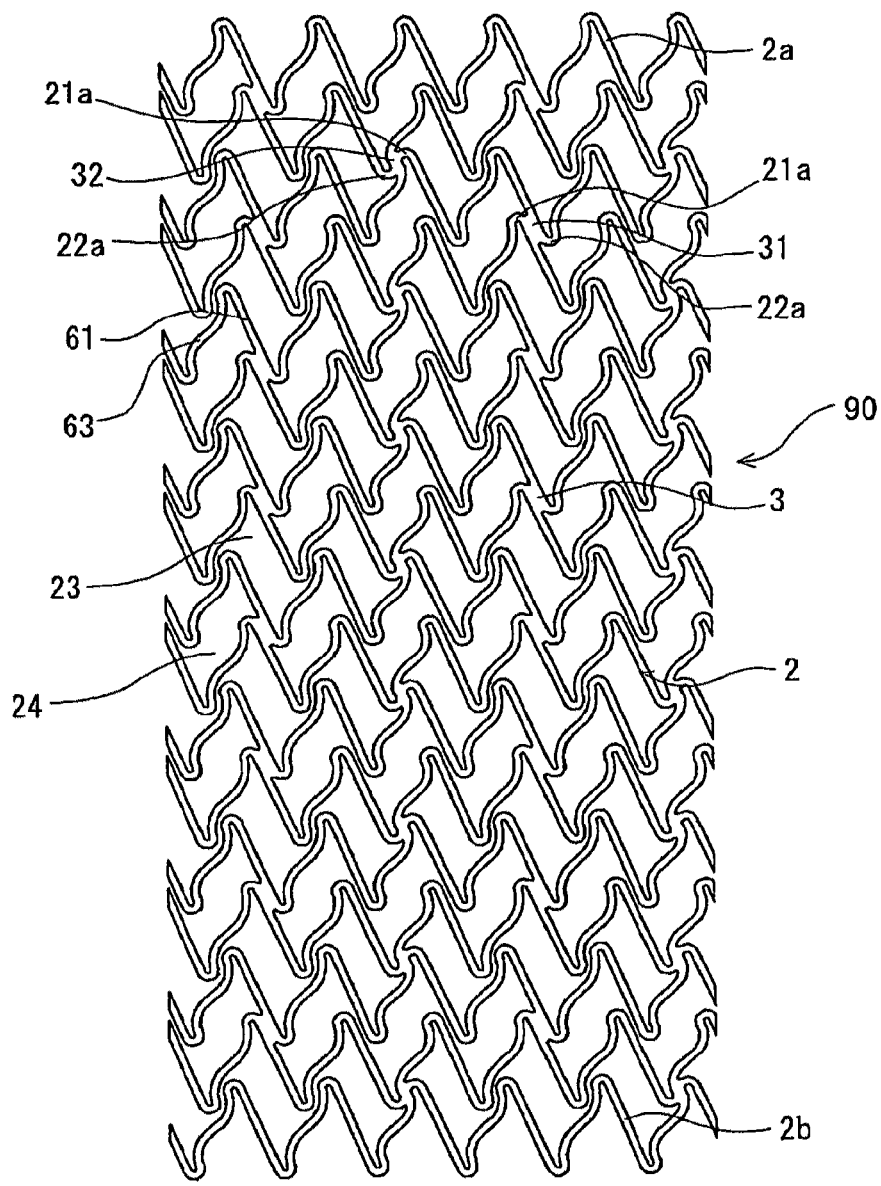
FIG. 27 is a development view showing the stent shown in FIG. 26 immediately after the stent is manufactured.

The form of the stent may have a construction shown in FIGS. 26 and 27.

FIG. 26 is a development view showing a stent of another embodiment of the present invention. FIG. 27 is a development view showing the stent shown in FIG. 26 immediately after the stent is manufactured.

The basic construction of a stent 90 has the same construction as that of the above-described stents 1 and 60. The stent 90 has the same construction as that of the stent 60 except that the widths of the material forming all the wavy annular members 2 are almost equal to each other and that the configurations of the connection portions 31, 32 are different from that of the connection portion of the stent 60.

As shown in FIGS. 26 and 27, the stent 90 has a plurality of the wavy annular members 2 arranged adjacently to each other in the axial direction thereof, with the adjacent wavy annular members connected with each other. Similarly to the stent 1, in the stent 90, the apex 21a of each of the one-end side bent portions 21 of each wavy annular member 2 penetrates into the space 23 formed between the adjacent other-end side bent portions 22 of one of the adjacent wavy annular members 2. Similarly the apex 22a of each of the other-end side bent portions 22 of each wavy annular member 2 penetrates into the space 24 formed between the adjacent one end side bent portions 21 of the other of the adjacent wavy annular members 2. That is, the adjacent wavy annular members 2 overlap each other in the axial direction of the stent 90.

Similarly to the stent 60, one wave of the wavy annular member 2 is composed of a plurality of straight-line portions 61 extended obliquely at a predetermined angle with respect to the axis of the stent and a plurality of S-shaped curved portions 63 connected with an upper end of the adjacent straight-line portion 61 and curved in a shape of S. The apex 21a of the one-end side bent portion 21 of each of the wavy annular members 2 and the apex 22a of the other-end side bent portion 22 of the adjacent wavy annular member 2 are depressed and engage each other.

In the stent 90 of this embodiment similarly to the stent 60, the connection portion 3 has the straight-line portion connection type connection portion 31 formed at a rear portion (in other words, straight-line portion 61) of the portion where the apex 21a of the one-end side bent portion 21 of one wavy annular member 2 and the apex 22a of the other-end side bent portion 22 of the adjacent wavy annular member 2 are proximate to each other and engage each other. The straight-line portion connection type connection portion 31 of the stent 90 is wider than that of the above-described stent 60. Thus the straight-line portion connection type connection portion 31 can be expressed as a straight-line portion integration portion.

In the stent 90 of this embodiment similarly to the stent 60, the connection portion 3 has the engaging position connection type connection portion 32 formed at a portion where the apex 21a of the one-end side bent portion 21 of one wavy annular member 2 and the apex 22a of the other-end side bent portion 22 of the adjacent wavy annular member 2 engage each other. The expression of the engaging position connection type connection portion 32 can be changed to the portion of connecting the inner side of the engaging portion. The expression of the above-described straight-line portion connection type connection portion 31 can be changed to a portion of connecting the outer side of the engaging portion. In the stent 90, the engaging position connection type connection portion 32 is wider than that of the engaging position connection type connection portion 32 of the stent 60. Thus the engaging position connection type connection portion 32 can be expressed as the engaging portion integration portion.

In the stent 90 of this embodiment similarly to the stent 60. The stent 90 of this embodiment has the connection portions of the two types, namely, the straight-line portion connection type connection portion (portion of connecting outer side of the engaging portion) 31 and the engaging position connection type connection portion (portion of connecting inner side of the engaging portion) 32. These connection portions are arranged alternately in the axial direction of the stent 90. Because the connection portions having the different configurations are arranged alternately, the stent has a high expanded state retention force.

Figure 28:
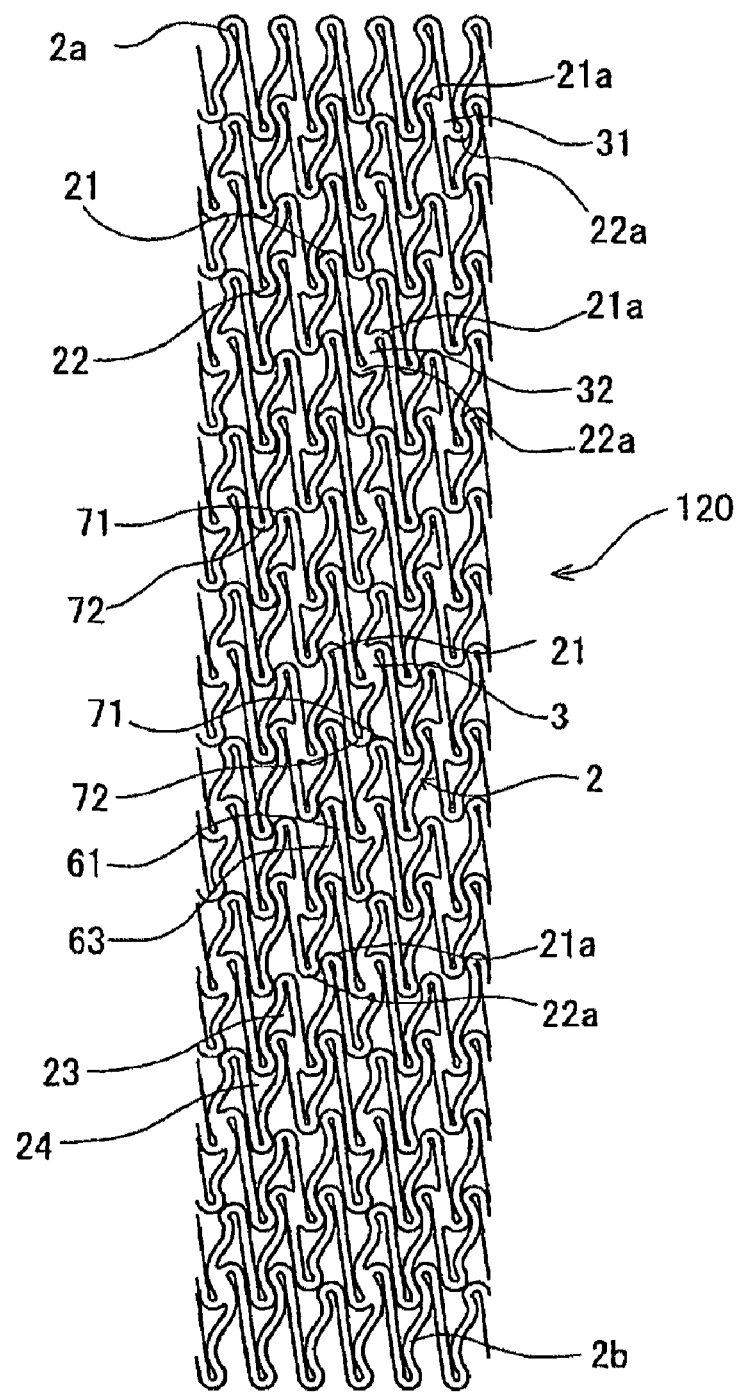
FIG. 28 is a development view showing a stent of another embodiment of the present invention.
Figure 29:
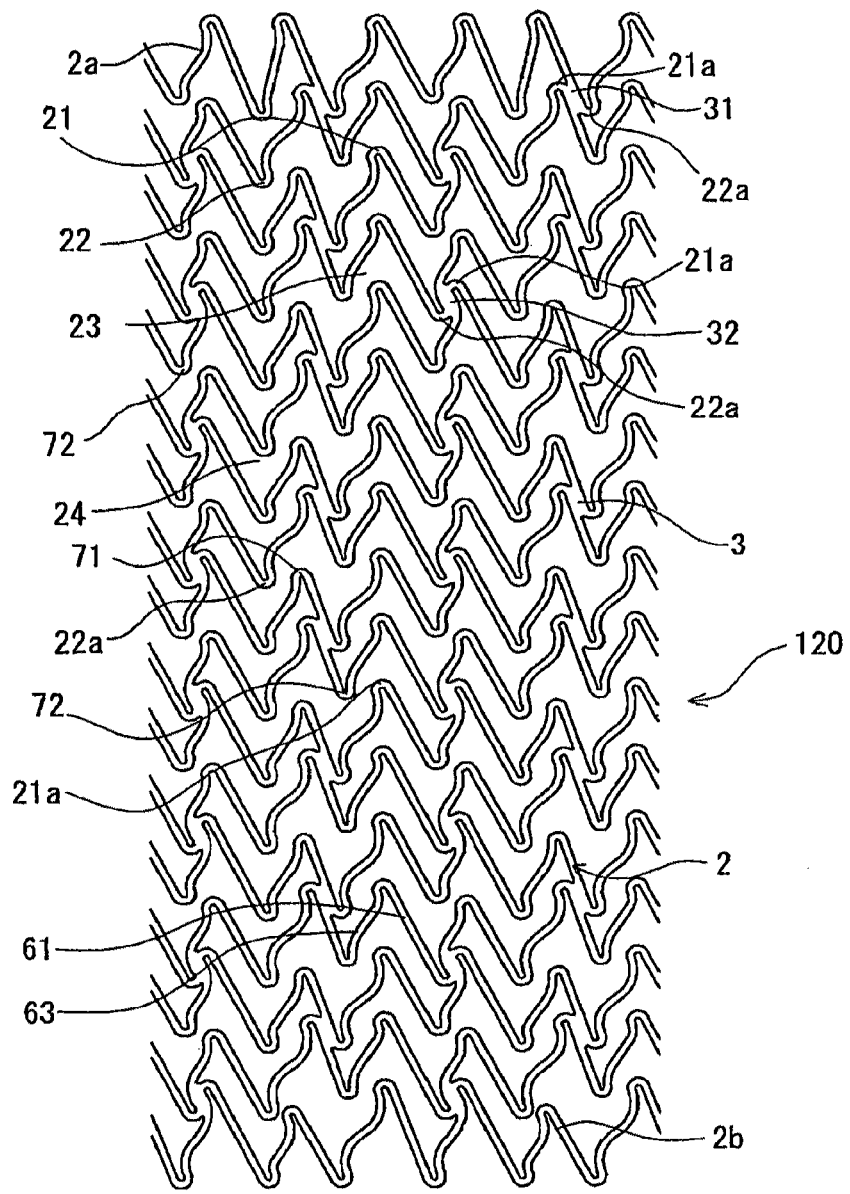
FIG. 29 is a development view showing the stent shown in FIG. 28 immediately after the stent is manufactured.

The form of the stent may have a construction shown in FIGS. 28 and 29.

FIG. 28 is a development view showing a stent of another embodiment of the present invention. FIG. 29 is a development view showing the stent shown in FIG. 28 immediately after the stent is manufactured.

The basic construction of a stent 120 has the same construction as that of the above-described stent 1 and 90. The stent 120 has the same construction as that of the stent 90 except that the configuration of the wavy annular member is different from that of the wavy annular member of the stent 90.

As shown in FIGS. 28 and 29, the stent 120 has a plurality of the wavy annular members 2 arranged adjacently to each other in the axial direction thereof, with the adjacent wavy annular members connected with each other. Similarly to the stent 1, in the stent 120, the apex 21.*a* of each of the one-end side bent portions 21 of each wavy annular member 2 penetrates into the space 23 formed between the adjacent other-end side bent portions 22 of one of the adjacent wavy annular members 2. Similarly the apex 22*a* of each of the other-end side bent portions 22 of each wavy annular member 2 penetrates into the space 24 formed between the adjacent one-end side bent portions 21 of the other of the adjacent wavy annular members 2. The apex 21*a* of the one-end side bent portion 21 of each of the wavy annular members 2 and the apex 22*a* of the other-end side bent portion 22 of the adjacent wavy annular member 2 are depressed and engage each other. But in the stent 120, all apexes do not engage each other, and the low engaging portion is formed.

Except the one-end side bent portion 21 disposed at the end of the stent 120, two apexes 71 of a plurality of apexes 21*a* of the one-end side bent portions 21 of each wavy annular member 2 are axially shorter than the apexes 21*a* of the one-end side bent portions of the wavy annular members 2. Except the other-end side bent portion 22 disposed at the end of the stent 120, two apexes 72 of a plurality of apexes 22*a* of the other-end side bent portions 22 of each wavy annular member 2 are axially shorter than the apexes 22*a* of the other-end side bent portions of the wavy annular members 2. The apex 72 axially shorter than the other apexes of the odd-numbered wavy annular member 2 is proximate to the apex 71 axially shorter than the other apexes of the even-numbered wavy annular member 2. But both apexes 72 and 71 do not engage each other. That is, a plurality of (four) engaging portions of the apexes of the bent portions and two proximate portions (unengaging portion) are formed between the odd-numbered wavy annular member 2 and the even-numbered wavy annular member 2. The two apexes 72 are substantially opposed to each other with respect to the axis of the stent. Similarly the two apexes 71 are substantially opposed to each other with respect to the axis of the stent.

The apex 72 axially shorter than the other apexes of the even-numbered wavy annular member 2 is proximate to the apexes 21*a* of the odd-numbered wavy annular member 2. In the portion proximate to the apexes 72 and 21*a*, the bent portions of the wavy annular members overlap each other in a small amount in the axial direction of the stent 120, thus forming the low engaging portion. That is, a plurality of (four) engaging portions of the apexes of the bent portions and two low engaging portions are formed between the even-numbered wavy annular member 2 and the odd-numbered wavy annular member 2.

In the stent 120 of this embodiment, the connection portion 3 has the straight-line portion connection type connection portion 31 formed at a rear portion (in other words, straight-line portion 61) of the portion where the apex 21*a* of the one-end side bent portion 21 of one wavy annular member 2 and the apex 22*a* of the other-end side bent portion 22 of the adjacent wavy annular member 2 are proximate to each other, with the apexes 21*a* and 22*a* engaging each other. The straight-line portion connection type connection portion 31 of the stent 120 is wider than that of the above-described stent 60. Thus the straight-line portion connection type connection portion 31 can be expressed as the straight-line portion integration portion.

In the stent 120 of this embodiment similarly to the stent 60, the connection portion 3 has the engaging position connection type connection portion 32 formed at the portion where the apex 21*a* of the one-end side bent portion 21 of one wavy annular member 2 and the apex 22*a* of the other-end side bent portion 22 of the adjacent wavy annular member 2 engage each other. The expression of the engaging position connection type connection portion 32 can be changed to the portion of connecting the inner side of the engaging portion. The expression of the above-described straight-line portion connection type connection portion 31 can be changed to a portion of connecting the outer side of the engaging portion. In the stent 120, the engaging position connection type connection portion 32 is wider than that of the engaging position connection type connection portion 32 of the stent 60. Thus the engaging position connection type connection portion 32 can be expressed as the engaging portion integration portion.

In the stent 120, all the straight-line portion connection type connection portion 31 are not the unengaging portion or the low engaging portion, but connect (integrate) the outer side of the engaging portion. In the stent 120, all the engaging position connection type connection portion 32 are not the unengaging portion or the low engaging portion, but connect (integrate) the inner side of the engaging portion.

Similarly to the stent 60, the stent 120 of this embodiment has the connection portions of the two types, namely, the straight-line portion connection type connection portion (portion of connecting outer side of the engaging portion) 31 and the engaging position connection type connection portion (portion of connecting inner side of the engaging portion) 32. These connection portions are arranged alternately in the axial direction of the stent 120. Because the connection portions having the different configurations are arranged alternately, the stent has a high expanded state retention force.

Figure 30:
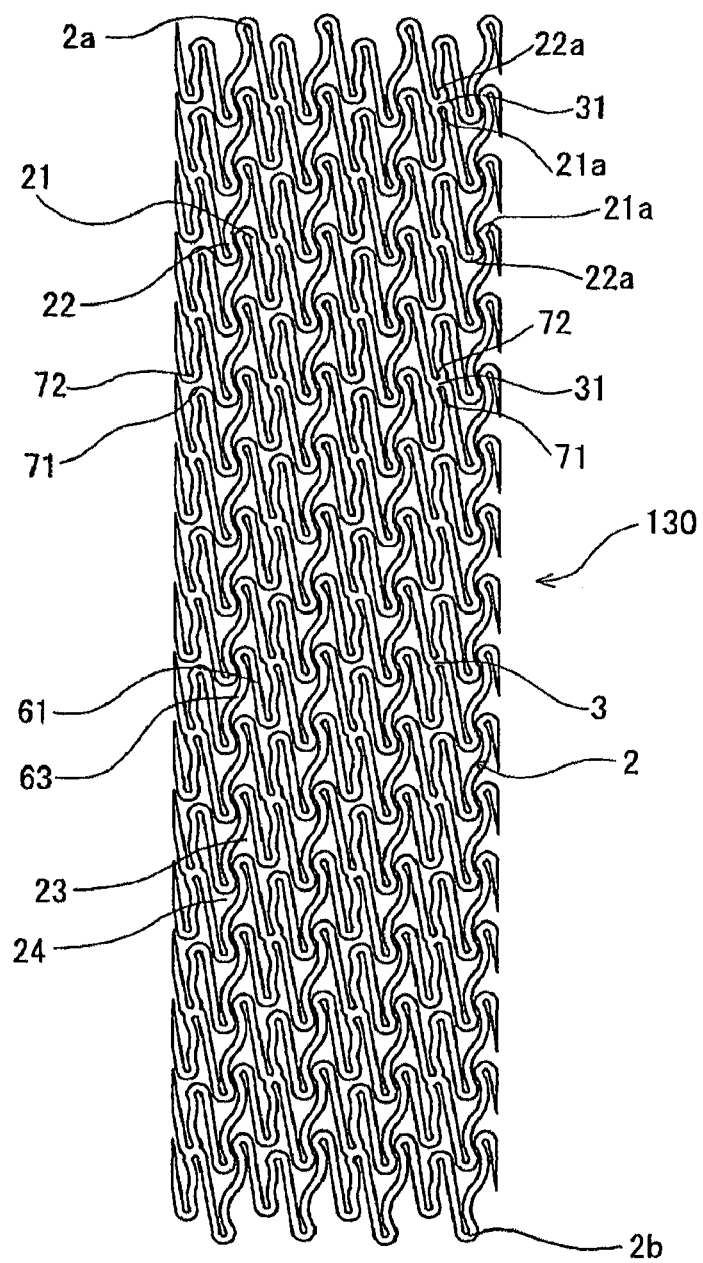
FIG. 30 is a development view showing a stent of another embodiment of the present invention.
Figure 31:
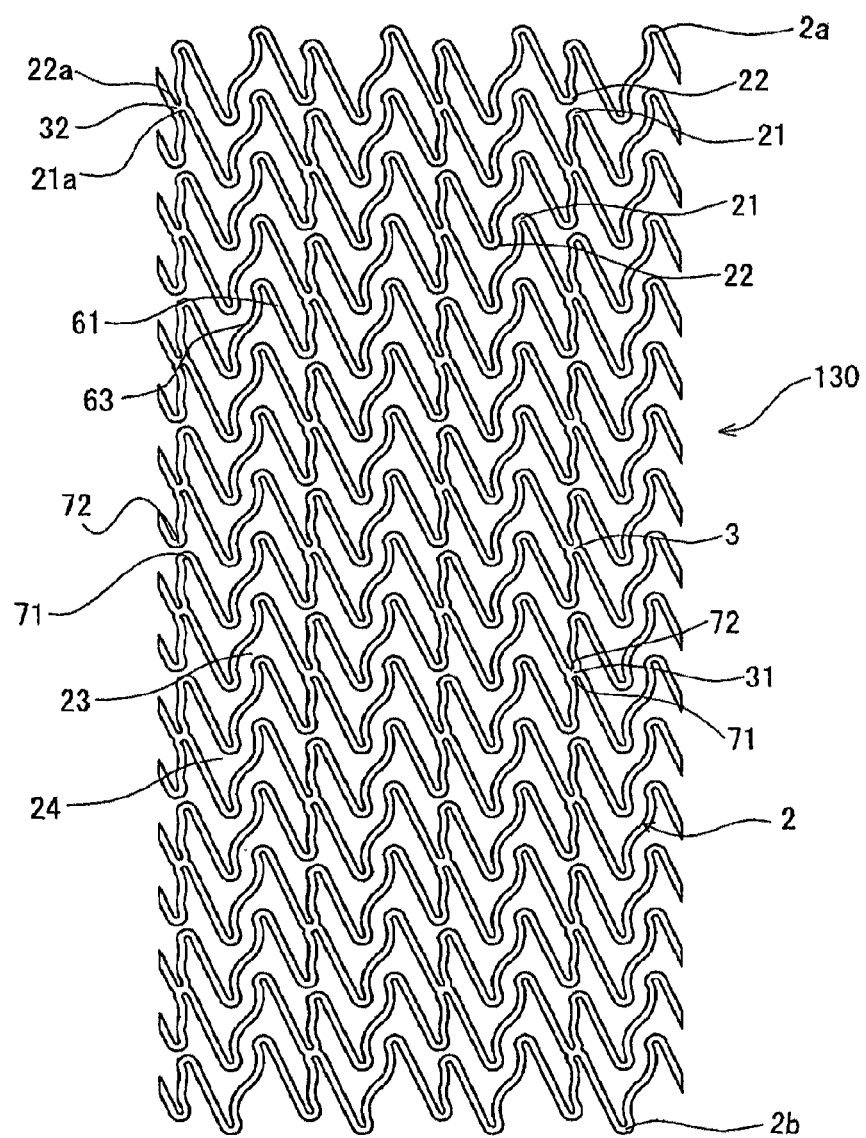
FIG. 31 is a development view showing the stent shown in FIG. 30 immediately after the stent is manufactured.

The form of the stent may have a construction shown in FIGS. 30 and 31.

FIG. 30 is a development view showing a stent of another embodiment of the present invention FIG. 31 is a development view showing the stent shown in FIG. 30 immediately after the stent is manufactured.

The basic construction of a stent 130 has the same construction as that of the above-described stent 1 and 90. The stent 130 has the same construction as that of the stent 90 except that the configuration of the wavy annular member is different from that of the wavy annular member of the stent 90.

As shown in FIGS. 30 and 31, the stent 130 has a plurality of the wavy annular members 2 arranged adjacently to each other in the axial direction thereof, with the adjacent wavy annular members connected with each other. Similarly to the stent 1, in the stent 130, the apex 21*a* of each of the one-end side bent portions 21 of each wavy annular member 2 penetrates into the space 23 formed between the adjacent other-end side bent portions 22 of one of the adjacent wavy annular members 2. Similarly the apex 22*a* of each of the other-end side bent portions 22 of each wavy annular member 2 penetrates into the space 24 formed between the adjacent one-end side bent portions 21 of the other of the adjacent wavy annular members 2. The apex 21*a* of the one-end side bent portion 21 of each of the wavy annular members 2 and the apex 22*a* of the other-end side bent portion 22 of the adjacent wavy annular member 2 are depressed and engage each other. But in the stent 130, all apexes do not engage each other, and the unengaging portion is formed.

In this stent 130, as shown in FIGS. 30 and 31, the wavy annular members 2 have eight one-end side bent portions 21 and eight other-end side bent portions 22. Except the one-end side bent portion 21 disposed at the end of the stent 130, four apexes 71 (every other apex) of a plurality of apexes 21*a* of the one-end side bent portions 21 of each wavy annular member 2 are axially shorter than the apexes 21a of the one-end side bent portions of the wavy annular members 2. Except the other-end side bent portion 22 disposed at the end of the stent 130, four apexes 72 (every other apex) of a plurality of apexes 22a of the other-end side bent portions 22 of each wavy annular member 2 are axially shorter than the apexes 22a of the other-end side bent portions of the wavy annular members 2. The apex 72 axially shorter than the other apexes of the wavy annular member 2 is proximate to the apex 71 axially shorter than the other apexes of the wavy annular member 2. But both apexes 72 and 71 do not engage each other. That is, four engaging portions of the apexes of the bent portions and four proximate portions (unengaging portion) are formed between the wavy annular members 2. The four apexes 71 are substantially equiangularly disposed with respect to the axis of the stent 130. The four apexes 72 are substantially equiangularly disposed with respect to the axis of the stent 130.

In the stent 130 of this embodiment the connection portion 31 connects or integrates the apex 72 axially shorter than the other apexes of the wavy annular member 2 to the apexes 71 axially shorter than the other apexes of the wavy annular member 2. The connection portion 31 of the stent 130 is a proximate position connection type connection portion. The connection portion 31 integrates the tip of both of the apex 71 and the apex 72. In the wavy annular members 2 of the stent 130, the apex 71 and the apex 72 are arranged alternately. The stent 130 is easy to mount it on an expandable balloon of an appliance by reducing the diameter of the stent and reduce the outer diameter of the stent when it is mounted on the balloon. In the stent 130, there are few decreases of the length of axis direction of the stent when it is expanded.

It is preferable that each of the stents of the above-described embodiments is formed as a tube, has a diameter whose dimension is so set that it can be inserted into the lumen of the predetermined portion inside the organism, and can be expanded when a force spreading radially outwardly from the inside of the tube is applied thereto. That is, it is preferable that the stents are balloon expandable stents.

It is preferable that the material of the balloon expandable stent has a certain degree of compatibility with the organism. For example, it is possible to use stainless steel, tantalum or tantalum alloys, platinum or platinum alloys, gold or gold alloys, cobalt based alloys, a cobalt-chrome alloy, a titanium alloy, and a niobium alloy. It is preferable to plate the stent with a noble metal such as gold and platinum after the stent is fabricated into a final shape. As the stainless steel SUS 316L most corrosion-resistant can be preferably used.

It is preferable to anneal the stent 1 after it is fabricated into the final shape. Annealing improves the flexibility and plasticity of the entire stent. Thereby the stent can be favorably implanted at a curved portion of a blood vessel. As compared with a non-annealed stent, the annealed stent has a lower force of restoring to an original state after it is expanded, and especially has a lower force of restoring to an original linear state when it is expanded at the curved portion of the blood vessel. This minimizes physical stimulation to the inner wall of the curved portion of the blood vessel, thus reducing the cause of a recurrence of stenosis. It is preferable to anneal the stent by heating it to 900 to 1200° C. in an inert gas atmosphere (e.g., a mixture gas of nitrogen and hydrogen) so that no oxide film is formed on the surface of the stent and then slowly cooling it.

The stent 1 has a diameter favorably 0.8 to 1.8 mm and more favorably 0.9 to 1.6 mm in an unexpanded state. The stent 1 has a length favorably 8 to 40 mm in an unexpanded state. It is preferable that each wavy annular members 2 has a length of 8 to 25 mm. It is preferable that the length of each connection portion 3 is 20-200 μm.

The stent is shaped by removing portions other than a frame structure from a tube (more specifically, metal pipe). More specifically, the stent is formed by removing unnecessary portions from the metal pipe by an etching process, known as photo-fabrication, using masks and chemicals; electric discharge machining using a die; and cutting processing (for example, mechanical polishing, laser cutting processing). In addition, it is preferable to polish edges of the frame structure by chemical polishing or electrolytic polishing after the frame structure is formed.

The stent of the present invention is not limited to the balloon expandable stent. That is, the stent of the present invention includes the so-called self-expandable stent which is formed substantially cylindrically, decreased in its diameter when it is inserted into the organism, and is capable of returning to a configuration before its diameter is decreased, when it is implanted in the organism. It is possible to adopt the modes of the stents of the above-described embodiments.

The outer diameter, thickness, and length of the stent are different respectively in dependence on a portion where the stent is implanted. When the stent is expanded (when it is not contracted in its diameter and when it is restored to its original state), the outer diameter thereof is favorably in the range of 2.0 to 30 mm and more favorably in the range of 25 to 20 mm; the thickness thereof is favorably in the range of 0.04 to 1.0 mm and more favorably in the range of 0.06 to 0.5 mm; and the length thereof is favorably in the range of 10-150 mm and more favorably in the range of 15 to 100 mm. In the case of the stent to be implanted in the blood vessel the outer diameter thereof is favorably in the range of 2.0 to 14 mm and more favorably in the range of 2.5 to 12 mm; the thickness thereof is favorably in the range of 0.04 to 0.3 mm and more favorably in the range of 0.06 to 0.22 mm; and the length thereof is favorably in the range of 5-100 mm and more favorably in the range of 10 to 80 mm.

The stent is made of a super-elastic alloy. Thus by eliminating a load applied to the stent it returns to the configuration at the time when it has been manufactured. It is preferable that the stent is integrally and cylindrically made of the super-elastic alloy showing super-elasticity before and after the stent is inserted into the organism.

The super-elastic alloy can be preferably used as the super-elastic metal. Herein the super-elastic alloy means a so called shape memory alloy that shows super-elasticity essentially at the temperature (in the vicinity of 37□) of the organism. The following super-elastic metals can be favorably used: A Ti—Ni alloy of 49-54 atomic percent of Ni, a Cu—Zn alloy of 38.5-41.5 wt % of Zn, a Cu—Zn—X alloy of 1-10 wt % of X (X=Be, Si, Sn, Al, Ga), and a Ni—Al alloy of 36-38 atomic percent of Al. The Ti—Ni alloy is most favorable. The mechanical characteristic of the Ti—Ni alloy can be appropriately changed by replacing a part of the Ti—Ni alloy with 0.01-10.0% of X to obtain a Ti—Ni—X alloy (X=Co, Fe, Mn, Cr, V, Al, Nb, W, B, Au, and Pd) or by replacing a part of the Ti—Ni alloy with 0.01-30.0 atomic percent of X to obtain a Ti—Ni—X alloy (X=Cu, Pb, Zr). Further the mechanical characteristic of the super-elastic alloy can be appropriately changed by selectively adopting a cold working ratio or/and the condition of final heat treatment.

In the case where the Ti—Ni—X alloy is used, it is also possible to change the mechanical characteristic of the super-elastic alloy appropriately by selectively adopting the cold working ratio or/and the condition of the final heat treatment. The buckling strength yield stress when load is applied to stent) of the super-elastic alloy to be used is favorably in the range of 5-200 kg/mm$^2$ (22° C.) and more favorably in the range of 8-150 kg/mm$^2$. The restoring stress (yield stress when load is eliminated from stent) of the super-elastic alloy is favorably in the range of 3-180 kg/mm$^2$ (22° C.) and more favorably in the range of 5-130 kg/mm$^2$. The super-elasticity means that when a metal is deformed (bent stretched, compressed) to a region in which it deforms plastically at a service temperature, it returns to its original configuration substantially without heating it after an applied load is eliminated.

The stent is formed by removing (for example, cutting, dissolving) a part of a pipe made of the super-elastic metal, not constituting the stent. Thereby the stent is obtained as an integral product. The pipe made of the super-elastic metal to be used to form the stent of the present invention can be produced by dissolving the super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating a drawing step and a heat treatment step to adjust the diameter and thickness of the pipe to a predetermined thickness and reduced diameter, and finally polishing the surface of the pipe chemically or physically. The pipe made of the super-elastic metal can be processed into the base material for the stent by a cutting work such as laser processing (for example, YAG laser), electrical discharge machining, chemical etching cutting processing or in combination thereof.

The stent of the present invention may be coated with a material suitable for the organism on its inner surface, outer surface or inner and outer surfaces. As the material suitable for the organism, synthetic resin and metal suitable for the organism can be used. The following inactive metals are used to coat the surface of the stent gold by an electroplating method, stainless steel by an evaporation method, silicon carbide by a sputtering method, diamond-like carbon, plated titanium nitride, and plated gold. As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone resin. It is preferable to use polyolefin, polyamide elastomer, polyester, polyurethane, silicone resin. A resin decomposable in the organism (polylactic acid, polyglycolic acid, polylactic acid-polyglycolic acid copolymer) is also favorable. It is preferable that a film of the synthetic resin is soft such an extent as not to prevent a frame constituting the stent from being curved. The thickness of the film of the synthetic resin is favorably in the range of 3 to 300 μm and more favorably in the range of 5 to 100 μm.

As the method of thinly coating the surface of the stent with the synthetic resin, it is possible to use a method of inserting the stent into the melted synthetic resin or into the synthetic resin dissolved in a solution. It is also possible to use a chemical evaporation method of polymerizing a monomer over the surface of the pipe made of the super-elastic metal. In the case where the surface of the stent is coated very thinly with the synthetic resin, the use of a dilute solution or the chemical evaporation method is preferable. To improve the quality of the material suitable for the organism to a higher extent the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

An embodiment of the blood vessel expansion appliance of the present invention will be described below.

Figure 17:
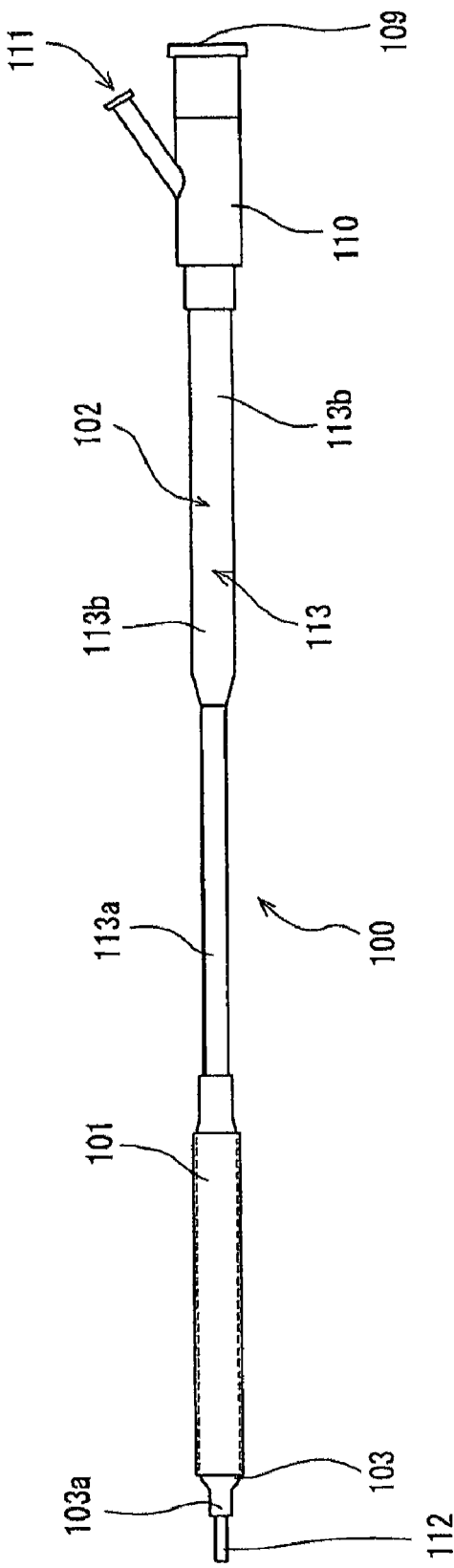
FIG. 17 is a front view showing a stent delivery device of an embodiment of the present invention.
Figure 18:
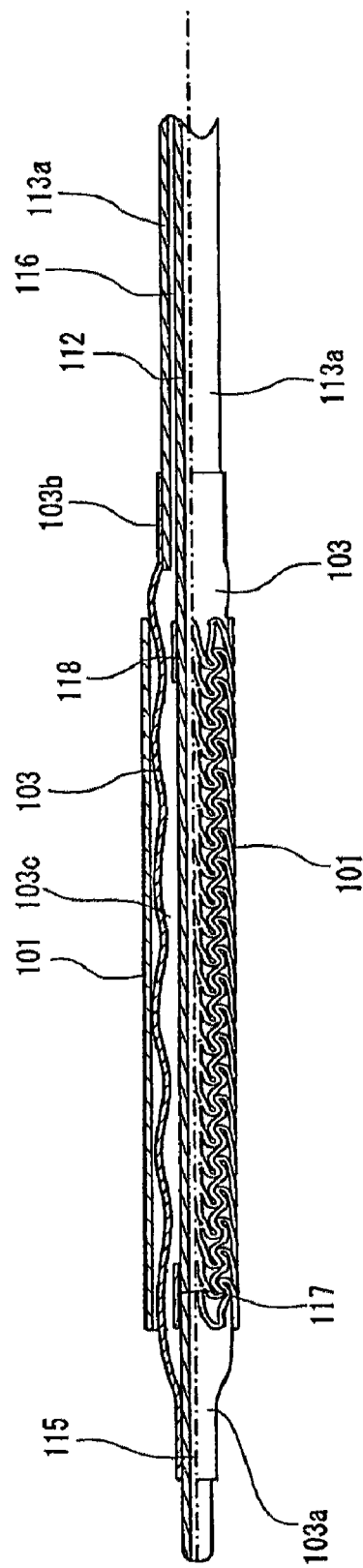
FIG. 18 is a partly enlarged sectional view showing a distal portion of the stent delivery device shown in FIG. 17.

FIG. 17 is a front view showing an stent delivery device of an embodiment of the present invention. FIG. 18 is a partly enlarged sectional view showing a distal portion of the stent delivery device shown in FIG. 17.

A blood vessel expansion appliance 100 of the present invention has a tubular shaft body 102; a balloon 103, foldable and expandable, which is disposed at a distal end of the shaft body 102; and a stent 201 mounted on the folded balloon 103, with the stent 201 covering the balloon 103. The stent 201 is expanded owing to the expansion of the balloon 103.

The stent 201 has a construction similar to that of the above-described stent 1. That is, the stent 201 has a plurality of wavy annular members 2 arranged adjacently to each other in the axial direction thereof, with the adjacent wavy annular members 2 connected with each other. Each of the wavy annular members 2 has a plurality of the one-end side bent portions 21 each having the apex at the one-end side of the stent 1 in the axial direction thereof and a plurality of the other-end side bent portions 22 each having the apex at the other-end side of the stent 1 in the axial direction thereof. The apex 21a of each of the one-end side bent portions 21 of each wavy annular member 2 penetrates into the space 23 formed between the adjacent other-end side bent portions 22 of one of the adjacent wavy annular members 2. The apex 22a of each of the other-end side bent portions 22 of each wavy annular member 2 penetrates into the space 24 formed between the adjacent one-end side bent portions 21 of the other of the adjacent wavy annular members 2. The apex 21a of the one-end side bent portion 21 of each of the wavy annular members 2 and the apex 22a of the other-end side bent portion 22 of the adjacent wavy annular member 2 curve in an approach direction, thus engaging each other.

As the stent for use in the blood vessel expansion appliance, it is preferable to use a balloon expandable stent which has a diameter whose dimension is so set that it can be inserted into the lumen of the predetermined portion inside the organism, and can be expanded when the force spreading radially outwardly from the inside of the tube is applied thereto. That is, it is preferable that the stent is the balloon expandable stent.

More specifically, as the stent 201, it is possible to use the stents of the above-described embodiments. More specifically, as the stent 201, it is possible to use any of the stents 1, 10, 20, 30, 40, and 50. It is preferable that the area of the wavy element of the stent is 60 to 80% of the area of the peripheral surface of the stent including vacant spaces thereof when the stent is mounted on the balloon 103.

The shaft body 102 of the blood vessel expansion appliance 100 of the present invention has a balloon expansion lumen whose one end communicates with the inside of the balloon 103. The blood vessel expansion appliance 100 has a radiographing member fixed to an outer surface of the shaft body 102 at a position corresponding to the center of the stent or two radiographing members fixed to the outer surface of the shaft body 102 at positions corresponding to one and other ends of the central portion of the stent having a predetermined length.

As shown in FIG. 17, the shaft body 102 of the blood vessel expansion appliance 100 of this embodiment has a guide wire lumen 115 whose one end is open at a front end of the shaft body 102 and whose other end is open at a rear end of the shaft body 102.

The stent delivery device 100 of the present invention has the tubular shaft body 102, the stent-expanding balloon 103 attached to the front end of the shaft body 102; and the stent

201 mounted on the balloon 103. The shaft body 102 has an inner tube 112, an outer tube 113, and a branch hub 110.

As shown in FIG. 17, the inner tube 112 has the guide wire lumen 115 into which a guide wire is inserted. The length of the inner tube 112 is favorably 100 to 2000 mm and more favorably 150 to 1500 mm. The outer diameter of the inner tube 112 is favorably 0.1 to 1.0 nm and more favorably 0.3 to 0.7 mm. The thickness of the inner tube 112 is favorably 10 to 150 μm and more favorably 20 to 100 μm. The inner tube 112 is inserted into the outer tube 113 to such an extent that the front end of the inner tube 112 projects from the outer tube 113. A balloon-expanding lumen 116 is formed between the outer surface of the inner tube 112 and the inner surface of the outer tube 113 and has a large volume. The front end of the outer tube 113 into which the inner tube 112 is inserted is located a little rearward from the front end of the inner tube 112.

The length of the outer tube 113 is favorably 100 to 2000 mm and more favorably 150-1500 mm. The outer diameter of the outer tube 113 is favorably 0.5 to 1.5 mm and more favorably 0.7 to 1.1 mm. The thickness of the outer tube 113 is favorably 25 to 200 μm and more favorably 50 to 100 μm.

In the stent delivery device 100 of the embodiment the outer tube 113 is composed of a front-end side outer tube 113a and a shaft-body side outer tube 113b joined with the front-end side outer tube 113a. The diameter of the front-end side outer tube 113a decreases taperingly in the region forward from the joining position at which the front-end side outer tube 113a and the shaft body side outer tube 113b are joined with each other. The diameter of a portion of the front-end side outer tube 113a forward from the tapered region has a small diameter.

The outer diameter of the front-end side outer tube 113a at its smaller-diameter portion is favorably 050 to 1.5 mm and more favorably 0.60 to 1.1 mm. The outer diameter of the front-end side outer tube 113a at its rear end portion and that of the shaft-body side outer tube 113b are favorably 0.75 to 1.5 mm and more favorably 0.9 to 1.1 mm.

The balloon 103 has a front-end side bonding portion 103a and a rear-end side bonding portion 103b. The front-end side bonding portion 103a is fixed to the inner tube 112 at a position a little rearward from the front end thereof. The rear-end side bonding portion 103b is fixed to the front end of the outer tube 113. The balloon 103 communicates with the balloon-expanding lumen 116 at a position in the vicinity of the proximal end thereof.

A material having a certain degree of flexibility can be preferably used for the inner tube 112 and the outer tube 113. It is favorable to use thermoplastic resins such as polyolefin (for example, polyethylene, polypropylene, ethylene-propylene copolymer, ethylene-vinyl acetate copolymer), polyvinyl chloride, polyamide elastomer, and polyurethane; silicone rubber, and latex rubber. It is more favorable to use the thermoplastic resins. Polyolefin is most favorable of the thermoplastic resins.

Figure 19:
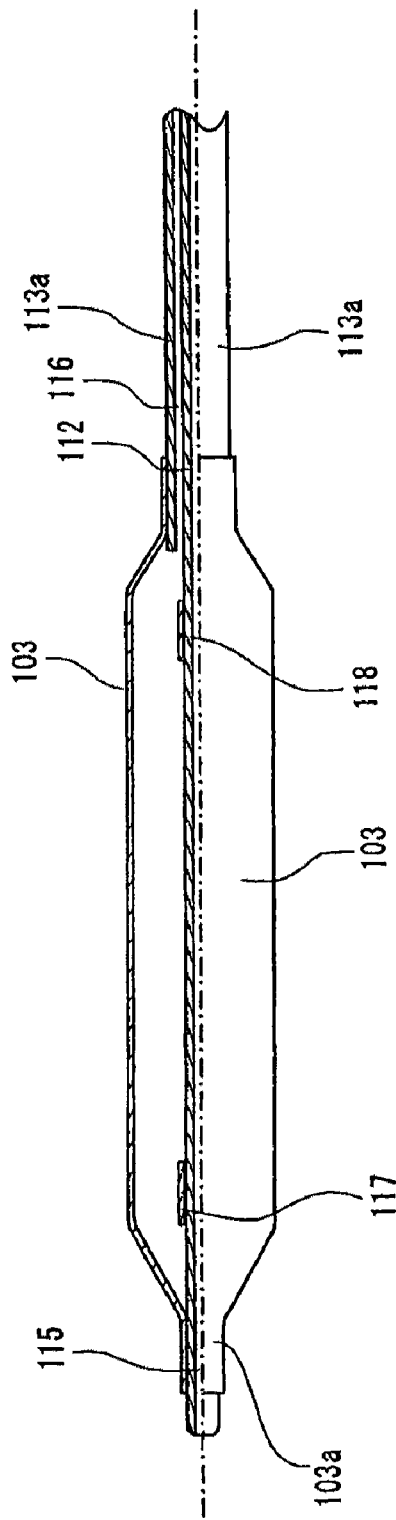
FIG. 19 is an explanatory view for describing the operation of the stent delivery device of an embodiment of the present invention.

As shown in FIG. 18, the balloon 103 is foldable. When the balloon 103 is not expanded, it can be folded over the outer surface of the inner tube 11. As shown in FIG. 19, the balloon 103 has a tubular (preferably, cylindrical) expandable portion having an approximately uniform diameter so that it is possible to expand the stent 1 to be mounted on the balloon 103. The expandable portion is not necessarily cylindrical but may be polygonal. As described above, the front-end side bonding portion 103a of the balloon 103 is liquid-tightly bonded to the inner tube 112, and the rear-end side bonding portion 103b thereof is liquid-tightly bonded to the front end of the outer tube 113 with an adhesive agent or by thermal fusion. The balloon 103 tapers between the expandable portion and each of the bonding portions 103a and 103b.

An expansion space 103c is formed between the inner surface of the balloon 103 and the outer surface of the inner tube 112. The entire circumference of the expansion space 103c communicates with the balloon-expanding lumen 116 at the rear end of the expansion space 103c. Because the expansion space 103c communicates with the balloon-expanding lumen 116 having a comparatively large volume, it is easy to inject an expansion fluid into the balloon 103 through the balloon-expanding lumen 116.

Materials having a certain degree of flexibility can be preferably used for the balloon 103. It is favorable to use thermoplastic resins such as polyolefin (for example, polyethylene, polypropylene, ethylene-propylene copolymer, ethylene-vinyl acetate copolymer, crosslinked ethylene-vinyl acetate copolymer), polyvinyl chloride, polyamide elastomer, polyurethane, polyester (for example, polyethylene terephthalate), polyarylane sulfide (for example, polyphenylene sulfide), silicone rubber, and latex rubber. It is particularly favorable to use an extensible material. A biaxially oriented material can be preferably used for the balloon 103 because of its high degree of strength and expansion.

Regarding the size of the balloon 103, the outer diameter of the expanded cylindrical portion (expandable portion) thereof is favorably in the range of 2 to 4 mm and more favorably 2.5 to 3.5 mm. The length of the balloon 103 is favorably in the range of 10 to 50 mm and more favorably in the range of 20 to 40 mm. The outer diameter of the front-end side bonding portion 103a is favorably in the range of 0.9 to 1.5 mm and more favorably in the range of 1 to 1.3 mm. The length of the front-end side bonding portion 103a is favorably in the range of 1 to 1 mm and more favorably 1 to 1.3 mm. The outer diameter of the rear-end side bonding portion 103b is favorably in the range of 1 to 1.6 mm and more favorably 1.1 to 1.5 mm. The length of the rear-end side bonding portion 103b is favorably in the range of 1 to 5 mm and more favorably in the range of 2 to 4 mm.

As shown in FIG. 18, the blood vessel expansion appliance 100 has two radiographing members 117, 118 fixed to the outer surface of the shaft body 102 at positions corresponding to one and other ends of the cylindrical portion (expandable portion) of the stent when the stent is expanded. Further the blood vessel expansion appliance 100 may have two radiographing members fixed to the outer surface of the shaft body (in this embodiment inner tube 112) 102 at positions corresponding to one and other ends of the central portion of the stent 201 having a predetermined length. Further the blood vessel expansion appliance 100 may have one radiographing member fixed to the outer surface of the shaft body 102 at a position corresponding to the central portion of the stent 201.

The radiographing members 117 and 118 are preferably in the shape of a ring having a predetermined length or a coiled wire. It is preferable that the radiographing members 117, and 118 are made of gold, platinum, tungsten or alloys thereof or a silver-palladium alloy.

The stent 201 is mounted on the balloon 103, with the stent covering the folded balloon 103. The stent is formed by processing a metal pipe having an inner outer diameter smaller than the inner diameter of the stent at the time when the stent is expanded and larger than the outer diameter of the folded balloon. The balloon is inserted into the formed steno and a force is uniformly applied to the outer surface of the stent to decrease the diameter of the stent. In this manner, the production of the stent is completed. That is, production of the stent 201 is completed when the stent 201 is mounted on the balloon by compressing the stent.

A linear rigidity-imparting member (not shown) may be inserted between the inner tube 112 and the outer tube 113, namely, into the balloon-expanding lumen 116. The rigidity-imparting member prevents excess bending of the body 102 of the stent delivery device 100 at bent portions of blood vessels without much deteriorating the flexibility of the stent delivery device 100 and facilitates the insertion of the frond end of the stent delivery device 100 into the bent portions of blood vessels. It is preferable that the diameter of the frond end of the rigidity-imparting member is set smaller than those of the other portions thereof by grinding or the like. It is preferable that front end of the small-diameter portion extends to the vicinity of the front end of the outer tube 113 of the body of the stent delivery device 100. It is preferable that the rigidity-imparting member 133 consists of a metal wire having a diameter 0.05 to 1.50 mm and more favorably 0.10 to 1.00 mm. The rigidity-imparting member 133 is made of favorably an elastic metal such as stainless steel or a super elastic alloy and more favorably high-strength stainless steel for a spring or a wire of the super elastic alloy.

As shown in FIG. 17, the stent delivery device 100 of this embodiment has a branched hub 110 fixed to the rear end thereof. The branched hub 110 has an inner-tube hub, fixed to the inner tube 112, which communicates with the guide wire lumen 115 and has a guide wire introducing opening 109 forming a guide wire port; and an outer-tube hub, fixed to the outer tube 113, which communicates with the balloon-expanding lumen 116 and has an injection port 111. The outer-tube hub and the inner-tube hub are fixed to each other. As the material of the branched hub 110, thermoplastic resin such as polycarbonate, polyamide, polysulfone, polyacrylate, and methacrylate-butylene-stylene copolymer can be preferably used.

The construction of the stent delivery device is not limited to the above-described one. For example, the stent delivery device may have a guide wire insertion opening, communicating with the guide wire lumen, disposed at a central portion thereof.

The stent of the present invention to be implanted in the organism has a plurality of the wavy annular members arranged adjacently to each other in the axial direction of the stent, with the adjacent wavy annular members connected with each other. Each of the wavy annular members has a plurality of the one-end side bent portions each having the apex at the one-end side of the stent in the axial direction thereof and a plurality of the other-end side bent portions each having the apex at the other-end side of the stent in the axial direction thereof. The apex of each of the one-end side bent portions of each wavy annular member penetrates into the space formed between the adjacent other-end side bent portions of one of the adjacent wavy annular members, and the apex of each of the other-end side bent portions of each wavy annular member penetrates into the space formed between the adjacent one-end side bent portions of the other of the adjacent wavy annular members. The apex of the one-end side bent portion of each wavy annular member and the apex of the other-end side bent portion of the adjacent wavy annular member curve in different directions in the circumferential direction of the stent.

The apex of the one-end side bent portion of each wavy annular member and the apex of the other-end side bent portion of the adjacent wavy annular member curve in different directions in the circumferential direction of the stent. Thereby the stratum of the stent hardly flares outward and favorably follows travel directions of blood vessels. Because each annular member is composed of wavy line elements, each annular member is flexible and easy to bend uniformly.

Further because the apex of the one-end side bent portion and that of the other-end side bent portion curve in different directions in the circumferential direction of the stent the apexes of the one-end side and other-end side bent portions penetrate into large spaces between the bent portions of the adjacent annular member. Thereby the stent has a high expanded state retention force.

A stent of another embodiment of the present invention is described below.

Figure 32:
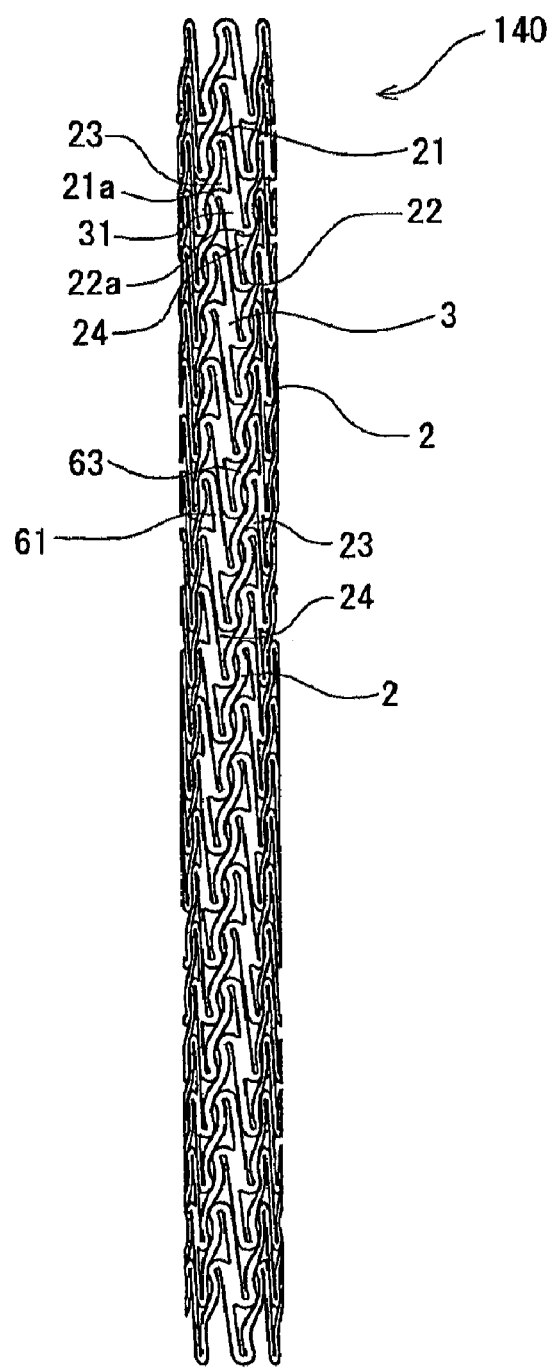
FIG. 32 is a front view showing a stent of another embodiment of the present invention.
Figure 33:
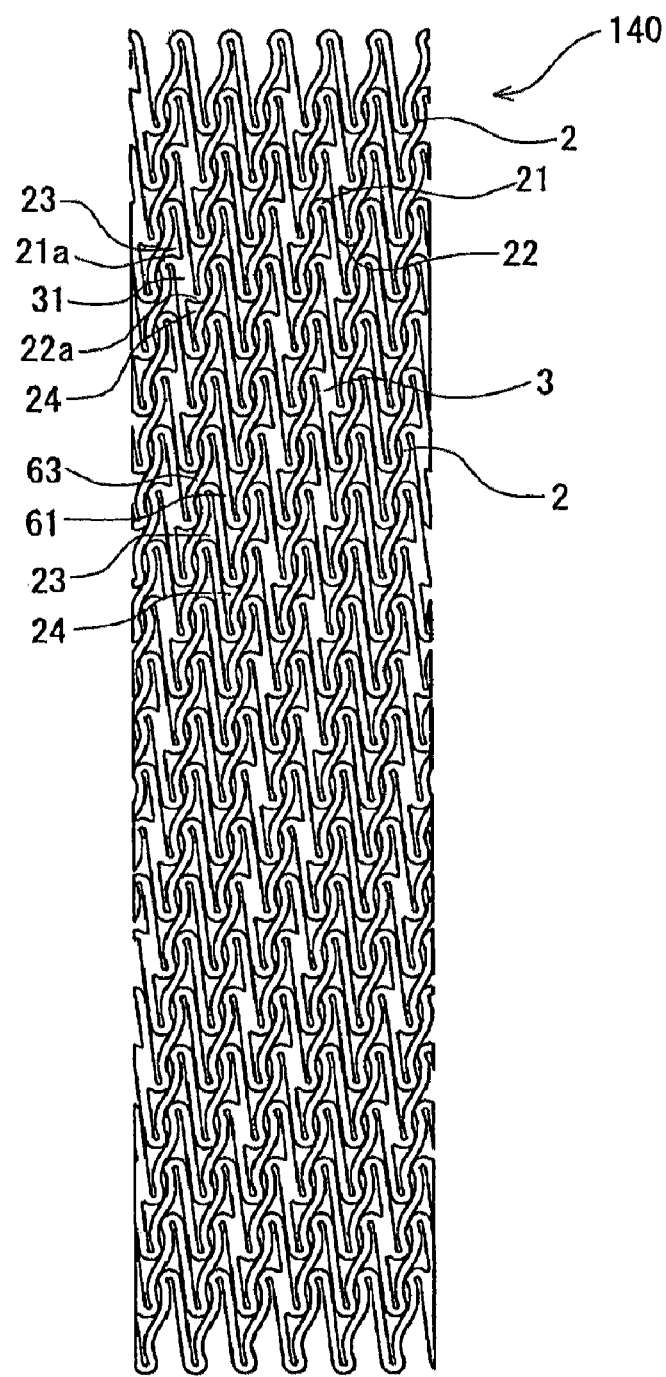
FIG. 33 is a development view showing the stent shown in FIG. 32.
Figure 34:
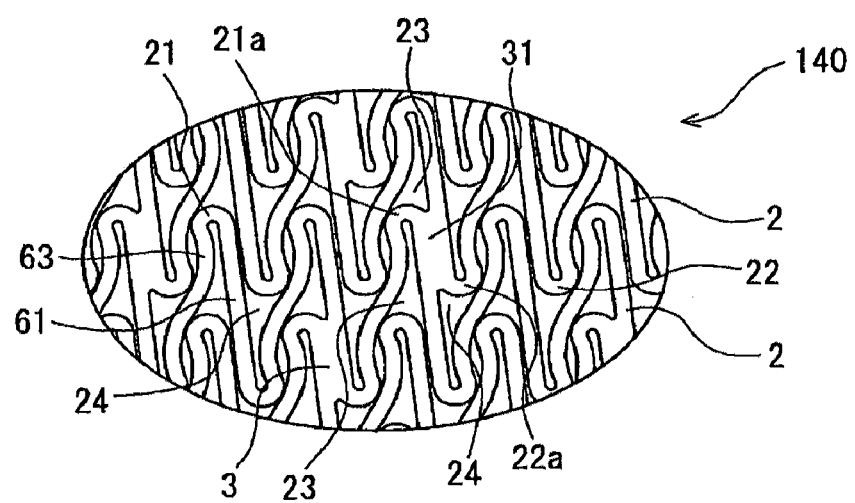
FIG. 34 is a partly enlarged view showing the stent of FIG. 33.
Figure 35:
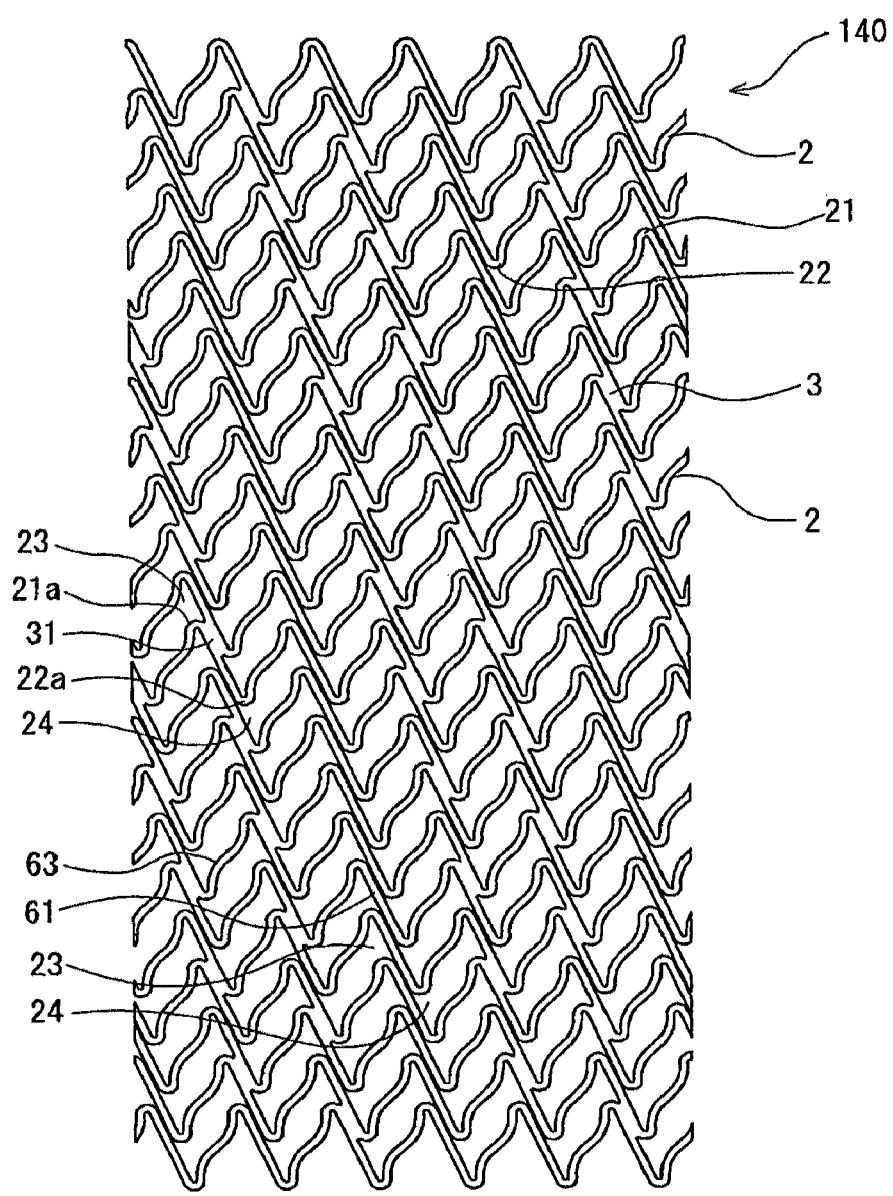
FIG. 35 is a development view showing the stent shown in FIG. 32 immediately after the stent is manufactured.

FIG. 32 is a front view showing a stent of another embodiment of the present invention. FIG. 33 is a development view showing the stent shown in FIG. 32. FIG. 34 is a partly enlarged view showing the stent of FIG. 33. FIG. 35 is a development view showing the stent shown in FIG. 32 immediately after the stent is manufactured.

A stent 140 of the present invention to be implanted in an organism has a large number of wavy annular members 2 arranged adjacently to each other in an axial direction thereof with the adjacent wavy annular members 2 connected with each other. The stent 140 has not less than 13 wavy annular members 2 per 10 mm in the axial direction thereof.

The stent 140 is formed substantially as a tube and has a diameter whose dimension is so set that it can be inserted into a lumen of a predetermined portion inside an organism. The stent 140 can be expanded when a force spreading radially outward from the inside of the tube is applied thereto. The stent 140 is a so-called balloon expandable stent.

As shown in FIGS. 32 and 33, the stent 140 of the present invention has a plurality of the wavy annular members 2 arranged adjacently to each other in the axial direction thereof, with the adjacent wavy annular members connected with each other.

In this stent 140, each of the wavy annular members 2 has a plurality of one-end side bent portions 21 each having an apex at one-end side of the stent 140 in an axial direction thereof and a plurality of other-end side bent portions 22 each having an apex at the other-end side of the stent 140 in the axial direction thereof. An apex 21a of each of the one-end side bent portions 21 of each wavy annular member 2 penetrates into a space 23 formed between the adjacent other-end side bent portions 22 of one of the adjacent wavy annular members 2. An apex 22a of each of the other-end side bent portions 22 of each wavy annular member 2 penetrates into a space 24 formed between the adjacent one-end side bent portions 21 of the other of the adjacent wavy annular members 2.

The apex 21a of the one-end side bent portion 21 of each of the wavy annular members 2 and the apex 22a of the other-end side bent portion 22 of the adjacent wavy annular member 2 curve in an approach direction, thus engaging each other.

The number of the wavy annular members 2 forming the stent 140 shown in FIG. 32 is set to 23. The number of the wavy annular members 2 is favorably in the range of 13 to 50 and more favorably in the range of 10 to 35, although the number thereof is different in dependence on the length of the stent.

The stent 170 has not less than 13 wavy annular members 2 per 10 mm in the axial direction thereof and is set to favorably 13 to 16. The length of the wavy annular member 2 in the axial direction of the stent is set to favorably 0.25 to 1.25 mm and especially favorably 0.10 to 0.12 mm. The diameter of the stent when it is not expanded (when the stent is not mounted on balloon) is set to favorably 0.5 to 1.5 mm and especially favorably 0.8 to 1.2 mm. The length of the stent when it is not expanded (when the stent is mounted on balloon) is set to favorably 5 to 40 mm and especially favorably 8 to 30 mm. The number of the apexes of the one-end side bent portions of each wavy annular member and that of the apexes of the other-end side bent portions thereof are set to favorably 6 to 18 and especially favorably 6 to 12. The line width of the wavy annular member is set to favorably 0.05 to 0.15 mm and especially favorably 0.7 to 0.12 mm.

Each of the wavy annular members 2 has a plurality of one-end side bent portions 21 each having an apex at one end side of the stent 140 in an axial direction thereof and a plurality of other-end side bent portions 22 each having an apex at the other-end side of the stent 140 in the axial direction thereof. Each of the wavy annular members 2 is composed of an endless wavy line element. The one-end side bent portions 21 and the other-end side bent portions 22 are formed alternately. The number of the one-end side bent portions 21 and that of the other-end side bent portions 22 are equal to each other. The number of the one-end side bent portions 21 (the other-end side bent portions 22) of each of the wavy annular members 2 shown in FIG. 32 is set to six.

In a wavy line element forming the wavy annular member 2 of the stent 140 of this embodiment a curved portion thereof and a straight-line portion thereof are connected to each other at the apex.

In the stent 140 of this embodiment a stratum portion connecting the apexes 21*a*, 22*a* of the annular member 2 to each other is constructed of an inclined straight-line portion 61 and an S-shaped portion 63. In other words, the apexes 21*a*, 22*a* connect the inclined straight-line portion 61 and the S-shaped portion 63 to each other. It is possible that the wavy annular member is continuously curved and does not substantially have the straight-line portion. The end-side bent portions of the wavy annular members 2 disposed at both ends of the stent 140 may be wider than other bent portions.

As shown in FIGS. 33 and 34, the apex 21*a* of each of the one-end side bent portions 21 of each wavy annular member 2 penetrates into the space 23 formed between the adjacent other-end side bent portions 22 of one of the adjacent wavy annular members 2. Similarly the apex 22*a* of each of the other-end side bent portions 22 of each wavy annular member 2 penetrates into the space 24 formed between the adjacent one-end side bent portions 21 of the other of the adjacent wavy annular members 2. That is, the adjacent wavy annular members 2 overlap each other in the axial direction of the stent 140. The axial length of the overlapped portion (in other words, engaging portion which will be described later) of the wavy annular member 2 is favorably not less than 0.1 mm, more favorably not less than 0.1 mm nor more than 0.8 mm, and most favorably not less than 0.2 mm nor more than 0.4 mm. The axial distance (when the stent is mounted on a balloon, which will be described later) between proximate apexes of the adjacent wavy annular members is favorably not less than 0.1 mm, more favorably not less than 0.1 mm nor more than 0.8 mm, and most favorably not less than 0.2 mm nor more than 0.4 mm.

The apex 21*a* of the one-end side bent portion 21 of each of the wavy annular members 2 and the apex 22*a* of the other-end side bent portion 22 of the adjacent wavy annular member 2 curve, thus engaging each other. More specifically, the one-end side bent portion 21 of the wavy annular member 2 which penetrates into the space formed between the adjacent wavy annular members 2 curves, whereas the other-end side bent portion 22 engaging the one-end side bent portion 21 curves in a direction opposite to the direction in which the one-end side bent portion 21 curves. Thus the one-end side bent portion 21 and the other-end side bent portion 22 curve in the approach direction. Because the apex 21*a* of the one-end side bent portion 21 and the apex 22*a* of the other-end side bent portion 22 slightly engage each other, the stent 140 displays a high expansion retention force when it expands. When the stent 140 is bent at a bent portion of a blood vessel, it is possible to prevent the apexes from colliding with each other. Thereby the stent 140 displays a high flexibility.

The adjacent wavy annular members 2 are connected to each other by a connection portion 3. The stent 140 of this embodiment has the connection portion 3 disposed toward one or other-end side of the stent 140 to some extent in the axial direction thereof with respect to the apex 21*a* of the one-end side bent portion 21 of the wavy annular member 2 and with respect to the apex 22*a* of the other-end side bent portion 22 of the adjacent wavy annular member 2. In other words, the connection portion 3 is shifted to some extent from the apexes 21*a* and 22*a* of the one-end side bent portion 21 and the other-end side bent portion 22. In other words, the connection portion 3 is shifted toward the one or other end of the stent with respect to the apexes 21*a* and 22*a* of the one-end side bent portion 21 and the other-end side bent portion 22.

Therefore it is possible to decrease the degree of contraction (shortening) of the whole length of the stent when the stent expands. The apexes of the adjacent bent portions do not face each other but nest each other. Therefore when the stent bends at the bent portion of the blood vessel, the stent passes through the bent portion of the blood vessel with a high flexibility without the apexes colliding with each other. Because the connection portion is formed at the position shifted from the apexes, the stent is allowed to expand uniformly and keep its strength in a favorable balance. When the apexes are connected with each other by the connection portion, there is a difference in strength between the bent portion where the connection portion is present and the bent portion where the connection portion is not present. Consequently there is a possibility that the expanded states of the bent portions become nonuniform and that there occurs a nonuniform distribution of strength in the entire stent.

In the stent 140 of this embodiment the connection portion 3 connects a back-side position of a portion where the apex 21*a* of the one-end side bent portion 21 of one wavy annular member 2 and the apex 22*a* of the other-end side bent portion 22 of the adjacent wavy annular member 2 are dose to each other and engage each other. In the stent 140, the connection portion is formed as a back-side position connection portion 31. By connecting the apex 21*a* of the one-end side bent portion 21 and the apex 22*a* of the other-end side bent portion 22 to each other at the back-side position of the portion in the neighborhood of the apexes 21*a* and 22*a* engaging each other, the apexes are not prevented from opening when the stent is expanded.

The connection portion 3 is formed obliquely at a predetermined angle to the axial direction of the stent 140. Therefore in the entire stent the rate of the connection portion which little contributes to the expanded-state retention force when the stent is expanded is low. Thus the stent displays a high expanded-state retention force as a whole. A plurality of the connection portions 3 (two in this embodiment) is formed between the adjacent wavy annular members 2. The number of the connection portions to be formed between the adjacent wavy annular members 2 may be one or not less than three.

The stent 140 is formed in a state as shown in FIG. 35 which is a developed view. The stent 140 has a larger outer diameter in the state shown in FIG. 35 than in the state shown in FIGS. 32 and 33. Thereafter the stent 140 is mounted on an expandable balloon of an organism expansion appliance by reducing the outer diameter of the stent 140. By expanding the balloon, the outer diameter of the stent 140 is extended larger than that at the time when the stent 140 has the state as shown in FIG. 35. Even in the state in which the outer diameter of the stent 140 is increased, each wavy annular member maintains its fundamental skeleton, and the bent portions keep inside the space formed between the adjacent bent portions of the adjacent wavy annular member. The wavy line element constituting the annular member deforms but keeps wavy.

Figure 36:
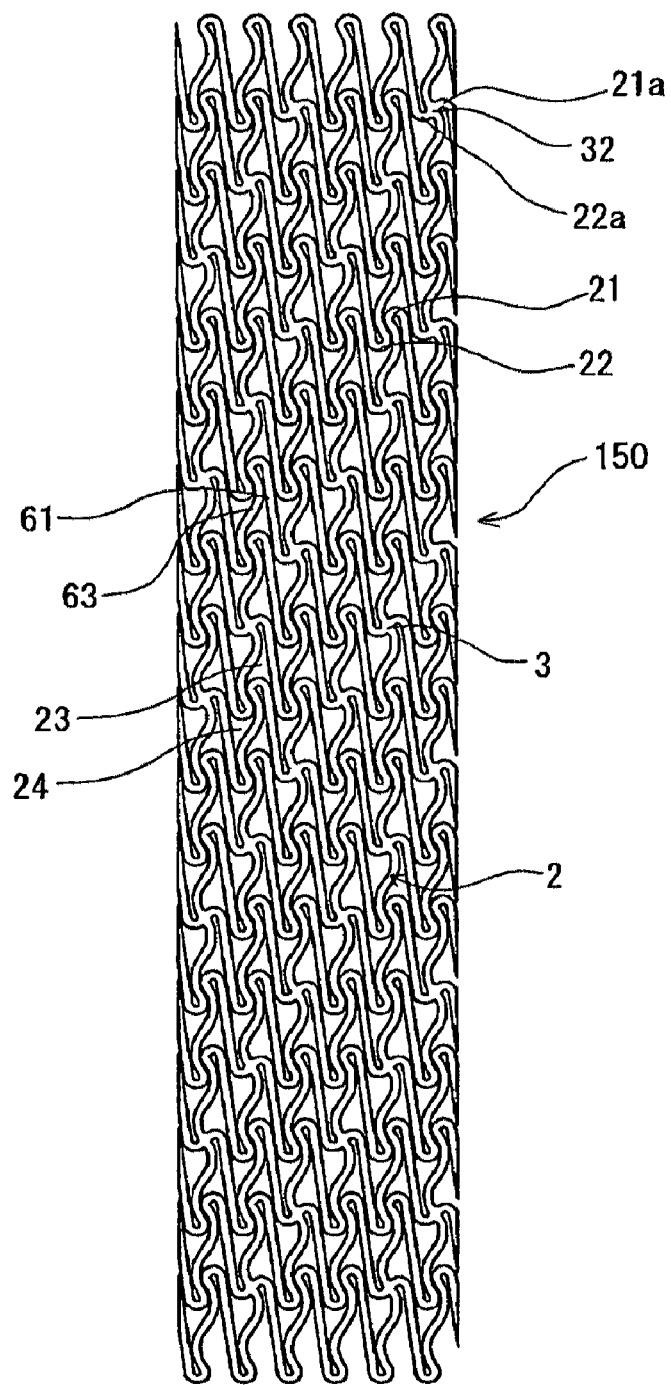
FIG. 36 is a development view showing a stent of another embodiment of the present invention.
Figure 37:
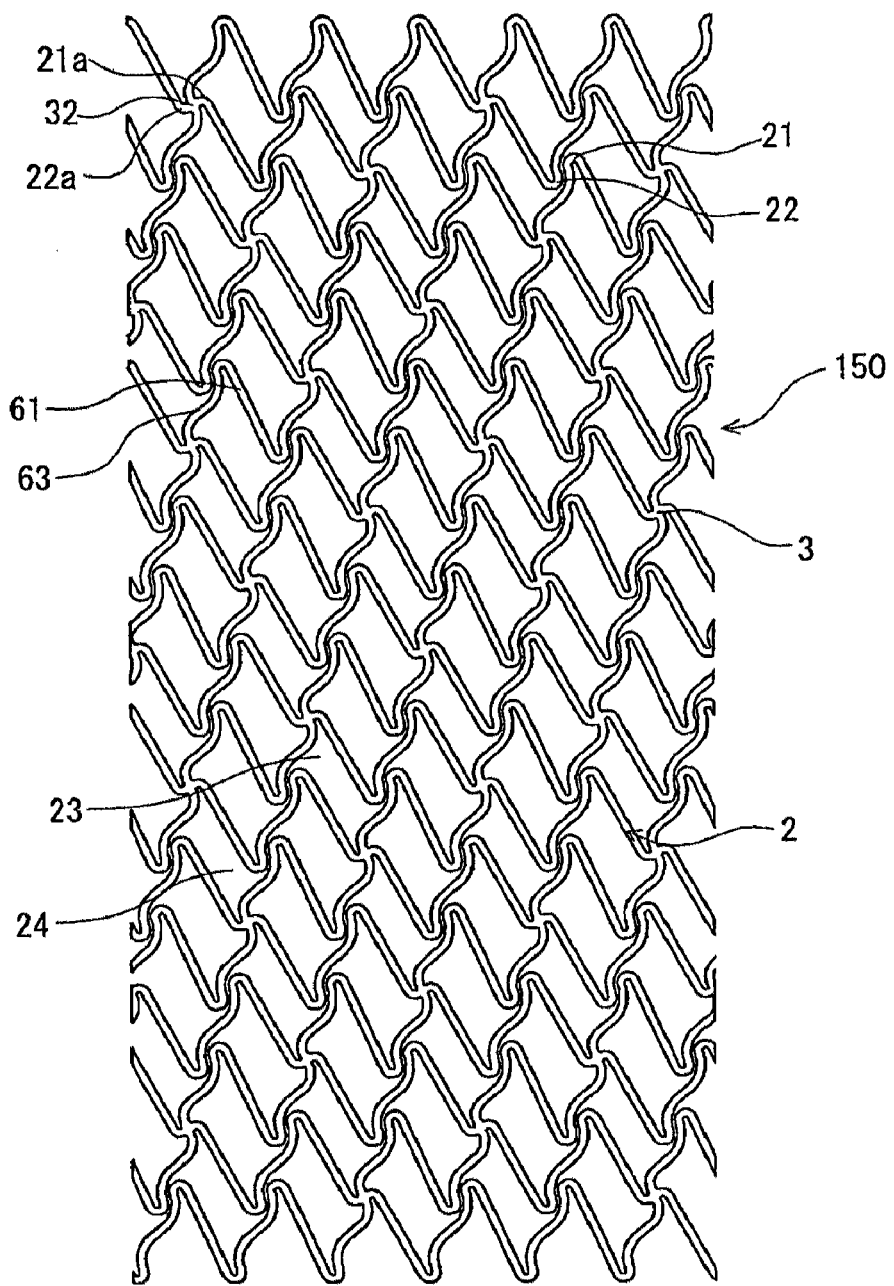
FIG. 37 is a development view showing the stent shown in FIG. 36 immediately after the stent is manufactured.

The stent may be a stent 150 shown in FIGS. 36 and 37. FIG. 36 is a development view showing a stent of another embodiment of the present invention to be implanted in an organism. FIG. 37 is a development view showing the stent shown in FIG. 36 immediately after the stent is manufactured.

In the stent 150 of this embodiment the connection portion 3 is formed as an engaged-position connection portion 32 disposed at a position where the apex 21a of the one-end side bent portion 21 of one wavy annular member 2 and the apex 22a of the other-end side bent portion 22 of the adjacent wavy annular member 2 are close to each other and engage each other. In other points, the stent 150 is identical to the above-described stent 140. By forming the connection portion at the position where the apexes engage each other, the apexes engage each other at a stent-mounting time. Thereby it is possible to strengthen a force of holding the stent on the balloon and prevent a drop of the wavy annular member at a stent delivery time.

Figure 38:
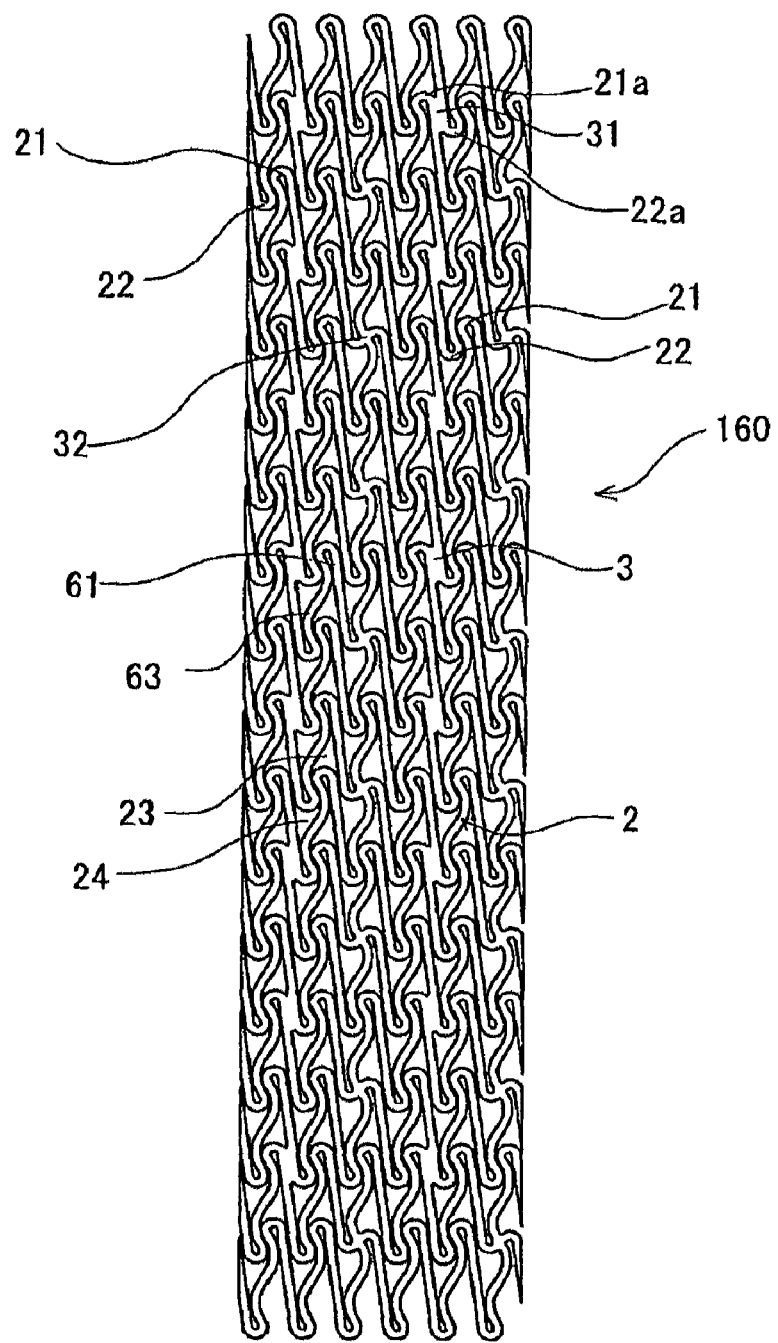
FIG. 38 is a development view showing a stent of another embodiment of the present invention.
Figure 39:
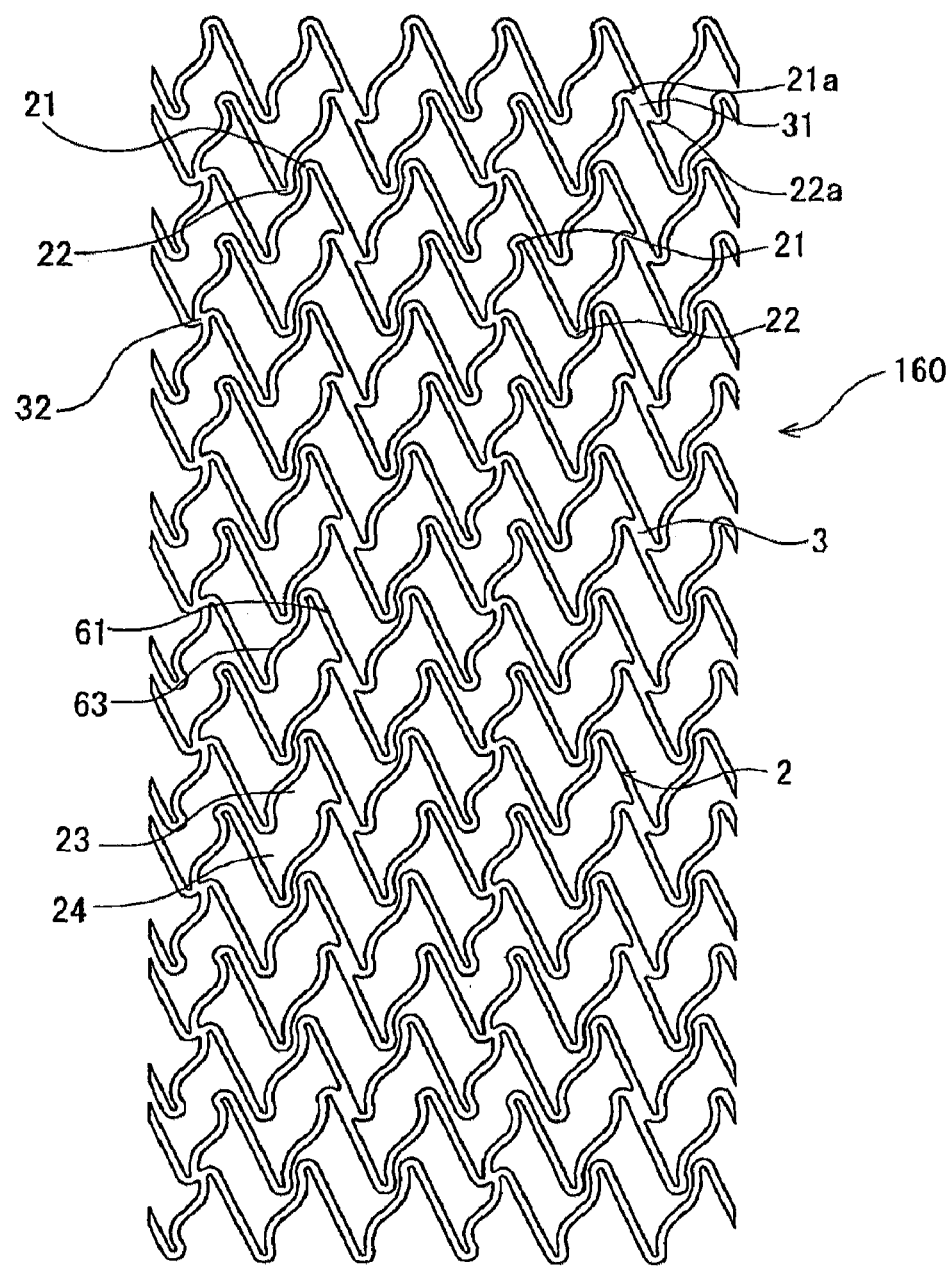
FIG. 39 is a development view showing the stent shown in FIG. 38 immediately after the stent is manufactured.

A stent of present invention may be a stent 160 shown in FIG. 38 and FIG. 39.

FIG. 38 is a development view showing a stent of another embodiment of the present invention FIG. 39 is a development view showing the stent shown in FIG. 38 immediately after the stent is manufactured.

The stent 160 of this embodiment has both types of connection portions, a rear portion connection type connection portion 31 and an engaging position connection type connection portion 32. The rear portion connection type connection portion 31 is formed at the position on the rear of the portion where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other. The engaging position connection type connection portion 32 is formed at the position where the apex 21a of the one-end side bent portion 21 of one wavy annular member 2 and the apex 22a of the other-end side bent portion 22 of the adjacent wavy annular member 2 are proximate to each other, with the apexes 21a and 22a engaging each other.

In the stent 160 of this embodiment, an annular unit composed of two wavy annular members 2 connected with each other by the rear portion connection type connection portion 31 is connected with an adjacent annular unit by the engaging position connection type connection portion 32. That is, the rear portion connection type connection portion 31 and the engaging position connection type connection portion 32 are alternately formed in the axial direction of the stent 160.

In the stent 160 of this embodiment two rear portion connection type connection portion 31 are formed for one wavy annular member, with the rear portion connection type connection portions 31 substantially opposed to each other with respect to the axis of the stent 160. The rear portion connection type connection portions 31 are disposed linearly in the axial direction of the stent 160. Similarly in the stent 160 of this embodiment two engaging position connection type connection portion 32 are formed for one wavy annular member, with the engaging position connection type connection portion 32 substantially opposed to each other with respect to the axis of the stent 160. The engaging position connection type connection portions 32 are uncontinuously and linearly formed in the axial direction of the stent 160.

The two rear portion connection type connection portions 31 of the wavy annular member 2 and the two engaging position connection type connection portions 32 of the adjacent wavy annular member 2 are substantially equiangularly disposed with respect to the axis of the stent 160. That is, in the stent 160, the adjacent wavy annular members 2 are connected to each other by the rear portion connection type connection portions 31 or the engaging position connection type connection portions 32, with the rear portion connection type connection portions 31 and the engaging position connection type connection portions 32 arranged alternately in the axial direction of the stent 160. In the stent 160, the adjacent wavy annular members 2 are connected to each other by a plurality of the rear portion connection type connection portions 31 or a plurality of the engaging position connection type connection portions 32, with the rear portion connection type connection portions 31 and the engaging position connection type connection portions 32 arranged alternately in the axial direction of the stent 160.

Figure 40:
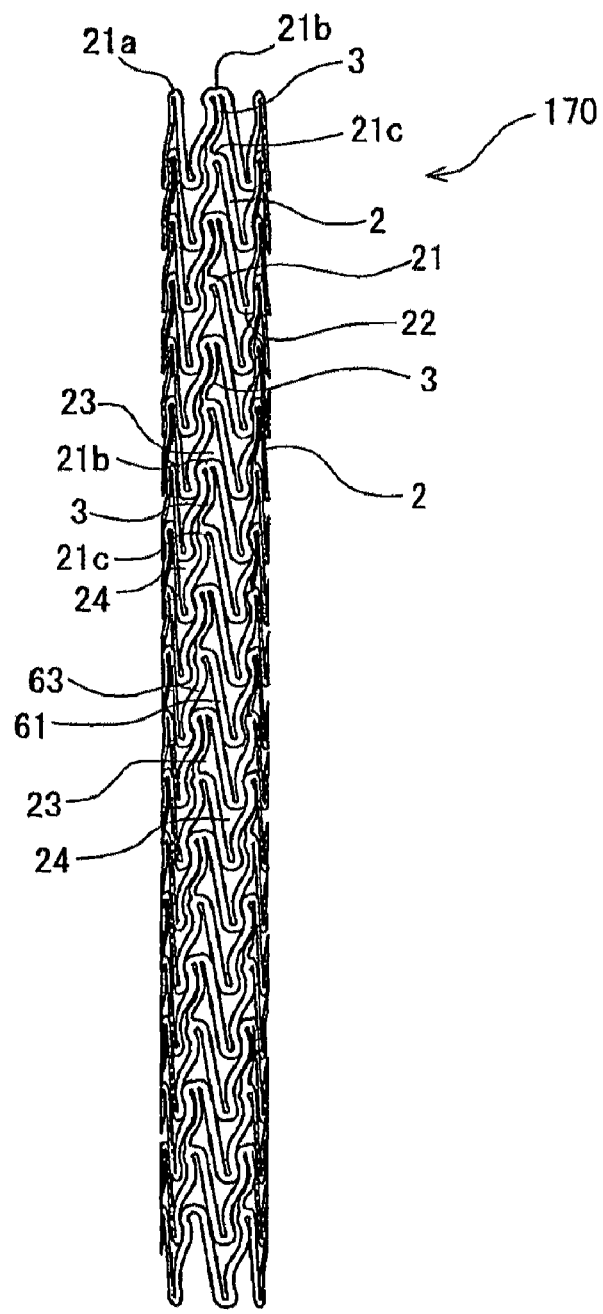
FIG. 40 is a development view showing a stent of another embodiment of the present invention.
Figure 41:
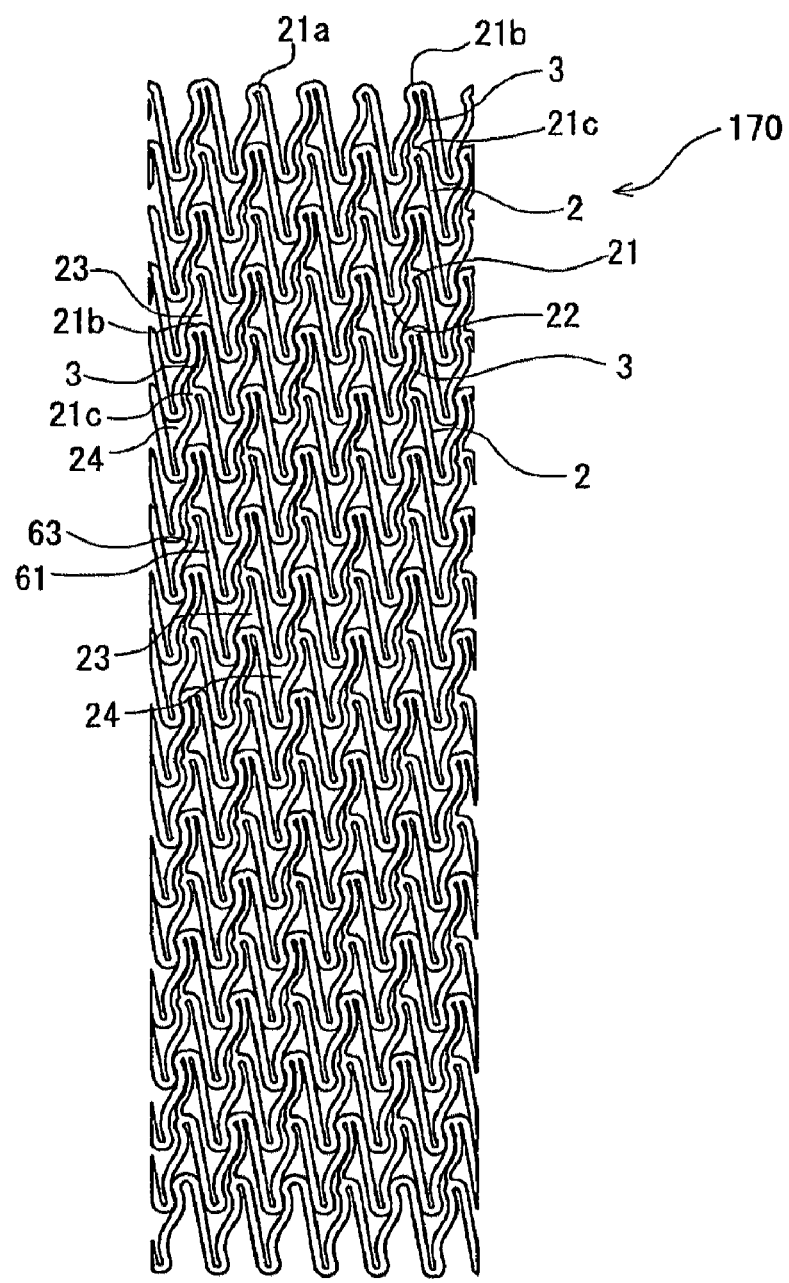
FIG. 41 is a development view showing the stent shown in FIG. 40.
Figure 42:
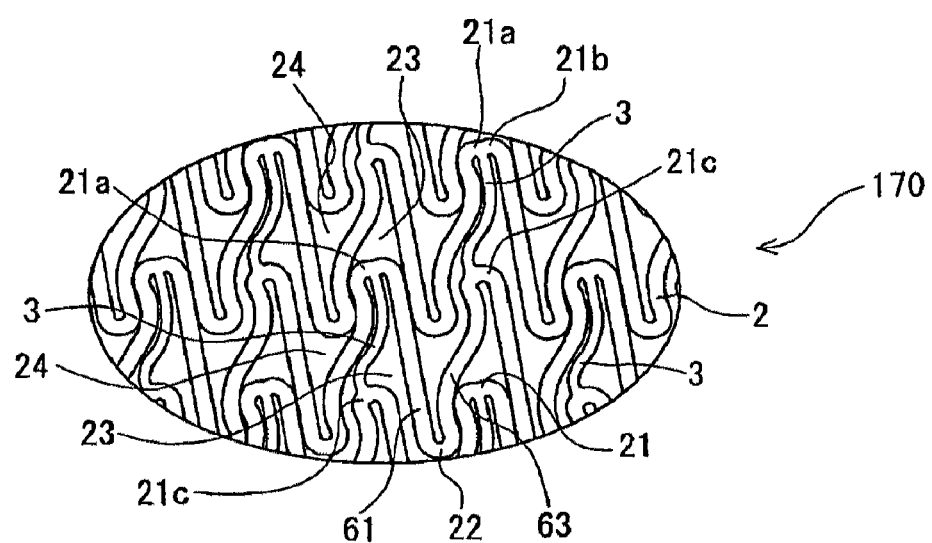
FIG. 42 is a partly enlarged view showing the stent of FIG. 41.
Figure 43:
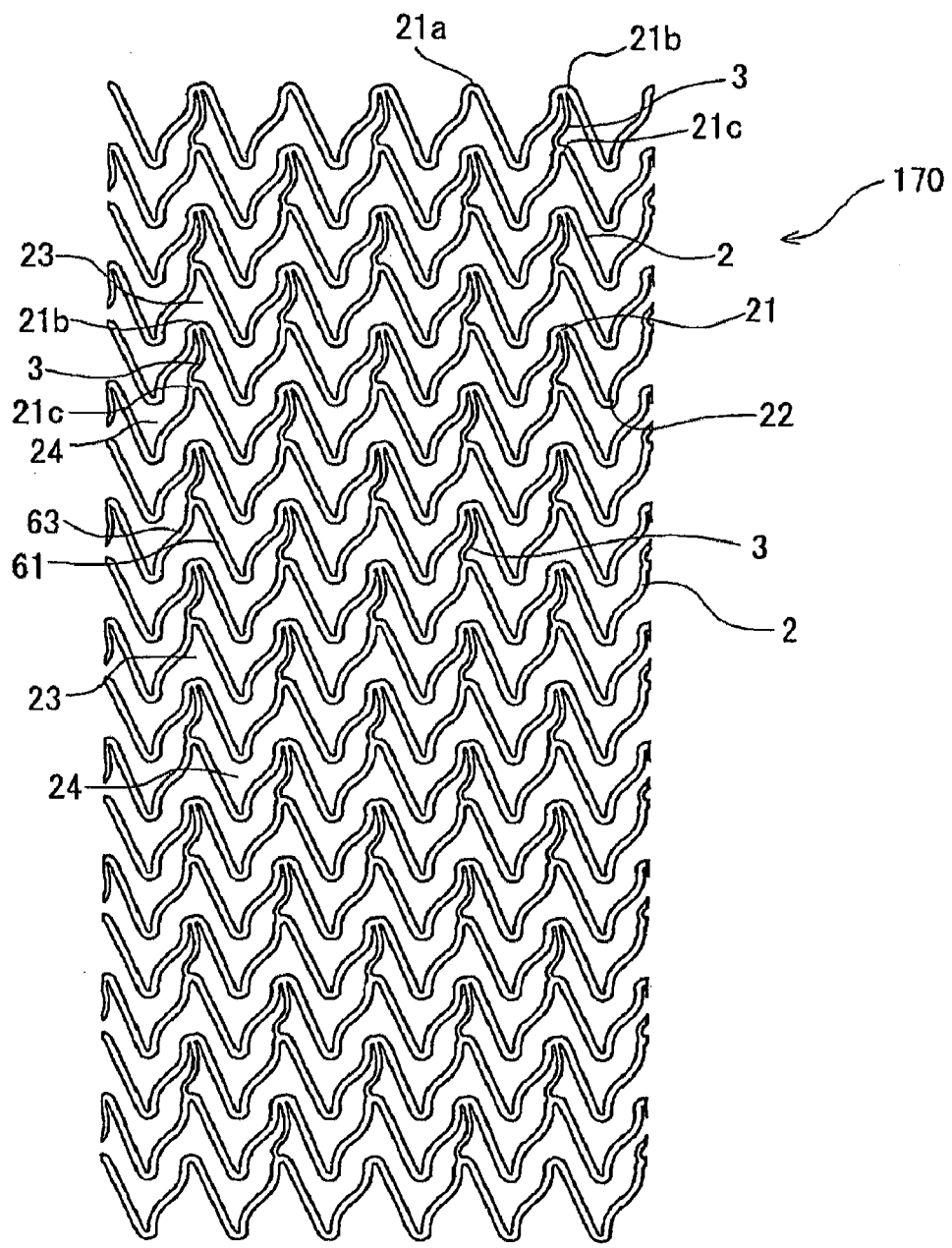
FIG. 43 is a development view showing the stent shown in FIG. 32 immediately after the stent is manufactured.

The stent may be a stent 170 shown in FIGS. 40 through 43. FIG. 40 is a front view showing a stent of another embodiment of the present invention to be implanted in an organism. FIG. 41 is a development of view showing the stent shown in FIG. 40. FIG. 42 is a partly enlarged view of FIG. 41. FIG. 43 is a development view showing the stent shown in FIG. 40 immediately after the stent is manufactured.

Similarly to the above-described stent 140, the stent 170 of this embodiment to be implanted in the organism has a large number of wavy annular members 2 arranged adjacently to each other in an axial direction thereof with the adjacent wavy annular members 2 connected with each other. The stent 170 has not less than 13 wavy annular members 2 per 10 mm in the axial direction thereof. The stent 170 of this embodiment is substantially different from the above-described stent 140 in the form of the connection portion 3.

As shown in FIGS. 40 through 43, the connection portion 3 connects the apexes 21a of the one-end side bent portions 21 of the adjacent wavy annular members to each other. Instead of connecting the apexes 21a of the one-end side bent portions 21 to each other, the connection portion 3 may connect the apexes 22a of the other-end side bent portions 22 to each other.

As shown in FIG. 42, in the stent 170, each wavy annular member 2 (in this embodiment, proximal-side wavy annular member 2 is excluded) has an inner-side connection apex 21b formed by extending one end of the connection portion 3 from an inner side thereof to the other side thereof. Three linear portions are extended from the inner side connection apex 21b to the proximal side.

Each wavy annular member 2 (in this embodiment one-end side wavy annular member is excluded) has an outer-side connection apex 21c at which the other end of the connection portion 3 is connected outward.

A portion of the wavy annular member close to the connection portion 3 connecting the apexes to each other is curved. The connection portion 3 has a curved configuration corresponding to a curved configuration of the wavy annular member. More specifically, the portion of the wavy annular member (one side (more specifically, left side) of the connection portion 3 in FIG. 41) dose to the connection portion 3 is curved. The connection portion 3 is curved in correspondence to the curved configuration of the wavy annular member. In other words, the connection portion 3 is curved in a radius of curvature similar to that of the curved portion of the wavy annular member in the same direction as the direction in which the wavy annular member is curved.

By forming the curved connection portion, it is possible to improve the flexibility of the entire stent decrease the degree of the overlapping of the linear portions when the stent is mounted on a balloon (when the diameter of the stent is decreased), and decrease the outer diameter (outer diameter of the stent when the diameter of the stent is decreased) of the stent when the stent is mounted on the balloon. By connecting the apexes to each other, it is possible to prevent the stent from being shortened in the axial length thereof.

In the stent 170 of this embodiment the wavy annular member has a plurality of the connection portions 3 (more specifically, three). The connection portions are formed almost equiangularly to the axis of the stent. Two connection portions or one connection portion may be formed. The connection portions are disposed uncontinuously in the axial direction of the stent 170. More specifically, the connection portions adjacent to each other in the axial direction of the stent 170 are shifted from each other so that they are uncontinuous in the axial direction thereof. The line width of the wavy line element at the connection portion is set to favorably 0.4 to 1.2 mm and especially favorably 0.5 to 0.8 mm. As shown in FIGS. 40 through 43, it is preferable that the line width of the wavy line element at the connection portion is smaller than that of the wavy annular member. More specifically, it is preferable that the line width of the wavy line element at the connection portion is set to ½ to ¾ of the line width of the wavy annular member.

It is preferable that each of the stents of the above-described embodiments is formed as a tube, has a diameter whose dimension is so set that it can be inserted into the lumen of the predetermined portion inside the organism, and can be expanded when a force spreading radially outwardly from the inside of the tube is applied thereto. That is, it is preferable that the stents are balloon expandable stents.

It is preferable that the material of the balloon expandable stent has a certain degree of compatibility with the organism. For example, it is possible to use stainless steel, tantalum or tantalum alloys, platinum or platinum alloys, gold or gold alloys, cobalt based alloys, a cobalt-chrome alloy, a titanium alloy, and a niobium alloy. It is preferable to plate the stent with a noble metal such as gold and platinum after the stent is fabricated into a final shape. As the stainless steel, SUS 316L most corrosion-resistant can be preferably used.

It is preferable to anneal the stent after a final configuration thereof is formed.

Annealing improves the flexibility and plasticity of the entire stent. Thereby the stent can be favorably implanted at a curved portion of a blood vessel. As compared with a non-annealed stent the annealed stent has a lower force of restoring to an original state after it is expanded, and especially has a lower force of restoring to an original linear state when it is expanded at the curved portion of the blood vessel. This minimizes physical stimulation to the inner wall of the curved portion of the blood vessel, thus reducing the cause of a recurrence of stenosis. It is preferable to anneal the stent by heating it to 900 to 1200° C. in an inert gas atmosphere (e.g., a mixture gas of nitrogen and hydrogen) so that no oxide film is formed on the surface of the stent and then slowly cooling it.

The stent is formed by removing portions of a tube (more specifically, metal pipe) other than a portion constituting a frame structure. More specifically, the stent is formed by removing unnecessary portions from the metal pipe by an etching method called photo-fabrication in which masking and chemicals are used, electric discharge method in which a die is used or cutting (for example, mechanical polishing, laser cutting processing). It is preferable to polish the edge of the frame structure by using chemical polishing or electropolishing after the frame structure is formed. Stent is formed by removing (for example, cutting, dissolving) a part of a pipe made of the super-elastic metal, not constituting the stent. Thereby the stent is obtained as an integral product. The pipe made of the super-elastic metal to be used to form the stent of the present invention can be produced by dissolving the super-elastic alloy such as the Ti—Ni alloy in an inactive gas atmosphere or a vacuum atmosphere to form an ingot thereof, polishing the ingot mechanically, forming a pipe having a large diameter by hot press and extrusion, repeating a drawing step and a heat treatment step to adjust the diameter and thickness of the pipe to a predetermined thickness and reduced diameter, and finally polishing the surface of the pipe chemically or physically. The pipe made of the super-elastic metal can be processed into the base material for the stent by a cutting work such as laser processing (for example, YAG laser), electrical discharge machining, chemical etching, cutting processing or in combination thereof.

The stent of the present invention may be coated with a material suitable for the organism on its inner surface, outer surface or inner and outer surfaces. As the material suitable for the organism, synthetic resin and metal suitable for the organism can be used. The following inactive metals are used to coat the surface of the stent gold by an electroplating method, stainless steel by an evaporation method, silicon carbide by a sputtering method, diamond-like carbon, plated titanium nitride, and plated gold. As the synthetic resin, the following thermoplastic resins or thermosetting resins can be used: polyolefin (for example, polyethylene, polypropylene, ethylene-propylene copolymer), polyvinyl chloride, ethylene-vinyl acetate copolymer, polyamide elastomer, polyurethane, polyester, fluorocarbon resin, silicone resin. It is preferable to use polyolefin, polyamide elastomer, polyester, polyurethane, silicone resin. A resin decomposable in the organism (polylactic acid, polyglycolic acid, polylactic acid-polyglycolic acid copolymer) is also favorable. It is preferable that a film of the synthetic resin is soft to such an extent as not to prevent a frame constituting the stent from being curved. The thickness of the film of the synthetic resin is favorably in the range of 3 to 300 μm and more favorably in the range of 5 to 100 μm.

As the method of thinly coating the surface of the stent with the synthetic resin, it is possible to use a method of inserting the stent into the melted synthetic resin or into the synthetic resin dissolved in a solution. It is also possible to use a chemical evaporation method of polymerizing a monomer over the surface of the pipe made of the superelastic metal. In the case where the surface of the stent is coated very thinly with the synthetic resin, the use of a dilute solution or the chemical evaporation method is preferable. To improve the quality of the material suitable for the organism to a higher extent the resinous film may be coated with an anti-thrombus material or the anti-thrombus material may be fixed to the resinous film. As the anti-thrombus material, known various resins can be used singly or as a mixture thereof. For example, polyhydroxyethyl methacrylate, a copolymer of hydroxyethyl methacrylate and styrene (for example, HEMA-St-HEMA block copolymer) can be preferably used.

An embodiment of the blood vessel expansion appliance of the present invention will be described below.

Figure 44:
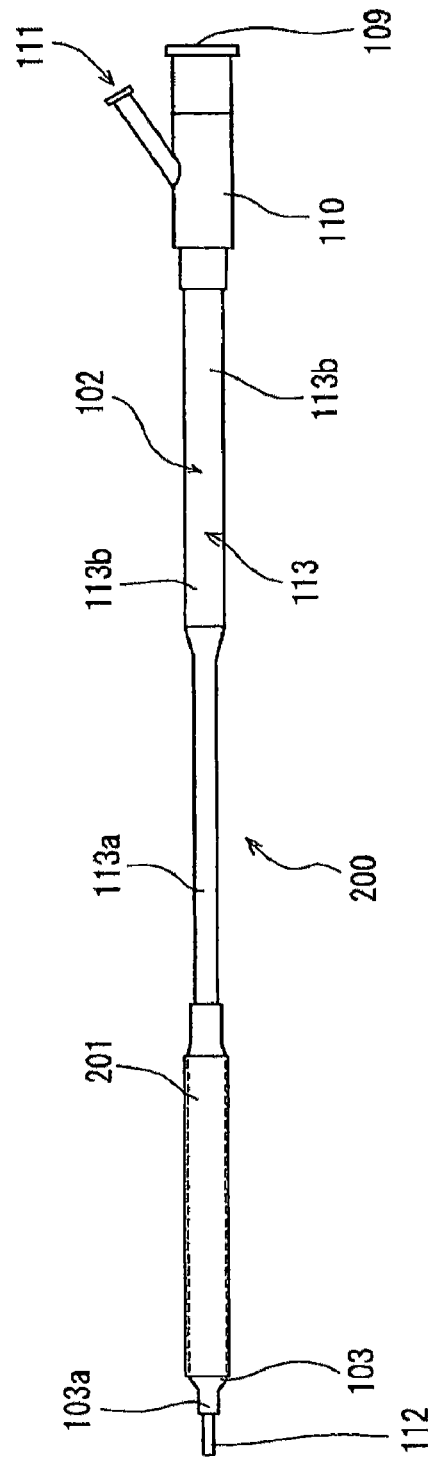
FIG. 44 is a front view showing a stent delivery device of another embodiment of lie present invention.
Figure 45:
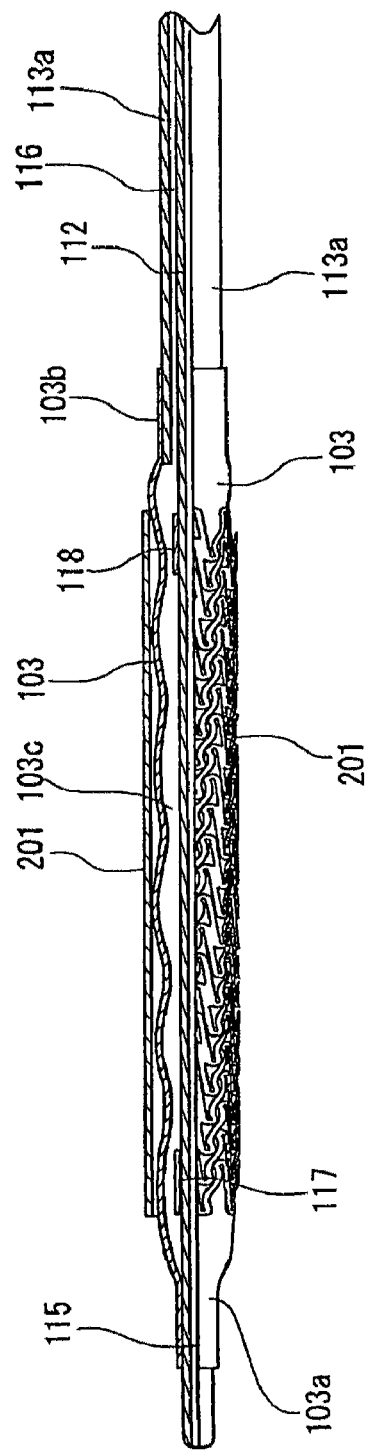
FIG. 45 is a partly enlarged sectional view showing a distal portion of the stent delivery device shown in FIG. 44.
Figure 46:
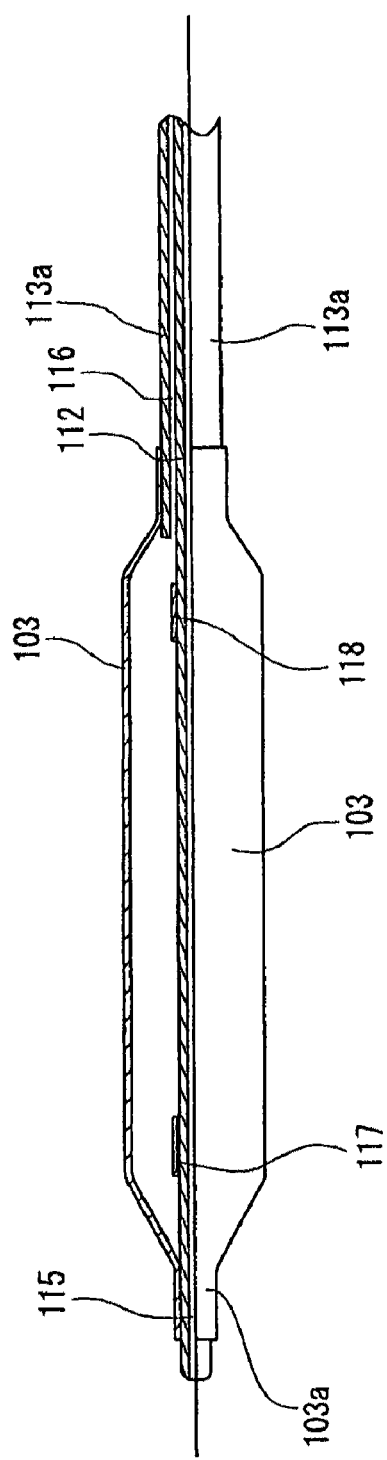
FIG. 46 is an explanatory view for describing the operation of the stent delivery device of an embodiment of the present invention.

FIG. 44 is a front view showing an stent delivery device of an embodiment of the present invention. FIG. 45 is a partly enlarged sectional view showing a distal portion of the stent delivery device shown in FIG. 44. FIG. 46 is an explanatory view for describing the operation of the stent delivery device of an embodiment of the present invention.

A stent delivery device (in other words, blood vessel expansion appliance) 200 of the present invention has a tubular shaft body 102; a balloon 103, foldable and expandable, which is disposed at a distal end of the shaft body 102; and a stent 201 mounted on the folded balloon 103, with the stent 201 covering the balloon 103. The stent 201 is expanded owing to the expansion of the balloon 103.

The stent 140 of the present invention has a large number of wavy annular members 2 arranged adjacently to each other in an axial direction thereof with the adjacent wavy annular members 2 connected with each other. The stent 140 has not less than 13 wavy annular members 2 per 10 mm in the axial direction thereof.

As the stent for use in the blood vessel expansion appliance, it is possible to use a balloon expandable stent which has a diameter whose dimension is so set that it can be inserted into the lumen of the predetermined portion inside the organism, and can be expanded when the force spreading radially outwardly from the inside of the tube is applied thereto.

More specifically, as the stent 201, it is possible to use the stents of the above-described embodiments. It is preferable that the area of the wavy element of the stent is 60 to 80% of the area of the peripheral surface of the stent including vacant spaces thereof when the stent is mounted on the balloon 103.

The shaft body 102 of the stent delivery device 200 of the present invention has a balloon expansion lumen whose one end communicates with the inside of the balloon 103. The stent delivery device 200 has a radiographing member fixed to an outer surface of the shaft body 102 at a position corresponding to the center of the stent or two radiographing members fixed to the outer surface of the shaft body 102 at positions corresponding to one and other ends of the central portion of the stent having a predetermined length.

As shown in FIG. 44, the shaft body 102 of the stent delivery device 200 of this embodiment has a guide wire lumen 115 whose one end is open at a front end of the shaft body 102 and whose other end is open at a rear end of the shaft body 102.

The stent delivery device 200 of the present invention has the tubular shaft body 102, the stent-expanding balloon 103 attached to the front end of the shaft body 102; and the stent 201 mounted on the balloon 103. The shaft body 102 has an inner tube 112, an outer tube 113, and a branch hub 110.

As shown in FIG. 44, the inner tube 112 has the guide wire lumen 115 into which a guide wire is inserted. The length of the inner tube 112 is favorably 100 to 2000 mm and more favorably 150 to 1500 mm. The outer diameter of the inner tube 112 is favorably 0.1 to 1.0 mm and more favorably 0.3 to 0.7 mm. The thickness of the inner tube 112 is favorably 10 to 150 μm and more favorably 20 to 100 μm. The inner tube 112 is inserted into the outer tube 113 to such an extent that the front end of the inner tube 112 projects from the outer tube 113. A balloon-expanding lumen 116 is formed between the outer surface of the inner tube 112 and the inner surface of the outer tube 113 and has a large volume. The front end of the outer tube 113 into which the inner tube 112 is inserted is located a little rearward from the front end of the inner tube 112.

The length of the outer tube 113 is favorably 100 to 2000 mm and more favorably 150-1500 mm. The outer diameter of the outer tube 113 is favorably 0.5 to 1.5 mm and more favorably 0.7 to 1.1 mm. The thickness of the outer tube 113 is favorably 25 to 200 μm and more favorably 50 to 100 μm.

In the stent delivery device 200 of the embodiment the outer tube 113 is composed of a front-end side outer tube 113a and a shaft-body side outer tube 113b joined with the front-end side outer tube 113a. The diameter of the fronted side outer tube 113a decreases taperingly in the region forward from the joining position at which the front-end side outer tube 113a and the shaft body side outer tube 113b are joined with each other. The diameter of a portion of the front-end side outer tube 113a forward from the tapered region has a small diameter.

The outer diameter of the front-end side outer tube 113a at its smaller-diameter portion is favorably 0.50 to 1.5 mm and more favorably 0.60 to 1.1 mm. The outer diameter of the front-end side outer tube 113a at its rear end portion and that of the shaft-body side outer tube 113b are favorably 0.75 to 1.5 mm and more favorably 0.9 to 1.1 mm.

The balloon 103 has a front-end side bonding portion 103a and a rear-end side bonding portion 103b. The front-end side bonding portion 103a is fixed to the inner tube 112 at a position a little rearward from the front end thereof. The rear-end side bonding portion 103b is fixed to the front end of the outer tube 113. The balloon 103 communicates with the balloon-expanding lumen 116 at a position in the vicinity of the proximal end thereof.

A material having a certain degree of flexibility can be preferably used for the inner tube 112 and the outer tube 113. It is favorable to use thermoplastic resins such as polyolefin (for example, polyethylene, polypropylene, ethylene-propylene copolymer, ethylene-vinyl acetate copolymer), polyvinyl chloride, polyamide elastomer, and polyurethane; silicone rubber; and latex rubber. It is more favorable to use the thermoplastic resins. Polyolefin is most favorable of the thermoplastic resins.

As shown in FIG. 45, the balloon 103 is foldable. When the balloon 103 is not expanded, it can be folded over the outer surface of the inner tube 112. As shown in FIG. 46, the balloon 103 has a tubular (preferably, cylindrical) expandable portion having an approximately uniform diameter so that it is possible to expand the stent 201 to be mounted on the balloon 103. The expandable portion is not necessarily cylindrical but may be polygonal. As described above, the front-end side bonding portion 103a of the balloon 103 is liquid-tightly bonded to the inner tube 112, and the rear-end side bonding portion 103b thereof is liquid-tightly bonded to the front end of the outer tube 113 with an adhesive agent or by thermal fusion. The balloon 103 tapers between the expandable portion and each of the bonding portions 103a and 103b.

An expansion space 103c is formed between the inner surface of the balloon 103 and the outer surface of the inner tube 112. The entire circumference of the expansion space 103c communicates with the balloon-expanding lumen 116 at the rear end of the expansion space 103c. Because the expansion space 103c communicates with the balloon-expanding lumen 116 having a comparatively large volume, it is easy to inject an expansion fluid into the balloon 103 through the balloon-expanding lumen 116.

Materials having a certain degree of flexibility can be preferably used for the balloon 103. It is favorable to use thermoplastic resins such as polyolefin (for example, polyethylene, polypropylene, ethylene-propylene copolymer, ethylene-vinyl acetate copolymer, crosslinked ethylene-vinyl acetate copolymer), polyvinyl chloride, polyamide elastomer, polyurethane, polyester (for example, polyethylene terephthalate), polyarylane sulfide (for example, polyphenylene sulfide), silicone rubber, and latex rubber. It is particularly favorable to use an extensible material. A biaxially oriented material can be preferably used for the balloon 103 because of its high degree of strength and expansion.

Regarding the size of the balloon 103, the outer diameter of the expanded cylindrical portion (expandable portion) thereof is favorably in the range of 2 to 4 mm and more favorably 2.5 to 3.5 mm. The length of the balloon 103 is favorably in the range of 10 to 50 mm and more favorably in the range of 20 to 40 mm. The outer diameter of the front-end side bonding portion 103a is favorably in the range of 0.9 to 1.5 mm and more favorably in the range of 1 to 1.3 mm. The length of the front-end side bonding portion 103a is favorably in the range of 1 to 5 mm and more favorably 1 to 1.3 mm. The outer diameter of the rear-end side bonding portion 103b is favorably in the range of 1 to 1.6 mm and more favorably 1.1 to 1.5 mm. The length of the rear-end side bonding portion 103b is favorably in the range of 1 to 5 mm and more favorably in the range of 2 to 4 mm.

As shown in FIG. 46, the stent delivery device 200 has two radiographing members 117, 118 fixed to the outer surface of the shaft body at positions corresponding to one and other ends of the cylindrical portion (expandable portion) of the stent when the stent is expanded. Further the stent delivery device 200 may have two radiographing members fixed to the outer surface of the shaft body (in this embodiment, inner tube 112) at positions corresponding to one and other ends of the central portion of the stent 201 having a predetermined length. Further the stent delivery device (blood vessel expansion appliance) 200 may have one radiographing member fixed to the outer surface of the shaft body at a position corresponding to the central portion of the stent 201.

The radiographing members 117 and 118 are preferably in the shape of a ring having a predetermined length or a coiled wire. It is preferable that the radiographing members 117, and 118 are made of gold, platinum, tungsten or alloys thereof or a silver-palladium alloy.

The stent 201 is mounted on the balloon 103, with the stent covering the folded balloon 103. The stent is formed by processing a metal pipe having an inner outer diameter of the stent smaller than the inner diameter thereof at the time when the stent is expanded and larger than the outer diameter of the folded balloon. The balloon is inserted into the formed stent and a force is uniformly applied to the outer surface of the stent to decrease the diameter of the stent. In this manner, the production of the stent is completed. That is, production of the stent 201 is completed when the stent 201 is mounted on the balloon by compressing the stent.

A linear rigidity-imparting member (not shown) may be inserted between the inner tube 112 and the outer tube 113, namely, into the balloon-expanding lumen 116. The rigidity-imparting member prevents excess bending of the shaft body of the stent delivery device 200 at bent portions of blood vessels without much deteriorating the flexibility of the stent delivery device 200 and facilitates the insertion of the frond end of the stent delivery device 200 into the bent portions of blood vessels. It is preferable that the diameter of the frond end of the rigidity-imparting member is set smaller than those of the other portions thereof by grinding or the like. It is preferable that front end of the small-diameter portion extends to the vicinity of the front end of the outer tube 113 of the body of the stent delivery device 200. It is preferable that the rigidity-imparting member consists of a metal wire having a diameter 0.05 to 1.50 mm and more favorably 0.10 to 1.00 mm. The rigidity-imparting member is made of favorably an elastic metal such as stainless steel or a super elastic alloy and more favorably high-strength stainless steel for a spring or a wire of the super elastic alloy.

As shown in FIG. 44, the stent delivery device 200 of this embodiment has a branched hub 110 fixed to the rear end thereof. The branched hub 110 has an inner-tube hub, fixed to the inner tube 112, which communicates with the guide wire lumen 115 and has a guide wire introducing opening 109 forming a guide wire port and an outer-tube hub, fixed to the outer tube 113, which communicates with the balloon-expanding lumen 116 and has an injection port 111. The outer-tube hub and the inner-tube hub are fixed to each other. As the material of the branched hub 110, thermoplastic resin such as polycarbonate, polyamide, polysulfone, polyacrylate, and methacrylate-butylene-stylene copolymer can be preferably used.

The construction of the stent delivery device is not limited to the above-described one. For example, the stent delivery device may have a guide wire insertion opening communicating with the guide wire lumen, disposed at a central portion thereof.

The stent of the present invention to be implanted in the organism has a large number of the wavy annular members arranged adjacently to each other in the axial direction thereof with the adjacent wavy annular members connected with each other. The stent has not less than 13 wavy annular members per 10 mm in the axial direction thereof. Therefore the stent has a high expanded-state retention force and a sufficient follow-up performance.

What is claimed is:

1. A stent comprising: a plurality of wavy annular members arranged adjacently to each other in an axial direction thereof, with said adjacent wavy annular members connected with each other,
    wherein each of said wavy annular members has a plurality of one-end side bent portions each having an apex at one side of said stent in an axial direction thereof and a plurality of other-end side bent portions each having an apex at said other side of said stent in said axial direction thereof;
    said apex of each of said one-end side bent portions of each wavy annular member penetrates into a space formed between said adjacent other-end side bent portions of one of said adjacent wavy annular members, and said apex of each of said other-end side bent portions of said each wavy annular member penetrates into a space formed between said adjacent one-end side bent portions of said other of said adjacent wavy annular members; and
    said apex of said one-end side bent portion of each of said wavy annular members and said apex of said other-end side bent portion of said adjacent wavy annular member curve in an approach direction, thus engaging each other;
    wherein said wavy annular member is composed of a plurality of first stratum portions each of which consists of a straight-line portion extended obliquely at a predetermined angle with respect to an axis of said stent and a plurality of second stratum portions each of which consists of an S-shaped curved portion which connects an upper end of one adjacent first stratum portion and a lower end of an adjacent first stratum portion to each other, said straight-line portion of said wavy annular member being connected to said straight-line portion of said adjacent wavy annular member and not connected to said apex of said adjacent wavy annular member.

2. A stent according to claim 1, wherein a connection portion is provided between said apexes of said bent portions of said adjacent wavy annular members.

3. A stent according to claim 2, wherein adjacent wavy annular members disposed at one end of said stent are connected to each other by a plurality of connection portions; and adjacent wavy annular members disposed at other end of said stent are connected to each other by a plurality of connection portions.

4. A stent according to claim 1, wherein said stent has a short connection portion shifted to some extent toward said one end of said stent or said other end thereof with respect to said apex of said one-end side bent portion of each of said wavy annular members and said other-end side bent portion of said adjacent wavy annular member.

5. A stent according to claim 4, wherein said connection portion connects a rear of a portion where said apex of said one-end side bent portion of each of said wavy annular members and said apex of said other-end side bent portion of said adjacent wavy annular member are proximate to each other, with said apexes engaging each other.

6. A stent according to claim 4, wherein said connection portion connects a portion where said apex of said one-end side bent portion of each of said wavy annular members and said apex of said other-end side bent portion of said adjacent wavy annular member are proximate to each other, with said apexes engaging each other.

7. A stent according to claim 4, wherein said connection portion has a first connection portion connecting a rear of a portion where said apex of said one-end side bent portion of each said wavy annular members and said apex of said other-end side bent portion of said adjacent wavy annular member are proximate to each other, with said apexes engaging each other; and a second connection portion connecting a portion where said apex of said one-end side bent portion of each of said wavy annular members and said apex of said other-end side bent portion of said adjacent wavy annular member are proximate to each other, with said apexes engaging each other.

8. A stent according to claim 7, wherein said adjacent wavy annular members are connected to each other by said first connection portion or said second connection portion; and said first connection portion and said second connection portion are arranged alternately in an axial direction of said stent.

9. A stent according to claim 7, wherein said adjacent wavy annular members are connected to each other by a plurality of said first connection portions or a plurality of said second connection portions; and said first connection portions and said second connection portions are arranged alternately in an axial direction of said stent.

10. A stent according to claim 7, wherein said stent has a portion connecting said adjacent wavy annular members to each other by said two first connection portions substantially opposed to each other with respect to an axis of said stent and a portion connecting said adjacent wavy annular members to each other by said two second connection portions substantially opposed to each other with respect to said axis of said stent said first and second connection portions are formed alternately in said axial direction of said stent; and said first connection portions and said second connection portions are substantially equiangularly disposed with respect to said axis of said stent.

11. A stent according to claim 4, wherein said connection portion is only connection portions connecting s a rear of a portion where said apex of said one-end side bent portion of each of said wavy annular members and said apex of said other-end side bent portion of said adjacent wavy annular member are proximate to each other, with said apexes engaging each other, and said connection portions are formed uncontinuously in said axial direction of said stent.

12. A stent according to claim 1, wherein a wavy line element composing said wavy annular member curves and does not have a straight-line portion substantially.

13. A stent according to claim 1, wherein an axial length between said proximate apexes of said adjacent wavy annular members is set to not less than 0.2 mm.

14. A stent according to claim 1, wherein wavy annular member has an apex of the one-end side bent portion axially shorter than the other apexes of the wavy annular member and an apex of the other-end side bent portion axially shorter than the other apexes of the wavy annular member, said apex of the one-end side bent portion and said apex of the other-end side bent portion are proximate and form an unengaging portion.

15. A stent according to claim 14, wherein said stent has a connection portion connecting or integrating said apex of the one-end side bent portion axially shorter than the other apexes of the wavy annular member and to apex of the other-end side bent portion axially shorter than the other apexes of the wavy annular member.

16. A stent according to claim 1, wherein said stent is formed as a tube, has a diameter whose dimension is so set that said stent can be inserted into a lumen of a predetermined portion inside an organism, and can be expanded when a force which spreading radially outward from an inside of said tube is applied thereto.

17. A stent according to claim 1, wherein said stent has a large number of said wavy annular members arranged adjacently to each other in an axial direction thereof with said adjacent wavy annular members connected with each other, wherein said stent has not less than 13 wavy annular members per 10 mm in the axial direction thereof.

18. A stent according to claim 17, wherein each of said wavy annular members has a plurality of one-end side bent portions each having an apex at a one end-side of said stent in an axial direction thereof and a plurality of other-end side bent portions each having an apex at an other end-side of said stent in said axial direction thereof; and said apex of each of said one-end side bent portions of each of said wavy annular members penetrates into a space formed between said other-end side bent portions of one of said adjacent wavy annular members, whereas said apex of each of said other-end side bent portions of said wavy annular member penetrates into a space formed between said one-end side bent portions of other of said adjacent wavy annular members.

19. A stent according to claim 18, wherein said apex of said one-end side bent portion of each of said wavy annular members and said apex of said other-end side bent portion of said adjacent wavy annular member engage each other.

20. A stent according to claim 19, further comprising a back-side position connection portion which connects a back side position of a portion where said apex of said one-end side bent portion of one of said wavy annular member and said apex of said other-end side bent portion of said adjacent wavy annular member engage each other.

21. A stent according to claim 19, further comprising an engaged-position connection portion which connects a position where said apex of said one-end side bent portion of said one wavy annular member and said apex of said other-end side bent portion of said adjacent wavy annular member engage each other.

22. A stent according to claim 17, further comprising an apex connection portion which connects said apexes of said one-end side bent portions of said adjacent wavy annular members to each other or said apexes of said other-end side bent portions of said adjacent wavy annular members to each other.

23. A stent according to claim 22, wherein a portion of said wavy annular member close to said apex connection portion is curved; and said apex connection portion has a configuration corresponding to a curved configuration of said wavy annular member.

24. A stent according to claim 17, wherein said adjacent wavy annular members are connected to each other with a plurality of said connection portions.

25. A stent according to claim 17, wherein an axial length of said wavy annular member in an axial direction of said stent is set to 0.25 to 1.25 mm.

26. A stent according to claim 17, wherein a line width of said wavy annular member is set to 0.05 to 0.15 mm.

27. A stent according to claim 17, wherein a number of said apexes of said one-end side bent portions of each of said wavy annular members and that of said apexes of said other-end side bent portions of each of said wavy annular members are set to 6 to 18.

28. A stent according to claim 17, wherein an axial length of said stent is set to 5 to 40 mm.

29. A stent according to claim 17, wherein a diameter of said stent is set to 1.25 to 5.0 mm.

30. A stent according to claim 17, wherein said stent is formed substantially as a tube and has a diameter whose dimension is set so that said stent can be inserted into a lumen inside an organism; and said stent can be expanded when a force spreading radially outward from an inside of said tube is applied thereto.

31. A stent delivery device comprising: a tubular shaft body; a balloon, foldable and expandable, which is disposed at a distal end of said shaft body; and a stent which is mounted on said folded balloon, with said stent covering said balloon and is expanded owing to expansion of said balloon, wherein said stent is a stent according to claim 17.

32. A stent according to claim 1, wherein said apex of said one-end side bent portion of each of said wavy annular members and said apex of said other-end side bent portion of said adjacent wavy annular member are proximate to each other.

33. A stent according to claim 32, wherein said one-end side bent portion directly contacts said other-end side bent portion of said adjacent wavy annular member.

34. A stent comprising: a plurality of wavy annular members arranged adjacently to each other in an axial direction thereof, with said adjacent wavy annular members connected with each other,
wherein each of said wavy annular members has a plurality of one-end side bent portions each having an apex at one side of said stent in an axial direction thereof and a plurality of other-end side bent portions each having an apex at said other side of said stent in said axial direction thereof;
an apex of each of said one-end side bent portions of each wavy annular member penetrates into a space formed between said adjacent other-end side bent portions of one of said adjacent wavy annular members, and an apex of each of said other-end side bent portions of said each wavy annular member penetrates into a space formed between said adjacent one-end side bent portions of said other of said adjacent wavy annular members; and
said apex of said one-end side bent portion of each of said wavy annular members and said apex of said other-end side bent portion of said adjacent wavy annular member are depressed and engage each other;
wherein said wavy annular member is composed of a plurality of first stratum portions each of which consists of a straight-line portion extended obliquely at a predetermined angle with respect to an axis of said stent and a plurality of second stratum portions each of which consists of an S-shaped curved portion which connects an upper end of one adjacent first stratum portion and a lower end of an adjacent first stratum portion to each other, said straight-line portion of said wavy annular member being connected to said straight-line portion of said adjacent wavy annular member and not connected to said apex of said adjacent wavy annular member.

35. A stent delivery device comprising a tubular shaft body; a balloon, foldable and expandable, which is disposed at a distal end of said shaft body; and a stent which is mounted on said folded balloon, with said stent covering said folded balloon and which expands owing to expansion of said balloon, wherein said stent is any one of stents according to claim 34.

36. A stent delivery device according to claim 35, wherein an area of a wavy element of said stent is 60 to 80% of an area of a peripheral surface of said stent including vacant spaces thereof when said stent is mounted on said balloon.

37. A stent delivery device according to claim 35, wherein an axial length between said proximate apexes of said adjacent wavy annular members is set to not less than 0.2 mm when said stent is mounted on said balloon.

38. A stent according to claim 34, wherein said apex of said one-end side bent portion of each of said wavy annular members and said apex of said other-end side bent portion of said adjacent wavy annular member are proximate to each other.

39. A stent according to claim 38, wherein said one-end side bent portion directly contacts said other-end side bent portion of said adjacent wavy annular member.

* * * * *